US008216571B2

(12) United States Patent
Ramachandra et al.

(10) Patent No.: US 8,216,571 B2
(45) Date of Patent: Jul. 10, 2012

(54) FULLY HUMAN ANTI-VEGF ANTIBODIES AND METHODS OF USING

(75) Inventors: Sumant Ramachandra, Northbrook, IL (US); Walter Robert Bishop, Pompton Plains, NJ (US); Linda Masat, Walnut Creek, CA (US); Chao Bai Huang, San Leandro, CA (US); Toshihiko Takeuchi, Oakland, CA (US); Seema Kantak, Pacifica, CA (US); Chin-Yi Huang, Fremont, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 12/739,383

(22) PCT Filed: Oct. 20, 2008

(86) PCT No.: PCT/US2008/080531
§ 371 (c)(1),
(2), (4) Date: Dec. 10, 2010

(87) PCT Pub. No.: WO2009/055343
PCT Pub. Date: Apr. 30, 2009

(65) Prior Publication Data
US 2011/0097340 A1 Apr. 28, 2011

Related U.S. Application Data

(60) Provisional application No. 60/981,808, filed on Oct. 22, 2007, provisional application No. 61/046,370, filed on Apr. 18, 2008.

(51) Int. Cl.
*A61K 39/395* (2006.01)
*A61K 39/00* (2006.01)
*C07K 16/00* (2006.01)
*C07K 16/18* (2006.01)
*C07K 16/22* (2006.01)
*C07K 16/42* (2006.01)
*C12P 21/08* (2006.01)
*C12P 21/02* (2006.01)

(52) U.S. Cl. ............... 424/130.1; 424/141.1; 424/142.1; 424/145.1; 424/178.1; 424/181.1; 435/810; 530/387.1; 530/387.2; 530/387.3; 530/388.1; 530/388.15; 530/388.24; 530/389.2; 530/391.7

(58) Field of Classification Search .................. None
See application file for complete search history.

(56) References Cited

U.S. PATENT DOCUMENTS

| 4,492,537 | A | 1/1985 | Awerkamp |
|---|---|---|---|
| 4,766,106 | A | 8/1988 | Katre et al. |
| 4,816,567 | A | 3/1989 | Cabilly et al. |
| 4,917,888 | A | 4/1990 | Katre et al. |
| 5,196,446 | A | 3/1993 | Levitzki et al. |
| 5,595,898 | A | 1/1997 | Robinson et al. |
| 5,616,582 | A | 4/1997 | Barker |
| 5,646,153 | A | 7/1997 | Spada et al. |
| 5,656,655 | A | 8/1997 | Spada et al. |
| 5,679,683 | A | 10/1997 | Bridges et al. |
| 5,762,923 | A | 6/1998 | Gross et al. |
| 5,766,582 | A | 6/1998 | Yuen et al. |
| 5,766,886 | A | 6/1998 | Studnicka et al. |
| 6,005,079 | A | 12/1999 | Casterman et al. |
| 6,217,866 | B1 | 4/2001 | Schlessinger et al. |
| 7,192,737 | B2 | 3/2007 | Horwitz |
| 7,208,582 | B2 * | 4/2007 | Rosen et al. ............... 530/387.1 |
| 8,034,905 | B2 * | 10/2011 | Kavlie et al. ............... 530/387.3 |
| 2003/0175274 | A1 | 9/2003 | Rosen et al. |
| 2004/0209878 | A1 | 10/2004 | Guzi et al. |
| 2006/0121604 | A1 | 6/2006 | Handa et al. |
| 2007/0128111 | A1 | 6/2007 | Reilly et al. |
| 2007/0160608 | A1 | 7/2007 | Fyfe et al. |
| 2011/0076279 | A1 * | 3/2011 | Ramachandra et al. ... 424/158.1 |

FOREIGN PATENT DOCUMENTS

| EP | 0236987 A2 | 9/1987 |
|---|---|---|
| EP | 0404097 A2 | 12/1990 |
| EP | 0593868 A1 | 9/1994 |
| WO | WO 93/11161 | 6/1993 |
| WO | WO 94/04678 | 3/1994 |
| WO | WO 94/25591 | 11/1994 |
| WO | WO 95/13090 | 5/1995 |
| WO | WO 99/35146 | 7/1999 |
| WO | WO 00/71129 A1 | 11/2000 |
| WO | WO 01/29025 A2 | 4/2001 |
| WO | WO 02/32861 A2 | 4/2002 |
| WO | WO 03/088900 A2 | 10/2003 |
| WO | WO 2004/000105 A2 | 12/2003 |
| WO | WO 2004/009542 A2 | 1/2004 |
| WO | WO 2004/009601 A1 | 1/2004 |
| WO | WO 2004/013145 A1 | 2/2004 |
| WO | WO 2004/033693 A1 | 4/2004 |

OTHER PUBLICATIONS

Al-Lazikani, B., et al., "Standard Conformations for the Canonical Structures of Immunoglobulins," J. Mol. Biol. 273:927-948 (1997).
Amoroso, A., et al., "Vascular Endothelial Growth Factor: A Key Mediator of Neoangiogenesis. A Review," Eur. Rev. Med. Pharmacol. Sci. 1:17-25 (1997).
Ashida, S., et al., "Molecular Detection of Von Hippel-Lindau Gene Mutations in Urine and Lymph Node Samples in Patients with Renal Cell Carcinoma: Potential Biomarkers for Early Diagnosis and Postoperative Metastatic Status," J. Urol. 169:2089-2093 (2003).
Atadja, P., et al., "Selective Growth Inhibition of Tumor Cells by a Novel Histone Deacetylase Inhibitor, NVP-LAQ824," Cancer Res. 64:689-695 (2004).

(Continued)

Primary Examiner — Phuong Huynh

(57) ABSTRACT

Disclosed herein are fully human antibodies and antigen-binding fragments thereof that specifically bind human VEGF and inhibit VEGF binding to VEGF-R1 and VEGF-R2, and therefore inhibit VEGF signaling. The antibodies and antigen-binding fragments disclosed herein may be used, for example, to treat angiogenesis and conditions associated with angiogenesis both in vivo and in vitro.

21 Claims, 36 Drawing Sheets

OTHER PUBLICATIONS

Azzazy, H. M. E., et al., "Phage Display Technology: Clinical Applications and Recent Innovations," Clin. Biochem. 35:425-445 (2002).

Beisler, J. A., "Potential Antitumor Agents. 1. Analogs of Camptothecin," J. Med. Chem. 14(11):1116-1118 (1971).

Berkman, R. A., et al., "Expression of the Vascular Permeability Factor/Vascular Endothelial Growth Factor Gene in Central Nervous System Neoplasms," J. Clin. Invest. 91:153-159 (1993).

Brown, L. F., et al., "Expression of Vascular Permeability Factor (Vascular Endothelial Growth Factor) and Its Receptors in Adenocarcinomas of the Gastrointestinal Tract," Cancer Res. 53:4727-4735 (1993).

Brown, L. F., et al., "Expression of Vascular Permeability Factor (Vascular Endothelial Growth Factor) and Its Receptors in Breast Cancer," Human Pathol. 26:86-91 (1995).

Chaouche, M., et al., "Oxaliplatin, 5-Fluorouracil, and Folinic Acid (Folfox) in Patients with Metastatic Renal Cell Carcinoma," Am. J. Clin. Oncol. 23(3):288-289 (2000).

Chothia, C., "Domain Association in Immunoglobulin Molecules: The Packing of Variable Domains," J. Mol. Biol. 186:651-663 (1985).

Chothia, C., et al., "Canonical Structures for the Hypervariable Regions of Immunoglobulins," J. Mol. Biol. 196:901-917 (1987).

Chothia, C., et al., "Conformations of Immunoglobulin Hypervariable Regions," Nature 342:877-883 (1989).

Cumbers, S. J., et al., "Generation and Iterative Affinity Maturation of Antibodies In Vitro Using Hypermutating B-Cell Lines," Nat. Biotechnol. 20:1129-1134 (2002).

De Gramont, A., et al., "Leucovorin and Fluorouracil with or without Oxaloplatin as First-Line Treatment in Advanced Colorectal Cancer," J. Clim. Oncol. 18:2938-2947 (2000).

Dimmeler, S., et al., "Phosphorylation of the Endothelial Nitric Oxide Synthase at Ser-1177 is Required for VEGF-Induced Endothelial Cell Migration," FEBS Letters 477:258-262 (2000).

Dupont, J., et al., "Safety and Pharmacokinetics of Intravenous VEGF Trap in a Phase I Clinical Trial of Patients with Advanced Solid Tumors," Suppl. J. Clin. Oncol. 2005 ASCO Annual Meeting Proceedings 23(16S):199s (2005).

Dvorak, H. F., et al., "Vascular Permeability Factor/Vascular Endothelial Growth Factor, Microvascular Hyperpermeability, and Angiogenesis," Am. J. Pathol. 146(5):1029-1039 (1995).

Erikkson, U., et al., "Structure, Expression and Receptor-Binding Properties of Novel Vascular Endothelial Growth Factors," Curr. Top. Microbiol. Immunol. 237:41-57 (1999).

Erlichman, C., et al., "The HER Tyrosine Kinase Inhibitor CI1033 Enhances Cytotoxicity of 7-Ethyl-10-Hydroxycamptothecin and Topotecan by Inhibiting Breast Cancer Resistance Protein-Mediated Drug Efflux," Cancer Res. 61:739-748 (2001).

Ferrara, N., et al., "Discovery and Development of Bevacizumab, An Anti-VEGF Antibody for Treating Cancer," Nat. Rev. Drug Discov. 3:391-400 (2004).

Ferrara, N., "Vascular Endothelial Growth Factor: Molecular and Biological Aspects," Curr. Top. Microbiol. Immunol. 237:1-30 (1999).

Fishwild, D. M., et al., "High-Avidity Human IgGκ Monoclonal Antibodies from a Novel Strain of Minilocus Transgenic Mice," Nat. Biotechnol. 14:845-851 (1996).

Fry, D. W., et al., "A Specific Inhibitor of the Epidermal Growth Factor Receptor Tyrosine Kinase," Science 265:1093-1095 (1994).

Fuh, G., et al., "Structure-Function Studies of Two Synthetic Anti-Vascular Endothelial Growth Factor Fabs and Comparison with the Avastin™ Fab," J. Biol. Chem. 281(10):6625-6631 (2006).

Furumai, R., et al., "FK228 (Depsipeptide) as a Natural Prodrug that Inhibits Class I Histone Deacetylases," Cancer Res. 62:4916-4921 (2002).

Garner, R. C., et al., "Evaluation of Accelerator Mass Spectrometry in a Human Mass Balance and Pharmacokinetic Study-Experience with $^{14}$C-Labeled (R)-6-[Amino(4-Chlorophenyl)(1-Methyl-1H-Imidazol-5-YL)Methyl]-4-)3-Chlorophenyl)-1-Methyl-2(1H)-Quinolinone (R115777), A Farnesyl Transferase Inhibitor," Drug Metab. Dispos. 30(7):823-830 (2002).

Garrido, J.L., et al., "Antineoplastic Activity of BCG: Location of Antineoplastic Glycans in the Cellular Integument of *Mycobacterium bovis*, BCG Vaccine, Connaught Substrain," Cytobios 90:47-65 (1997).

Giri, J. G., et al., "Utilization of the β and γ Chains of the IL-2 Receptor by the Novel Cytokine IL-15," EMBO J. 13(12):2822-2830 (1994).

Hamers-Casterman, C., et al., "Naturally Occurring Antibodies Devoid of Light Chains," Nature 363:446-448 (1993).

Harris, A. L., "Von Hippel-Lindau Syndrome: Target for Anti-Vascular Endothelial Growth Factor (VEGF) Receptor Therapy," The Oncologist 5(suppl.) 1:32-36 (2000).

Hawkins, R. E., et al., "Selection of Phage Antibodies by Binding Affinity Mimicking Affinity Maturation," J. Mol. Biol. 226:889-896 (1992).

Hidalgo, M., et al., "Phase I and Pharmacologic Study of OSI-774, An Epidermal Growth Factor Receptor Tyrosine Kinase Inhibitor, in Patients with Advanced Solid Malignancies," J. Clin. Oncol. 19:3267-3279 (2001).

Holash, J., et al., "VEGF-Trap: A VEGF Blocker with Potent Antitumor Effects," Proc. Natl. Acad. Sci. USA 99(17):11393-11398 (2002).

Holliger, P., et al., "Diabodies: Small Bivalent and Bispecific Antibody Fragments," Proc. Natl. Acad. Sci. USA 90:6444-6448 (1993).

Huang, J., et al., "PTEN Modulates Vascular Endothelial Growth Factor-Mediated Signaling and Angiogenic Effects," J. Biol. Chem. 277(13):10760-10766 (2002).

Hunt, J. T., et al., "Discovery of (R)-7-Cyano-2,3,4,5-Tetrahydro-1-(1H-Imidazol-4-ylmethyl)-3-(Phenylmethyl)-4-(20Thienylsulfonyl)-1H-1,4-Benzodiazepine (BMS-214662), A Farnesyltransferase Inhibitor with Potent Preclinical Antitumor Activity," J. Med. Chem. 43(20):3587-3595 (2000).

Hunt, S., "Technology Evaluation: IMC-1C11, ImClone Systems," Curr. Opin. Mol. Ther. 3(4):418-424 (2001).

Huston, J. S., et al., "Protein Engineering of Antibody Binding Sites: Recovery of Specific Activity in An Anti-Digoxin Single-Chain Fv Analogue Produced in *Escherichia coli*," Proc. Natl. Acad. Sci. USA 85:5879-5883 (1988).

Jostock, T., et al., "Rapid Generation of Functional Human IgG Antibodies Derived From Fab-On-Phage Display Libraries," J. Immunol. Methods 289:65-80 (2004).

Katre, N. V., "Immunogenicity of Recombinant IL-2 Modified By Covalent Attachment of Polyethylene Glycol," J. Immunol. 144:209-213 (1990).

Katz, M. D., et al., "Octreotide, A New Somatostatin Analogue," Clin. Pharm. 8:255-273 (1989).

Khamaisi, M., et al., "The Emerging Role of VEGF in Diabetic Kidney Disease," Nephrol. Dial. Transplant 18:1427-1430 (2003).

Kim, K. S., et al., "Anti-Angiogenic Activity of the Recombinant Kringle Domain of Urokinase and Its Specific Entry into Endothelial Cells," J. Biol. Chem. 278(13):11449-11456 (2003).

Kimbro, K. S., et al., "Hypoxia-Inducible Factor-1 in Human Breast and Prostate Cancer," Endpcr. Relat. Cancer 13:739-749 (2006).

Koch-Nolte, F., et al., "Single Domain Antibodies from Llama Effectively and Specifically Block T Cell Ecto-ADP-Ribosyltransferase ART2.2 In Vivo," FASEB J. 21:3490-3498 (2007).

Lee, F. Y. F., et al., "BMS-247550: A Novel Epothilone Analog with a Mode of Action Similar to Paclitaxel but Possessing Superior Antitumor Efficacy," Clin. Cancer Res. 7:1429-1437 (2001).

Lee, Y. K., et al., "VEGF Receptor Phosphorylation Status and Apoptosis is Modulated By a Green Tea Component, Epigallocatechin-3-Gallate (EGCG), in B-cell Chronic Lymphocytic Leukemia," Blood 104:788-794 (2004).

Li, J., et al., "Human Antibodies for Immunotherapy Development Generated Via a Human B Cell Hybridoma Technology," Proc. Natl. Acad. Sci. USA 103:3557-3562 (2006).

Liang, W.C., et al., "Cross-Species Vascular Endothelial Growth Factor (VEGF)-Blocking Antibodies Completely Inhibit the Growth of Human Tumor Xenografts and Measure the Contribution of Stromal VEGF," J. Biol. Chem. 281(2):951-961 (2006).

Lonberg, N., "Human Antibodies from Transgenic Animals," Nat. Biotechnol. 23(9):1117-1125 (2005).

Lowman, H. B., "Phage Display of Peptide Libraries on Protein Scaffolds," Methods Mol. Biol. 87:249-264 (1998).

Mattern, J., et al., "Association of Vascular Endothelial Growth Factor Expression with Intratumoral Microvessel Density and Tumour Cell Proliferation in Human Epidermoid Lung Carcinoma," Brit. J. Cancer 73:931-934 (1996).

McColley, S. A., et al., "Serum Vascular Endothelial Growth Factor Is Elevated in Cystic Fibrosis and Decreases with Treatment of Acute Pulmonary Exacerbation," Am. J. Respir. Crit. Care Med. 161:1877-1880 (2000).

Mendel, D. B., et al., "In Vivo Antitumor Activity of SU11248, A Novel Tyrosine Kinase Inhibitor Targeting Vascular Endothelial Growth Factor and Platelet-Derived Growth Factor Receptors: Determination of a Pharmacokinetic/Pharmacodynamic Relationship," Clin. Cancer Res. 9:327-337 (2003).

Mendez, M. J., et al., "Functional Transplant of Megabase Human Immunoglobulin Loci Recapitulates Human Antibody Response in Mice," Nat. Genet. 15:146-156 (1997).

Miao, H.Q., et al. 2005. Biochem Biophys Res Commun 345:438-445.

Michaelis, M., et al., "Valproic Acid Inhibits Angiogenesis In Vitro and In Vivo," Mol. Pharmacol. 65(3):520-527 (2004).

Michels, S., et al., "Ranibizumab Therapy for Neovascular Age-Related Macular Degeneration," Retinal Physician 1:16-22 (2004).

Michels, S., et al., "Systemic Bevacizumab (Avastin) Therapy for Neovascular Age-Related Macular Degeneration: Twelve-Week Results of an Uncontrolled Open-Label Clinical Study," Opthamol. 112:1035-1047 (2005).

Murohara, T., et al., "Vascular Endothelial Growth Factor/Vascular Permeability Factor Enhances Vascular Permeability Via Nitric Oxide and Prostacyclin," Circulation 97:99-107 (1998).

Muyldermans, S., et al., "Recognition of Antigens by Single-Domain Antibody Fragments: the Superfluous Luxury of Paired Domains," Trends Biochem. Sci. 26:230-235 (2001).

Nguyen, V. K., et al., "Functional Heavy-Chain Antibodies in Camelidae," Adv. Immunol. 79:261-296 (2001).

Nguyen, V. K., et al., "Heavy-Chain Antibodies in Camelidae; A Case of Evolutionary Innovation," Immunogenetics 54:39-47 (2002).

Panek, R. L., et al., "In Vitro Pharmacological Characterization of PD 166285, A New Nanomolar Potent and Broadly Active Protein Tyrosine Kinase Inhibitor," J. Pharmacol. Exp. Ther. 283(3):1433-1444 (1997).

Presta, L. G., et al., "Humanization of an Anti-Vascular Endothelial Growth Factor Monoclonal Antibody for the Therapy of Solid Tumors and Other Disorders," Cancer Res. 57:4593-4599 (1997).

Riechmann, L., et al., "Single Domain Antibodies: Comparison of Camel VH and Camelised Human VH Domains," J. Immunol. Methods. 231:25-38 (1999).

Rosenfeld, P.J., et al., "Optical Coherence Tomography Findings After Intravitreal Injection of Bevacizumab for Neovascular Age-Related Macular Degeneration," Opthalmic Surg. Lasers Imaging 36(4):331-335 (2005).

Rusnak, D. W., et al., "The Effects of the Novel, Reversible Epidermal Growth Factor Receptor/ErbB-2 Tyrosine Kinase Inhibitor, GW2016, On the Growth of Human Normal and Tumor-Derived Cell Lines In Vitro and In Vivo," Mol. Cancer Ther. 1:85-94 (2001).

Sebolt-Leopold, J. S., et al., "Blockade of the MAP Kinase Pathway Suppresses Growth of Colon Tumors In Vivo," Nat. Med. 5(7):810-816 (1999).

Sehgal, S. N., et al., "Rapamycin: A Novel Immunosuppressive Macrolide," Med. Res. Rev. 14:1-22 (1994).

Senderowicz, A. M., et al., "Small Molecule Modulators of Cyclin-Dependent Kinases for Cancer Therapy," Oncogene 19:6600-6606 (2000).

Shields, R. L., et al., "Lack of Fucose on Human IgG1 N-Linked Oligosaccharide Improves Binding to Human FcγRIII and Antibody-Dependent Cellular Toxicity," J. Biol. Chem. 277(30):26733-26740 (2002).

Shinkawa, T., et al., "The Absence of Fucose but Not the Presence of Galactose or Bisecting N-Acetylglucosamine of Human IgG1 Complex-Type Oligosaccharides Shows the Critical Role of Enhancing Antibody-Dependent Cellular Cytotoxicity," J. Biol. Chem. 278(5):3466-3473 (2003).

Smaill, J. B., et al., "Tyrosine Kinase Inhibitors. 17. Irreversible Inhibitors of the Epidermal Growth Factor Receptor: 4-(Phenylamino)Quinazoline- and 4-(Phenylamino)Pyrido[3,2-d]Pyrimidine-6-Acrylamides Bearing Additional Solubilizing Functions," J. Med. Chem. 43:1380-1397 (2000).

Stork, G., et al., "The Total Synthesis of dl-Camptothecin," J. Am. Chem. Soc. 93(16):4074-4075 (1971).

Tamura, M., et al., "Inhibition of Cell Migration, Spreading, and Focal Adhesions by Tumor Suppressor PTEN," Science 280:1614-1617 (1998).

Thomas, A. L., et al., "Vascular Endothelial Growth Factor Receptor Tyrosine Kinase Inhibitors: PTK787/ZK 222584," Semin. Oncol. 30(suppl 6):32-38 (2003).

Tomizuka, K., et al., "Double Trans-Chromosomic Mice: Maintenance of Two Individual Human Chromosome Fragments Containing Ig Heavy and κ Loci and Expression of Fully Human Antibodies," Proc. Natl. Acad. Sci. USA 97(2):722-727 (2000).

Vander Borght, T., et al., "Noninvasive Measurement of Liver Regeneration with Positron Emission Tomography and [2-$^{11}$C]Thymidine," Gastroenterology 101:794-799 (1991).

Vander Borght, T., et al., "Production of [2-$^{11}$C]Thymidine for Quantification of Cellular Proliferation with PET," In. J. Rad. Appl. Istrum. [A] 42:103-104 (1991b).

Vlahos, C. J., et al., "A Specific Inhibitor of Phosphatidylinositol 3-Kinase, 2-(4-Morpholinyl)-8-Phenyl-4H-1-Benzopyran-4-One (LY294002)," J. Biol. Chem. 269(7):5241-5248 (1994).

Wells, P., et al., "Positron Emission Tomography: A New Investigational Area for Cancer Research," Clin. Oncol. 8:7-14 (1996).

Wissner, A., et al., "Synthesis and Structure-Activity Relationshops of 6,7-Disubstituted 4-Anilinoquinoline-3-Carbonitriles. The Design of an Orally Active, Irreversible Inhibitor of the Tyrosine Kinase Activity of the Epidermal Growth Factor Receptor (EGFR) and the Human Epidermal Growth Factor Receptor-2 (HER-2)," J. Med. Chem. 46:49-63 (2003).

Yancopoulos, G. D., et al., "Vascular-Specific Growth Factors and Blood Vessel Formation," Nature 407:242-248 (2000).

Yang, X.D., et al., "Development of ABX-EGF, A Fully Human Anti-EGF Receptor Monoclonal Antibody, for Cancer Therapy," Crit. Rev. Oncol. Hematol. 38:17-23 (2001).

Yang, X.D., et al., "Eradication of Established Tumors By a Fully Human Monoclonal Anitbody to the Epidermal Growth Factor Receptor Without Concomitant Chemotherapy," Cancer Res. 59:1236-1243 (1999).

* cited by examiner

Figure 1

HEAVY CHAINS

SEQ ID NO:2
XPA.10.072
RLQLVQSGAEVRKPGASVKVSCKASGYSFTGHYIHWARQAPGQGLEWMGWINPYSGGTNFPREFQGRVTMTRDTSVNTVYMELTRLTSDDTSVYYCARDHRIVGGLDYW
GQGTLVTVSS
                                        HCDR1                HCDR2                                            HCDR3

SEQ ID NO:4
XPA.10.064
EVQLVQSGAEVRKPGASVKVSCKASGYSFTGHYIHWVRQAPGQGLEWMGWINPYSGGTNFPREFQGRVTMTRDTSVNTVYMELTRLTSDDTSVYYCARDHRIVGGLDYW
GQGTLVTVSS
                                      HCDR1                HCDR2                                            HCDR3

SEQ ID NO:22
XPA.10.064.06
EVQLVQSGAEVRKPGASVKVSCKASGYSFTGHYIHWVRQAPGQGLEWMGWINPYSGGTNFPREFQGRVTMTRDTSVNTVYMELTRLTSDDTSVYYCARDEMTRGGLDY
WGQGTLVTVSS
                                      HCDR1                HCDR2                                            HCDR3

SEQ ID NO:23
XPA.10.064.07
EVQLVQSGAEVRKPGASVKVSCKASGYSFTGHYIHWVRQAPGQGLEWMGWINPYSGGTNFPREFQGRVTMTRDTSVNTVYMELTRLTSDDTSVYYCARDEMHVGGLDY
WGQGTLVTVSS
                                      HCDR1                HCDR2                                            HCDR3

LIGHT CHAINS

SEQ ID NO:3
XPA.10.072
QSVLTQPPSASGTPGQRVTISCSGSGSSSNLGSNFVYWYQQLPGTAPKLLIYRNHQRPSGVPDRFSGSKSGTSASLAISGLRSEDEADYYCASWDDSLRVVVFGGGTKLTVL
                                    LCDR1                      LCDR2                                        LCDR3

SEQ ID NO:5
XPA.10.064
SYVLTQPPSASGTPGQRVTISCSGSGSSNIGINYVYWYQQLPGTAPKLLIYRNDQRPSGVPDRFSGSKSGTSASLAISGLRSEDEADYYCATWDDSLSGVVFGGGTKVTVL
                                    LCDR1                      LCDR2                                        LCDR3

CDRs are in BOLD, and based on the Kabat numbering

Figure 31
A. 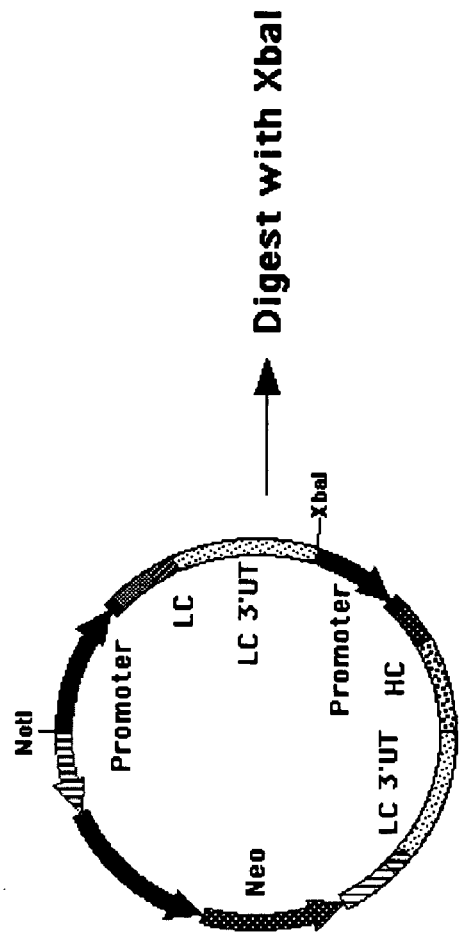
B. 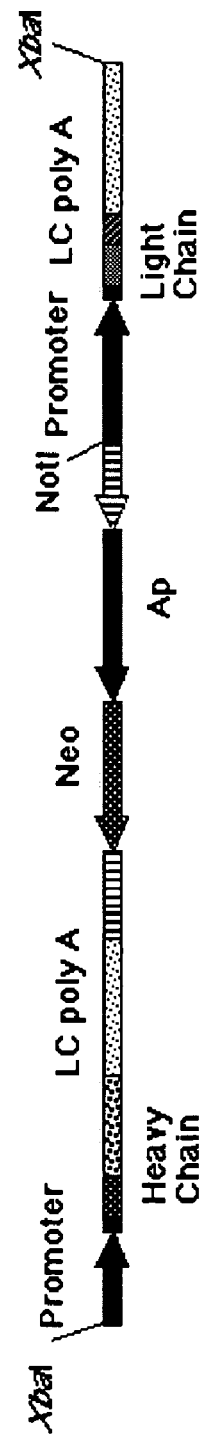

SEQUENCE LISTING

```
<160> NUMBER OF SEQ ID NOS: 29

<210> SEQ ID NO 1
<211> LENGTH: 165
<212> TYPE: PRT
<213> ORGANISM: Homo sapiens

<400> SEQUENCE: 1

Ala Pro Met Ala Glu Gly Gly Gln Asn His His Glu Val Val Lys
1               5                   10                  15

Phe Met Asp Val Tyr Gln Arg Ser Tyr Cys His Pro Ile Glu Thr Leu
                20                  25                  30

Val Asp Ile Phe Gln Glu Tyr Pro Asp Glu Ile Glu Tyr Ile Phe Lys
            35                  40                  45

Pro Ser Cys Val Pro Leu Met Arg Cys Gly Gly Cys Cys Asn Asp Glu
        50                  55                  60

Gly Leu Glu Cys Val Pro Thr Glu Glu Ser Asn Ile Thr Met Gln Ile
65                  70                  75                  80

Met Arg Ile Lys Pro His Gln Gly Gln His Ile Gly Glu Met Ser Phe
                85                  90                  95

Leu Gln His Asn Lys Cys Glu Cys Arg Pro Lys Lys Asp Arg Ala Arg
            100                 105                 110

Gln Glu Asn Pro Cys Gly Pro Cys Ser Glu Arg Arg Lys His Leu Phe
        115                 120                 125

Val Gln Asp Pro Gln Thr Cys Lys Cys Ser Cys Lys Asn Thr Asp Ser
    130                 135                 140

Arg Cys Lys Ala Arg Gln Leu Glu Leu Asn Glu Arg Thr Cys Arg Cys
145                 150                 155                 160

Asp Lys Pro Arg Arg
                165
```

```
<210> SEQ ID NO 2
<211> LENGTH: 119
<212> TYPE: PRT
<213> ORGANISM: Homo sapiens
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 2

Arg Leu Gln Leu Val Gln Ser Gly Ala Glu Val Arg Lys Pro Gly Ala
 1               5                  10                  15

Ser Val Lys Val Ser Cys Lys Ala Ser Gly Tyr Ser Phe Thr Gly His
             20                  25                  30

Tyr Ile His Trp Ala Arg Gln Ala Pro Gly Gln Gly Leu Glu Trp Met
         35                  40                  45

Gly Trp Ile Asn Pro Tyr Ser Gly Gly Thr Asn Phe Pro Arg Glu Phe
 50                  55                  60

Gln Gly Arg Val Thr Met Thr Arg Asp Thr Ser Val Asn Thr Val Tyr
 65                  70                  75                  80

Met Glu Leu Thr Arg Leu Thr Ser Asp Asp Thr Ser Val Tyr Tyr Cys
             85                  90                  95

Ala Arg Asp His Arg Ile Val Gly Gly Leu Asp Tyr Trp Gly Gln Gly
            100                 105                 110

Thr Leu Val Thr Val Ser Ser
            115

<210> SEQ ID NO 3
<211> LENGTH: 110
<212> TYPE: PRT
<213> ORGANISM: Homo sapiens
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (51)..(57)
<223> OTHER INFORMATION: CDR2
<220> FEATURE:
<221> NAME/KEY: MISC_FEATURE
<222> LOCATION: (90)..(100)
<223> OTHER INFORMATION: CDR3

<400> SEQUENCE: 3

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Leu Gly Ser Asn
             20                  25                  30

Phe Val Tyr Trp Tyr Gln Gln Leu Pro Gly Thr Ala Pro Lys Leu Leu
         35                  40                  45

Ile Tyr Arg Asn His Gln Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Ser Trp Asp Ser Leu
```

```
                        85                  90                  95
Arg Val Val Val Phe Gly Gly Gly Thr Lys Leu Thr Val Leu
            100                 105                 110

<210> SEQ ID NO 4
<211> LENGTH: 119
<212> TYPE: PRT
<213> ORGANISM: Homo sapiens
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 4

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp His Arg Ile Val Gly Gly Leu Asp Tyr Trp Gly Gln Gly
            100                 105                 110

Thr Leu Val Thr Val Ser Ser
        115

<210> SEQ ID NO 5
<211> LENGTH: 110
<212> TYPE: PRT
<213> ORGANISM: Homo sapiens
<220> FEATURE:
<221> NAME/KEY: MISC_FEATURE
<222> LOCATION: (23)..(35)
<223> OTHER INFORMATION: CDR1
<220> FEATURE:
<221> NAME/KEY: MISC_FEATURE
<222> LOCATION: (51)..(57)
<223> OTHER INFORMATION: CDR2
<220> FEATURE:
<221> NAME/KEY: MISC_FEATURE
<222> LOCATION: (90)..(100)
<223> OTHER INFORMATION: CDR3

<400> SEQUENCE: 5

Ser Tyr Val Leu Thr Gln Pro Pro Ser Ala Ser Gly Thr Pro Gly Gln
1               5                   10                  15

Arg Val Thr Ile Ser Cys Ser Gly Ser Ser Asn Ile Gly Ile Asn
            20                  25                  30

Tyr Val Tyr Trp Tyr Gln Gln Leu Pro Gly Thr Ala Pro Lys Leu Leu
        35                  40                  45

Ile Tyr Arg Asn Asp Gln Arg Pro Ser Gly Val Pro Asp Arg Phe Ser
    50                  55                  60
```

-continued

```
Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ala Thr Trp Asp Ser Leu
                 85                  90                  95

Ser Gly Val Val Phe Gly Gly Gly Thr Lys Val Thr Val Leu
            100                 105                 110

<210> SEQ ID NO 6
<211> LENGTH: 5
<212> TYPE: PRT
<213> ORGANISM: Homo sapiens

<400> SEQUENCE: 6

Gly His Tyr Ile His
1               5

<210> SEQ ID NO 7
<211> LENGTH: 17
<212> TYPE: PRT
<213> ORGANISM: Homo sapiens

<400> SEQUENCE: 7

Trp Ile Asn Pro Tyr Ser Gly Gly Thr Asn Phe Pro Arg Glu Phe Gln
1               5                   10                  15

Gly

<210> SEQ ID NO 8
<211> LENGTH: 10
<212> TYPE: PRT
<213> ORGANISM: Homo sapiens

<400> SEQUENCE: 8

Asp His Arg Ile Val Gly Gly Leu Asp Tyr
1               5                   10

<210> SEQ ID NO 9
<211> LENGTH: 10
<212> TYPE: PRT
<213> ORGANISM: Homo sapiens

<400> SEQUENCE: 9

Ser Ser Asn Leu Gly Ser Asn Phe Val Tyr
1               5                   10

<210> SEQ ID NO 10
<211> LENGTH: 7
<212> TYPE: PRT
<213> ORGANISM: Homo sapiens

<400> SEQUENCE: 10

Arg Asn His Gln Arg Pro Ser
1               5

<210> SEQ ID NO 11
<211> LENGTH: 11
<212> TYPE: PRT
<213> ORGANISM: Homo sapiens

<400> SEQUENCE: 11

Ala Ser Trp Asp Asp Ser Leu Arg Val Val Val
1               5                   10

<210> SEQ ID NO 12
```

```
<211> LENGTH: 13
<212> TYPE: PRT
<213> ORGANISM: Homo sapiens

<400> SEQUENCE: 12

Ser Gly Ser Ser Ser Asn Ile Gly Ile Asn Tyr Val Tyr
1               5                   10

<210> SEQ ID NO 13
<211> LENGTH: 7
<212> TYPE: PRT
<213> ORGANISM: Homo sapiens

<400> SEQUENCE: 13

Arg Asn Asp Gln Arg Pro Ser
1               5

<210> SEQ ID NO 14
<211> LENGTH: 11
<212> TYPE: PRT
<213> ORGANISM: Homo sapiens

<400> SEQUENCE: 14

Ala Thr Trp Asp Asp Ser Leu Ser Gly Val Val
1               5                   10

<210> SEQ ID NO 15
<211> LENGTH: 10
<212> TYPE: PRT
<213> ORGANISM: Artificial sequence
<220> FEATURE:
<223> OTHER INFORMATION: HCDR3 of affinity matured XPA.10.064

<400> SEQUENCE: 15

Asp Gln Met Val His Gly Gly Leu Asp Tyr
1               5                   10

<210> SEQ ID NO 16
<211> LENGTH: 10
<212> TYPE: PRT
<213> ORGANISM: Artificial sequence
<220> FEATURE:
<223> OTHER INFORMATION: HCDR3 of affinity matured XPA.10.064

<400> SEQUENCE: 16

Asp Glu Met Gln Asn Gly Gly Leu Asp Tyr
1               5                   10

<210> SEQ ID NO 17
<211> LENGTH: 10
<212> TYPE: PRT
<213> ORGANISM: Artificial sequence
<220> FEATURE:
<223> OTHER INFORMATION: HCDR3 of affinity matured XPA.10.064

<400> SEQUENCE: 17

Asp Glu Met Thr Arg Gly Gly Leu Asp Tyr
1               5                   10

<210> SEQ ID NO 18
<211> LENGTH: 10
<212> TYPE: PRT
<213> ORGANISM: Artificial sequence
<220> FEATURE:
<223> OTHER INFORMATION: HCDR3 of affinity matured XPA.10.064

<400> SEQUENCE: 18
```

Asp Glu Met His Val Gly Gly Leu Asp Tyr
1               5                   10

<210> SEQ ID NO 19
<211> LENGTH: 10
<212> TYPE: PRT
<213> ORGANISM: Artificial sequence
<220> FEATURE:
<223> OTHER INFORMATION: HCDR3 of affinity matured XPA.10.064

<400> SEQUENCE: 19

Asp Glu Met Val Trp Gly Gly Leu Asp Tyr
1               5                   10

<210> SEQ ID NO 20
<211> LENGTH: 119
<212> TYPE: PRT
<213> ORGANISM: Artificial sequence
<220> FEATURE:
<223> OTHER INFORMATION: Heavy chain of affinity matured XPA.10.064
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 20

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
                20                  25                  30

Tyr Ile His Trp Val Arg Gln Ala Pro Gly Gln Gly Leu Glu Trp Met
            35                  40                  45

Gly Trp Ile Asn Pro Tyr Ser Gly Gly Thr Asn Phe Pro Arg Glu Phe
50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Gln Met Val His Gly Gly Leu Asp Tyr Trp Gly Gln Gly
            100                 105                 110

Thr Leu Val Thr Val Ser Ser
        115

<210> SEQ ID NO 21
<211> LENGTH: 119
<212> TYPE: PRT
<213> ORGANISM: Artificial sequence
<220> FEATURE:
<223> OTHER INFORMATION: Heavy chain of affinity matured XPA.10.064
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)

<223> OTHER INFORMATION: CDR3

<400> SEQUENCE: 21

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Ser Val Tyr Tyr Cys
                85                  90                  95

Ala Arg Asp Glu Met Gln Asn Gly Gly Leu Asp Tyr Trp Gly Gln Gly
            100                 105                 110

Thr Leu Val Thr Val Ser Ser
            115

<210> SEQ ID NO 22
<211> LENGTH: 119
<212> TYPE: PRT
<213> ORGANISM: Artificial sequence
<220> FEATURE:
<223> OTHER INFORMATION: Heavy chain of affinity matured XPA.10.064
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 22

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Ser Val Tyr Tyr Cys
                85                  90                  95

Ala Arg Asp Glu Met Thr Arg Gly Gly Leu Asp Tyr Trp Gly Gln Gly
            100                 105                 110

Thr Leu Val Thr Val Ser Ser
            115

<210> SEQ ID NO 23
<211> LENGTH: 119
<212> TYPE: PRT
<213> ORGANISM: Artificial sequence
<220> FEATURE:

-continued

<223> OTHER INFORMATION: Heavy chain of affinity matured XPA.10.064
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 23

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

Ala Arg Asp Glu Met His Val Gly Gly Leu Asp Tyr Trp Gly Gln Gly
            100                 105                 110

Thr Leu Val Thr Val Ser Ser
        115

<210> SEQ ID NO 24
<211> LENGTH: 119
<212> TYPE: PRT
<213> ORGANISM: Artificial sequence
<220> FEATURE:
<223> OTHER INFORMATION: Heavy chain of affinity matured XPA.10.064
<220> FEATURE:
<221> NAME/KEY: MISC_FEATURE
<222> LOCATION: (31)..(35)
<223> OTHER INFORMATION: CDR1
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (99)..(108)
<223> OTHER INFORMATION: CDR3

<400> SEQUENCE: 24

Glu Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Gly His
            20                  25                  30

Tyr Ile His Trp Val Arg Gln Ala Pro Gly Gln Gly Leu Glu Trp Met
        35                  40                  45

Gly Trp Ile Asn Pro Tyr Ser Gly Gly Thr Asn Phe Pro Arg Glu Phe
    50                  55                  60

Gln Gly Arg Val Thr Met Thr Arg Asp Thr Ser Val Asn Thr Val Tyr
65                  70                  75                  80

Met Glu Leu Thr Arg Leu Thr Ser Asp Asp Thr Ser Val Tyr Tyr Cys
                85                  90                  95

```
Ala Arg Asp Glu Met Val Trp Gly Gly Leu Asp Tyr Trp Gly Gln Gly
            100                 105                 110

Thr Leu Val Thr Val Ser Ser
        115

<210> SEQ ID NO 25
<211> LENGTH: 10
<212> TYPE: PRT
<213> ORGANISM: Artificial sequence
<220> FEATURE:
<223> OTHER INFORMATION: HCDR3 of affinity matured XPA.10.064 w/
      additional AA substitution

<400> SEQUENCE: 25

Asp Glu Ala Thr Arg Gly Gly Leu Asp Tyr
1               5                   10

<210> SEQ ID NO 26
<211> LENGTH: 10
<212> TYPE: PRT
<213> ORGANISM: Artificial sequence
<220> FEATURE:
<223> OTHER INFORMATION: HCDR3 of affinity matured XPA.10.064 w/
      additional AA substitution

<400> SEQUENCE: 26

Asp Glu Lys Thr Arg Gly Gly Leu Asp Tyr
1               5                   10

<210> SEQ ID NO 27
<211> LENGTH: 10
<212> TYPE: PRT
<213> ORGANISM: Artificial sequence
<220> FEATURE:
<223> OTHER INFORMATION: HCDR3 of affinity matured XPA.10.064 w/
      additional AA substitution

<400> SEQUENCE: 27

Asp Glu Pro Thr Arg Gly Gly Leu Asp Tyr
1               5                   10

<210> SEQ ID NO 28
<211> LENGTH: 10
<212> TYPE: PRT
<213> ORGANISM: Artificial sequence
<220> FEATURE:
<223> OTHER INFORMATION: HCDR3 of affinity matured XPA.10.064 w/
      additional AA substitution

<400> SEQUENCE: 28

Asp Glu Thr Thr Arg Gly Gly Leu Asp Tyr
1               5                   10

<210> SEQ ID NO 29
<211> LENGTH: 10
<212> TYPE: PRT
<213> ORGANISM: Artificial sequence
<220> FEATURE:
<223> OTHER INFORMATION: HCDR3 of affinity matured XPA.10.064 w/
      additional AA substitution

<400> SEQUENCE: 29

Asp Glu Leu Thr Arg Gly Gly Leu Asp Tyr
1               5                   10
```

FULLY HUMAN ANTI-VEGF ANTIBODIES AND METHODS OF USING

RELATED APPLICATIONS

The present application is a national stage application, filed under 35 U.S.C. §371, of International Application No. PCT/US08/80531, filed Oct. 20, 2008, which claims priority to U.S. Provisional Application No. 60/981,808, filed Oct. 22, 2007, and to U.S. Provisional Application No. 61/046,370, filed Apr. 18, 2008. The disclosures of these applications are hereby incorporated by reference herein in their entirety, including drawings.

BACKGROUND

The vascular endothelial growth factors (VEGFs) are a major family of angiogenic proteins involved in endothelial cell activation, proliferation, and survival, particularly during retinal proliferative diseases and tumorigenesis. VEGFs belong to the VEGF-PDGF (platelet-derived growth factor) super-gene family, and are small glycoprotein dimers that bind receptors expressed on vascular and lymphatic endothelial cells. There are currently seven known ligands in the VEGF family: VEGF-A (VEGF), VEGF-B, VEGF-C, VEGF-D, VEGF-E (viral-derived), and placental growth factor (PlGF)-1 and -2. These VEGF ligands mediate their effects by binding to one or more of the three known VEGF receptors (VEGF-Rs), each of which possess receptor tyrosine kinase activity. VEGF-R1 (Flt-1) is predominantly expressed on endothelial cells and monocytes, binds VEGF and VEGF-B, and appears to mediate endothelial and monocyte migration. VEGF-R2 (i.e., human KDR or murine Flk-1) is mainly expressed on endothelial cells, is selective for VEGF (and particular fragments of VEGF-C and VEGF-D), and mediates VEGF-induced endothelial cell proliferation, survival, and migration, as well as vascular permeability. VEGF-R3 (Flt-4) is mainly expressed on lymphatic endothelial cells and binds VEGF-C and VEGF-D to promote lymphangiogenesis. VEGF-R1, -R2, and -R3 are each expressed on some tumor cells. Binding of VEGF to the VEGF receptors triggers receptor dimerization, leading to subsequent receptor activation and signal transduction. VEGF binding to VEGF-R2 initiates a signal transduction pathway that is dominant in promoting angiogenesis. This pathway involves receptor activation with subsequent induction of intracellular signaling. Receptor activation in this case entails three basic events: (i) VEGF binding to VEGF-R2, (ii) receptor dimerization, and (iii) receptor autophosphorylation (and hence activation) of the receptor tyrosine kinase. Intracellular messengers such as phospholipase C and phosphatidylinositol-3-kinase bind directly to the autophosphorylated form of VEGF-R2 and become phosphorylated by the receptor tyrosine kinase, which subsequently triggers an intracellular cascade of signaling events leading to nuclear signals that ultimately promote cell proliferation, migration, and survival (anti-apoptosis), and increase vascular permeability.

Aberrant angiogenesis is associated with a variety of disease states, including cancer (Holash 2002). VEGF signaling has been verified to play a role in both normal vascular development and the pathologic angiogenesis associated with various diseases (Erikkson 1999; Ferrara 1999; Yancopoulos 2000). VEGF promotes vascular endothelial cell growth and increases vascular permeability (Ferrara 2004).

Previous studies have revealed elevated VEGF expression levels in a majority of tumor types (Berkman 1993; Brown 1993; Brown 1995; Dvorak 1995; Mattern 1996). Studies have also revealed increased VEGF levels in subjects with ocular angiogenic diseases such as wet AMD. Wet AMD accounts for only around 10% of total AMD cases, but causes approximately 90% of blindness arising from AMD. Wet AMD is characterized by choroidal neovascularization (CNV), the development of abnormal blood vessels beneath the retinal pigment epithelium layer of the retina. VEGF-A is believed to play a major role in the formation of these vessels, which leak beneath the macula and cause retinal distortion and vision deterioration.

Therapeutic anti-VEGF antibodies are currently available. For example, the humanized IgG1 monoclonal antibody Bevacizumab (a.k.a., Avastin®, sold by Genentech, San Francisco, Calif.; also referred to herein as BM-1) binds human VEGF with an affinity ($K_D$) of approximately 500 pM. While Bevacizumab has been used to treat a variety of cancers, there is a need in the art for antibodies with greater in vivo efficacy. Such antibodies present significant technical challenges and are highly elusive because merely increasing the binding affinity of a VEGF antibody does not necessarily increase its in vivo efficacy (Liang 2006).

SUMMARY

The present application addresses the need for VEGF antibodies with superior efficacy. Provided herein are therapeutic antibodies and antigen-binding fragments thereof, and compositions and methods of use for treating medical conditions such as cancer.

In certain embodiments, an antibody or antigen-binding fragment is provided that comprises an HCDR3 region selected from the group consisting of the HCDR3 of XPA.10.064, XPA.10.072, XPA.10.064.03, XPA.10.064.04, XPA.10.064.06, XPA.10.064.07, and XPA.10.064.10. In certain embodiments, the antibody or antigen-binding fragment further comprises the HCDR1 and/or HCDR2 of XPA.10.064 or XPA.10.072.

In certain embodiments an antibody or antigen-binding fragment is provided that comprises LCDR1, LCDR2, and LCDR3 of XPA.10.072; LCDR1, LCDR2, and LCDR3 of XPA.10.064; HCDR1, HCDR2, and HCDR3 of XPA.10.072; HCDR1, HCDR2, and HCDR3 of XPA.10.064; HCDR1, HCDR2, and HCDR3 of XPA.10.064.03; HCDR1, HCDR2, and HCDR3 of XPA.10.064.04; HCDR1, HCDR2, and HCDR3 of XPA.10.064.06; HCDR1, HCDR2, and HCDR3 of XPA.10.064.07; and/or HCDR1, HCDR2, and HCDR3 of XPA.10.064.10. In certain embodiments, the antibody or antigen-binding fragment comprises the heavy chain of XPA.10.072, XPA.10.064, XPA.10.064.03, XPA.10.064.04, XPA.10.064.06, XPA.10.064.07, or XPA.10.064.10. In certain embodiments, the antibody or antigen-binding fragment comprises the light chain of XPA.10.064 or XPA.10.072.

In certain embodiments, an antibody or antigen-binding fragment is provided that comprises a heavy chain variable region comprising an amino acid sequence selected from the group consisting of SEQ ID NO:15, SEQ ID NO:16, SEQ ID NO:17, SEQ ID NO:18, and SEQ ID NO:19. In certain of these embodiments, the heavy chain variable region further comprises one or more of the amino acid sequences set forth in SEQ ID NO:6 and/or SEQ ID NO:7. In certain embodiments, the antibodies or antigen-binding fragments comprise a heavy chain comprising an amino acid sequence selected from the group consisting of SEQ ID NO:20, SEQ ID NO:21, SEQ ID NO:22, SEQ ID NO:23, and SEQ ID NO:24. In certain embodiments, the antibody or antigen-binding fragment further comprises a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain of these embodiments, the antibodies or antigen-binding fragments comprise a light chain comprising the amino acid sequence set forth in SEQ ID NO:5 or SEQ ID NO:3.

In certain embodiments, an antibody or antigen-binding fragment is provided that comprises a heavy chain variable region comprising the amino acid sequence set forth in SEQ ID NO:17 and a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain embodiments, the heavy chain variable region of this antibody or antigen-binding fragment further comprises the amino acid sequences set forth in SEQ ID NO:6 and/or SEQ ID NO:7, and in certain of these embodiments, the antibody or antigen-binding fragment comprises a heavy chain comprising the amino acid sequence set forth in SEQ ID NO:22 and a light chain comprising the amino acid sequence set forth in SEQ ID NO:5.

In certain embodiments, an antibody or antigen-binding fragment is provided that comprises a heavy chain variable region comprising the amino acid sequence set forth in SEQ ID NO:18 and a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain embodiments, the heavy chain variable region of this antibody or antigen-binding fragment further comprises the amino acid sequences set forth in SEQ ID NO:6 and/or SEQ ID NO:7, and in certain of these embodiments, the antibody or antigen-binding fragment comprises a heavy chain comprising the amino acid sequence set forth in SEQ ID NO:23 and a light chain comprising the amino acid sequence set forth in SEQ ID NO:5.

In certain embodiments, an antibody or antigen-binding fragment is provided that comprises a heavy chain variable region comprising the amino acid sequence set forth in SEQ ID NO:15 and a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain embodiments, the heavy chain variable region of this antibody or antigen-binding fragment further comprises the amino acid sequences set forth in SEQ ID NO:6 and/or SEQ ID NO:7, and in certain of these embodiments, the antibody or antigen-binding fragment comprises a heavy chain comprising the amino acid sequence set forth in SEQ ID NO:20 and a light chain comprising the amino acid sequence set forth in SEQ ID NO:5.

In certain embodiments, an antibody or antigen-binding fragment is provided that comprises a heavy chain variable region comprising the amino acid sequence set forth in SEQ ID NO:16 and a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain embodiments, the heavy chain variable region of this antibody or antigen-binding fragment further comprises the amino acid sequences set forth in SEQ ID NO:6 and/or SEQ ID NO:7, and in certain of these embodiments, the antibody or antigen-binding fragment comprises a heavy chain comprising the amino acid sequence set forth in SEQ ID NO:21 and a light chain comprising the amino acid sequence set forth in SEQ ID NO:5.

In certain embodiments, an antibody or antigen-binding fragment is provided that comprises a heavy chain variable region comprising the amino acid sequence set forth in SEQ ID NO:19 and a light chain variable region comprising one or more of the amino acid sequences set forth in SEQ ID NO:12, SEQ ID NO:13, SEQ ID NO:14, SEQ ID NO:9, SEQ ID NO:10, and SEQ ID NO:11. In certain embodiments, the heavy chain variable region of this antibody or antigen-binding fragment further comprises the amino acid sequences set forth in SEQ ID NO:6 and/or SEQ ID NO:7, and in certain of these embodiments, the antibody or antigen-binding fragment comprises a heavy chain comprising the amino acid sequence set forth in SEQ ID NO:24 and a light chain comprising the amino acid sequence set forth in SEQ ID NO:5.

In certain embodiments, an antibody or antigen-binding fragment is provided that specifically binds VEGF and has one or more of the following properties: 1) $K_D$ for binding to $hVEGF_{165}$ of about $10^{-10}$ M; 2) $k_a$ for binding to $hVEGF_{165}$ of about $1.89 \times 10^5$; 3) $k_d$ for binding to $hVEGF_{165}$ of about $1.73 \times 10^{-5}$; 4) binding affinity for $hVEGF_{165}$ that is about 4.25 times greater than the binding affinity of Bevacizumab for $hVEGF_{165}$; 5) inhibits HUVEC cell proliferation with an $IC_{50}$ of about 154 pM; 6) inhibits HUVEC cell proliferation with an $IC_{50}$ about 56% that of Bevacizumab; 7) $K_D$ for binding to $hVEGF_{165}$ in the range of about $1.97 \times 10^{-10}$ M to about $3.49 \times 10^{-11}$ M; 8) $k_a$ for binding to $hVEGF_{165}$ in the range of about $1.5 \times 10^5$ to about $2.16 \times 10^5$ M; 9) $k_d$ for binding to $hVEGF_{165}$ in the range of about $6.65 \times 10^{-6}$ to about $2.94 \times 10^{-5}$ M; 10) inhibits HUVEC cell proliferation with an $IC_{50}$ in the range of about 129 pM to about 174 pM; 11) binding affinity for hVEGF that is at least about 10 times greater than the affinity of the antibody or antigen-binding fragment thereof for mVEGF; 12) competes with Bevacizumab for binding to $hVEGF_{165}$; 13) inhibits tumor growth as a function of percent tumor growth inhibition to the same or a greater degree than Bevacizumab when administered at the same or a lower dosage; and 14) delays tumor growth to a specified size for a greater duration than Bevacizumab when administered at the same or a lower dosage as Bevacizumab. In certain embodiments, an antibody or antigen-binding fragment is provided that binds to the same epitope on $hVEGF_{165}$ as an antibody comprising the amino acid sequence set forth in SEQ ID NO:8, SEQ ID NO:15, SEQ ID NO:16, SEQ ID NO:17, SEQ ID NO:18, or SEQ ID NO:19. In certain of these embodiments, the antibody or antigen-binding fragment binds the same epitope on $hVEGF_{165}$ as an antibody comprising the amino acid sequence set forth in SEQ ID NO:2, SEQ ID NO:3, SEQ ID NO:4, SEQ ID NO:5, SEQ ID NO:20, SEQ ID NO:21, SEQ ID NO:22, SEQ ID NO:23, or SEQ ID NO:24.

In certain embodiments, the antibodies or antigen-binding fragments bind $hVEGF_{165}$ with a $K_D$ of $\leq 200$ pM. In certain of these embodiments, the antibodies or antigen-binding fragments bind $hVEGF_{165}$ with a $K_D$ of $\leq 150$ pM, in other embodiments 100 pM, and in still other embodiments $\leq 50$ pM. In certain embodiments, the antibodies or antigen-binding fragments provided herein that bind an epitope on $hVEGF_{165}$ that overlaps at least partially with the epitope bound by Bevacizumab.

In certain embodiments, the antibodies or antigen-binding fragments provided herein block binding of $hVEGF_{165}$ to a VEGF receptor, which in certain embodiments is VEGF-R1 or VEGF-R2. In certain embodiments, the antibodies or antigen-binding fragments inhibit $hVEGF_{165}$-induced phosphorylation of a VEGF receptor. In certain embodiments, the antibodies or antigen-binding fragments binds $hVEGF_{165}$ with a $K_D$ that is at least 10-fold greater (i.e., at least ten-fold greater affinity, meaning at least 10-fold lower in number) than the $K_D$ with which they bind $mVEGF_{165}$. In certain of these embodiments, the antibodies or antigen-binding fragments bind $hVEGF_{165}$ with a $K_D$ at least 50-fold greater than the $K_D$ with which they bind $mVEGF_{165}$, and in certain embodiments at least 100-fold greater.

In certain of the above embodiments, the antibodies or antigen-binding fragments disclosed herein comprise a κ light chain, a γ1 heavy chain, a γ2 heavy chain, a γ3 heavy chain, or a γ4 heavy chain constant region. In certain of these embodiments, the antibodies or antigen-binding fragments comprise an IgG2 constant region. In certain embodiments, the antibodies disclosed herein are full antibodies. In certain of these embodiments, the antibody may be a monoclonal antibody, polyclonal antibody, recombinant antibody, bispecific antibody, humanized antibody, chimeric antibody, labeled antibody, bivalent antibody, anti-idiotypic antibody, or fully human antibody. In certain embodiments, an antibody or antigen-binding fragment as provided herein may be a camelized single domain antibody, a diabody, a scFv, an scFv dimer, a dsFv, a $(dsFv)_2$, a dsFv-dsFv', an Fv fragment, a Fab, a Fab', a $F(ab')_2$, a ds diabody, a nanobody, a domain antibody, or a bivalent domain antibody.

In certain embodiments, methods are provided for inhibiting angiogenesis in a subject in need thereof by administering to said subject a therapeutically effective amount of one or more antibodies or antigen-binding fragments disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain embodiments, the antibody or antigen-binding fragment is administered at a dosage of 5 mg/kg or less per administration. In certain of these embodiments, the antibody or antigen-binding fragment is administered at a dosage of 1 mg/kg or less per administration, in other embodiments 0.5 mg/kg or less, and in still other embodiments 0.1 mg/kg or less. In certain embodiments, the antibody or antigen-binding fragment is administered to the subject multiple times at an interval of once a day to once every two months. In certain of these embodiments, the antibody or antigen-binding fragment may be administered about once a week, about once every two weeks, about once a month, or about once every two months.

In certain embodiments, methods are provided for treating a disease associated with aberrant angiogenesis in a subject (e.g., a mammalian subject such as a human, primate, canine, rat, rabbit, or mouse) in need thereof comprising administering to said subject a therapeutically effective amount of one or more antibodies or antigen-binding fragments disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain embodiments, the antibody or antigen-binding fragment is administered at a dosage of 5 mg/kg or less per administration. In certain of these embodiments, the antibody or antigen-binding fragment is administered at a dosage of 1 mg/kg or less per administration, in other embodiments 0.5 mg/kg or less, and in still other embodiments 0.1 mg/kg or less. In certain embodiments, the antibody or antigen-binding fragment is administered to the subject multiple times at an interval of once a day to once every two months. In certain of these embodiments, the antibody or antigen-binding fragment may be administered about once a week, about once every two weeks, about once a month, or about once every two months.

In certain embodiments, methods are provided for treating an inflammatory disease associated with VEGF signaling in a subject (e.g., a mammalian subject such as a human, primate, canine, rat, rabbit, or mouse) in need thereof comprising administering to said subject a therapeutically effective amount of one or more antibodies or antigen-binding fragments disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain embodiments, the disease associated with VEGF signaling is rheumatoid arthritis, psoriasis, scleroderma, chronic obstructive pulmonary disease, or asthma. In certain embodiments, the antibody or antigen-binding fragment is administered at a dosage of 5 mg/kg or less per administration. In certain of these embodiments, the antibody or antigen-binding fragment is administered at a dosage of 1 mg/kg or less per administration, in other embodiments 0.5 mg/kg or less, and in still other embodiments 0.1 mg/kg or less. In certain embodiments, the antibody or antigen-binding fragment is administered to the subject multiple times at an interval of once a day to once every two months. In certain of these embodiments, the antibody or antigen-binding fragment may be administered about once a week, about once every two weeks, about once a month, or about once every two months.

In certain embodiments, methods are provided for treating wet acute macular degeneration or diabetic retinopathy in a subject (e.g., a mammalian subject such as a human, primate, canine, rat, rabbit, or mouse) in need thereof comprising administering to said subject a therapeutically effective amount of one or more antibodies or antigen-binding fragments disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain embodiments, the antibody or antigen-binding fragment is administered at a dosage of 5 mg/kg or less per administration. In certain of these embodiments, the antibody or antigen-binding fragment is administered at a dosage of 1 mg/kg or less per administration, in other embodiments 0.5 mg/kg or less, and in still other embodiments 0.1 mg/kg or less. In certain embodiments, the antibody or antigen-binding fragment is administered to the subject multiple times at an interval of once a day to once every two months. In certain of these embodiments, the antibody or antigen-binding fragment may be administered about once a week, about once every two weeks, about once a month, or about once every two months.

In certain embodiments, methods are provided for treating a cancer associated with increased VEGF signaling in a subject (e.g., a mammalian subject such as a human, primate, canine, rat, rabbit, or mouse) in need thereof comprising administering to said subject a therapeutically effective amount of one or more antibodies or antigen-binding fragments disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain of these embodiments, the antibody or antigen-binding fragment further comprises a conjugate that is either a toxin, cytokine, or chemotherapeutic agent. In certain embodiments, the antibody or antigen-binding fragment is administered in combination with or linked to one or more chemotherapeutic agents. In certain embodiments, the subject is subjected to one or more additional therapeutic procedures such as surgical tumorectomy or anti-cancer radiation therapy. In certain embodiments, the antibody or antigen-binding fragment is administered at a dosage of 5 mg/kg or less per administration. In certain of these embodiments, the antibody or antigen-binding fragment is administered at a dosage of 1 mg/kg or less per administration, in other embodiments 0.5 mg/kg or less, and in still other embodiments 0.1 mg/kg or less. In certain embodiments, the antibody or antigen-binding fragment is administered to the subject multiple times at an interval of once a day to once every two months. In certain of these embodiments, the antibody or antigen-binding fragment may be administered about once a week, about once every two weeks, about once a month, or about once every two months.

In certain embodiments, a kit is provided comprising one or more antibodies or antigen-binding fragments as disclosed herein. In certain of these embodiments, the antibody or antigen-binding fragment comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5. In certain embodiments, the kit further comprises instructions for using the antibodies or antigen-binding fragments and/or for utilizing other components of the kit.

In certain embodiments, polynucleotides are provided that encode the amino acid sequences set forth in SEQ ID NOs: 2-24. In certain other embodiments, vectors are provided that comprise these polynucleotides, and in certain other embodiments, host cells are provided that comprises these vectors. In certain embodiments, methods are provided for expressing one or more of the antibodies or antigen-binding fragments disclosed herein by culturing these host cells under conditions in which polynucleotides encoding the antibodies or antigen-binding fragments are expressed from a vector. In certain embodiments, the polynucleotides provided herein are operably associated with a promoter such as a CMV promoter in a vector. In certain embodiments, host cells comprising the vectors provided herein are Chinese hamster ovary cell.

In certain embodiments, pharmaceutical compositions are provided that comprise one or more antibodies or antigen-binding fragments as disclosed herein. In certain of these embodiments, the composition further comprises one or more physiologically tolerable components. In certain of these embodiments, the one or more physiologically tolerable components may be one or more pharmaceutically acceptable carriers, diluents, adjuvants, excipients, or non-toxic auxiliary substances. In certain of these embodiments, the one or more physiologically tolerable components may comprise one or more antioxidants, which may be selected from methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. Likewise, in certain embodiments methods are provided for inhibiting oxidation and/or preventing degradation of VEGF binding affinity of the antibodies or antigen-binding fragments thereof provided herein using one or more antioxidants. In certain embodiments, the antibody or antigen-binding fragment for use in the composition comprises a heavy chain variable region comprising the amino acid sequence set forth in SEQ ID NO:22 and a light chain variable region comprising the amino acid sequence set forth in SEQ ID NO:5. In other embodiments, the antibody or antigen-binding fragment comprises a heavy chain variable region comprising the amino acid sequence set forth in SEQ ID NOs:20, 21, 23, or 24 and a light chain variable region comprising the amino acid sequence set forth in SEQ ID NO:5.

In certain embodiments, the use of one or more antibodies or antigen-binding fragments as provided herein in the manufacture of a medicament for treating a disease associated with aberrant angiogenesis, an inflammatory disease associated with aberrant angiogenesis, an inflammatory disease associated with VEGF signaling, wet acute macular degeneration, diabetic retinopathy, or cancer associated with increased VEGF signaling is provided.

In certain embodiments, the antibodies or antigen-binding fragments disclosed herein are provided for use in the treatment of a disease associated with aberrant angiogenesis, an inflammatory disease associated with aberrant angiogenesis, an inflammatory disease associated with VEGF signaling, wet acute macular degeneration, diabetic retinopathy, or cancer associated with VEGF signaling (e.g., a cancer exhibiting increased VEGF signaling relative to non-cancerous cells) is provided.

BRIEF DESCRIPTION OF THE DRAWINGS

FIG. 1: Heavy chain variable regions (including HCDRs) and light chain variable regions (including LCDRs) of XPA.10.064 and XPA.10.072

FIG. 31: Structure of the XPA.10.064 heavy chain plus light chain vector pMXSP117. The XPA.10.064 heavy chain plus light chain vector pMXSP119 has the same structure, but with the hisD gene instead of the neo gene. A. Circular structure. B. Linearized structure following digestion with XbaI.

DETAILED DESCRIPTION

Figure 2:
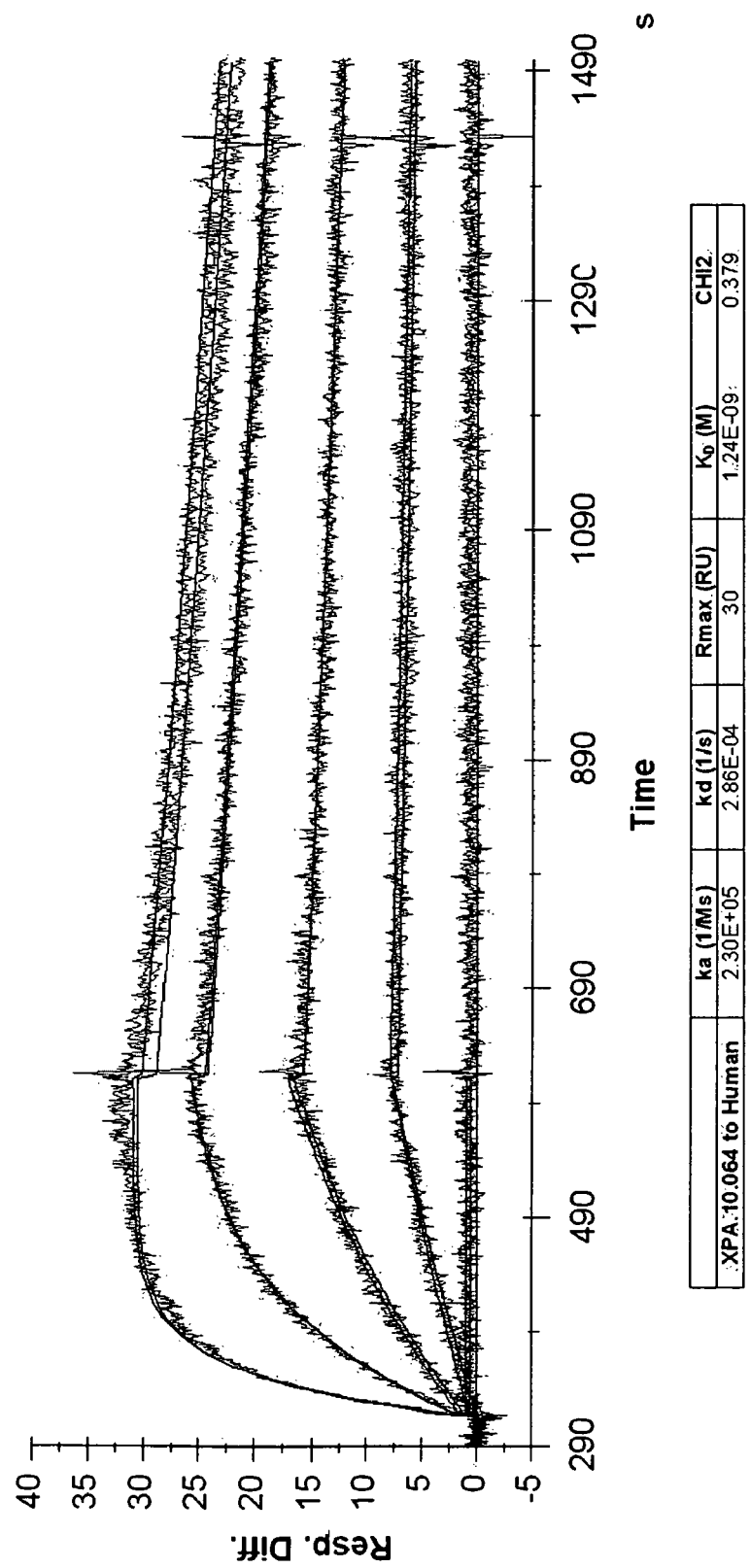
FIG. 2: Biacore analysis of XPA.10.064 IgG2 binding to $hVEGF_{165}$.

The following description of the invention is merely intended to illustrate various embodiments of the invention. As such, the specific modifications discussed are not to be construed as limitations on the scope of the invention. It will be apparent to one skilled in the art that various equivalents, changes, and modifications may be made without departing from the scope of the invention, and it is understood that such equivalent embodiments are to be included herein.

ABBREVIATIONS

The following abbreviations are used herein: ADCC, antibody-dependent cellular cytotoxicity; AMD, age-related macular degeneration; BDS, bulk drug substance; BM-1, Bevacizumab; CDC, complement-dependent cytotoxicity; CNV, choroidal neovascularization; COPD, chronic obstructive pulmonary disease; DF, diafiltration; EDTA, ethylenediaminetetraacetic acid; GMP, Good Manufacturing Practices; HAMA, human anti-mouse antibodies; HIC, hydrophobic interaction chromatography; HUVEC, human umbilical vein endothelial cell; hVEGF, human VEGF; MCB, Master Cell Bank; mpk, mg/kg; mVEGF, murine VEGF; PD, pharmacodynamics; PK, pharmacokinetics; RA, rheumatoid arthritis; RIA, radioimmunoprecipitation; UF, ultrafiltration; VEGF, vascular endothelial growth factor; VEGF-R, vascular endothelial growth factor receptor; VHL, von Hippel/Lindau; X-reactivity, cross-reactivity.

DEFINITIONS

The term "antibody" as used herein includes any monoclonal antibody, polyclonal antibody, multispecific antibody, or bispecific (bivalent) antibody that binds to a specific antigen. A complete antibody comprises two heavy chains and two light chains. Each heavy chain consists of a variable region and a first, second, and third constant region, while each light chain consists of a variable region and a constant region. Mammalian heavy chains are classified as α, δ, ε, γ, and μ, and mammalian light chains are classified as γ or κ. The antibody has a "Y" shape, with the stem of the Y consisting of the second and third constant regions of two heavy chains bound together via disulfide bonding. Each arm of the Y includes the variable region and first constant region of a single heavy chain bound to the variable and constant regions of a single light chain. The variable regions of the light and heavy chains are responsible for antigen binding. The variables region in both chains generally contain three highly variable loops called the complementarity determining regions (CDRs) (light (L) chain CDRs including LCDR1, LCDR2, and LCDR3, heavy (H) chain CDRs including HCDR1, HCDR2, HCDR3). CDR boundaries for the antibodies and antigen-binding fragments disclosed herein may be defined or identified by the conventions of Kabat, Chothia, or Al-Lazikani (Al-Lazikani 1997; Chothia 1985; Chothia 1987; Chothia 1989; Kabat 1987; Kabat 1991). The three CDRs are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and μ heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α1 heavy chain).

An antibody or antigen-binding fragment thereof that is "bivalent" comprises two antigen-binding sites. The two antigen binding sites may bind to the same antigen, or they may each bind to a different antigen, in which case the antibody or antigen-binding fragment is characterized as "bispecific."

The term "antigen-binding fragment" as used herein refers to an antibody fragment such as for example a diabody, a Fab, a Fab', a F(ab')$_2$, an Fv fragment, a disulfide stabilized Fv fragment (dsFv), a (dsFv)$_2$, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody binds. In certain embodiments, an antigen-binding fragment may comprise one or more CDRs from a particular human antibody grafted to a framework region from one or more different human antibodies.

"Fab" with regard to an antibody refers to that portion of the antibody consisting of a single light chain (both variable and constant regions) bound to the variable region and first constant region of a single heavy chain by a disulfide bond.

"Fab'" refers to a Fab fragment that includes a portion of the hinge region.

"F(ab')$_2$" refers to a dimer of Fab.

"Fc" with regard to an antibody refers to that portion of the antibody consisting of the second and third constant regions of a first heavy chain bound to the second and third constant regions of a second heavy chain via disulfide bonding. The Fc portion of the antibody is responsible for various effector functions such as ADCC, and CDC, but does not function in antigen binding.

"Fv" with regard to an antibody refers to the smallest fragment of the antibody to bear the complete antigen binding site. An Fv fragment consists of the variable region of a single light chain bound to the variable region of a single heavy chain.

"Single-chain Fv antibody" or "scFv" refers to an engineered antibody consisting of a light chain variable region and a heavy chain variable region connected to one another directly or via a peptide linker sequence (Houston 1988).

"Single-chain Fv-Fc antibody" or "scFv-Fc" refers to an engineered antibody consisting of a scFv connected to the Fc region of an antibody.

"Camelized single domain antibody," "heavy chain antibody," or "HCAb" refers to an antibody that contains two $V_H$ domains and no light chains (Riechmann 1999; Muyldermans 2001; WO94/04678; WO94/25591; U.S. Pat. No. 6,005,079). Heavy chain antibodies were originally derived from Camelidae (camels, dromedaries, and llamas). Although devoid of light chains, camelized antibodies have an authentic antigen-binding repertoire (Hamers-Casterman 1993; Nguyen 2002; Nguyen 2003). The variable domain of a heavy chain antibody (VHH domain) represents the smallest known antigen-binding unit generated by adaptive immune responses (Koch-Nolte 2007).

A "nanobody" refers to an antibody fragment that consists of a VHH domain from a heavy chain antibody and two constant domains, CH2 and CH3.

"Diabodies" include small antibody fragments with two antigen-binding sites, wherein the fragments comprise a $V_H$ domain connected to a $V_L$ domain in the same polypeptide chain ($V_H$-$V_L$ or $V_H$-$V_L$) (see, e.g., Holliger 1993; EP404097; WO93/11161). By using a linker that is too short to allow pairing between the two domains on the same chain, the domains are forced to pair with the complementary domains of another chain, thereby creating two antigen-binding sites.

A "domain antibody" refers to an antibody fragment containing only the variable region of a heavy chain or the variable region of a light chain. In certain instances, two or more $V_H$ domains are covalently joined with a peptide linker to create a bivalent domain antibody. The two $V_H$ domains of a bivalent domain antibody may target the same or different antigens.

In certain embodiments, a "(dsFv)$_2$" comprises three peptide chains: two $V_H$ moieties linked by a peptide linker and bound by disulfide bridges to two $V_L$ moieties.

In certain embodiments, a "bispecific ds diabody" comprises $V_{H1}$-$V_{L2}$ (linked by a peptide linker) bound to $V_{L1}$-$V_{H2}$ (also linked by a peptide linker) via a disulfide bridge between $V_{H1}$ and $V_{L1}$.

In certain embodiments, a "bispecific dsFv" or dsFv-dsFv'" comprises three peptide chains: a $V_{H1}$-$V_{H2}$ moiety wherein the heavy chains are linked by a peptide linker (e.g., a long flexible linker) and bound to $V_{L1}$ and $V_{L2}$ moieties, respectively, via disulfide bridges, wherein each disulfide paired heavy and light chain has a different antigen specificity.

In certain embodiments, an "scFv dimer" is a bivalent diabody comprising $V_H$-$V_L$ (linked by a peptide linker) dimerized with another $V_H$-$V_L$ moiety such that $V_H$'s of one moiety coordinate with the $V_L$'s of the other moiety and form two identical binding sites. In other embodiments, an "scFv dimer" is a bispecific diabody comprising $V_{H1}$-$V_{L2}$ (linked by a peptide linker) associated with $V_{L1}$-$V_{H2}$ (also linked by a peptide linker) such that $V_{H1}$ and $V_{L1}$ coordinate and $V_{H2}$ and $V_{L2}$ coordinate and each coordinated pair has a different antigen specificity.

The term "epitope" as used herein refers to the specific group of atoms or amino acids on an antigen to which an antibody binds. Two antibodies may bind the same epitope within an antigen if they exhibit competitive binding for the antigen. For example, if an antibody or antigen-binding fragment as disclosed herein competes with Bevacizumab for VEGF binding, the antibody may be, but is not necessarily, considered to bind the same epitope as Bevacizumab.

"VEGF" or "VEGF ligand" as used herein refers to one of the seven currently known VEGF ligands: VEGF-A, VEGF-B, VEGF-C, VEGF-D, VEGF-E (viral-derived), or placental growth factor (PlGF)-1 or -2. With regard to VEGF-A, there are currently four known splicing isoforms, with each demonstrating unique biological functions. The 165 amino acid isoform (VEGF$_{165}$, SEQ ID NO:1) exists in both heparin-bound and soluble forms. The 121 amino acid isoform (VEGF$_{121}$), which is missing a fragment corresponding to the region between residues 115 and 159 of VEGF$_{165}$, exists in soluble form only. The longer 189 and 206 amino acid isoforms (VEGF$_{189}$ and VEGF$_{206}$, respectively) retain the ability to bind heparin. The antibodies and antigen-binding fragments provided herein exhibit high binding affinity for hVEGF$_{165}$, but in certain embodiments may cross-react or exhibit low-level binding affinity to a non-human VEGF protein or to other VEGF isoforms.

"VEGF signaling" as used herein includes intracellular events induced by VEGF binding to one or more VEGF receptors, such as receptor phosphorylation (e.g., tyrosine phosphorylation), binding of intracellular signaling molecules (e.g., PLCγ; phospholipase C-γ) to the receptor or to other intracellular signaling molecules, the initiation of a signaling cascade, and/or the initiation of a biological response (e.g., induction of gene expression and changes in the physiology or development (e.g., proliferation) of the cell).

"Cancer" or "cancerous condition" as used herein refers to any medical condition mediated by neoplastic or malignant cell growth, proliferation, or metastasis, and includes both solid cancers and non-solid cancers such as leukemia. "Tumor" as used herein refers to a solid mass of neoplastic and/or malignant cells.

"Treating" or "treatment" of a condition as used herein includes preventing or alleviating a condition, slowing the onset or rate of development of a condition, reducing the risk of developing a condition, preventing or delaying the development of symptoms associated with a condition, reducing or ending symptoms associated with a condition, generating a complete or partial regression of a condition, curing a condition, or some combination thereof. With regard to cancer, "treating" or "treatment" may refer to inhibiting or slowing neoplastic or malignant cell growth, proliferation, or metastasis, preventing or delaying the development of neoplastic or malignant cell growth, proliferation, or metastasis, or some combination thereof. With regard to a tumor, "treating" or "treatment" includes eradicating all or part of a tumor, inhibiting or slowing tumor growth and metastasis, preventing or delaying the development of a tumor, or some combination thereof.

The term "specifically binds" as used herein refers to a non-random binding reaction between two molecules, such as for example between an antibody and a ligand. As used herein, an antibody or antigen-binding fragment that specifically binds a first ligand may exhibit cross-reactivity or low level binding affinity with a second ligand. In certain embodiments, an antibody or antigen-binding fragment that specifically binds a ligand binds the ligand with a binding affinity ($K_D$) of $\leq 10^{-7}$ M (e.g., $5 \times 10^{-8}$ M, $10^{-8}$ M, $5 \times 10^{-9}$ M, $10^{-9}$ M, $10^{-10}$ M). $K_D$ as used herein refers to the ratio of the dissociation rate to the association rate ($k_{off}/k_{on}$), may be determined using methods known in the art (e.g., using Biacore or Kinexa techniques). In certain embodiments, an antibody or antigen-binding fragment that specifically binds to a ligand binds to that ligand with a binding affinity of no less than 10 fold higher (e.g., $\geq 10$ fold, $\geq 15$ fold, $\geq 20$ fold, $\geq 50$ fold, $\geq 10^2$ fold, $\geq 10^3$ fold, or $\geq 10^4$ fold) than the binding affinity with which the antibody binds to a second ligand. In other embodiments, an antibody that specifically binds a ligand such as hVEGF$_{165}$ binds the ligand with a binding affinity ($K_D$) of $\geq 10^{-7}$ M, but exhibits no detectable binding affinity for a second ligand such as mVEGF$_{165}$.

An "isolated" substance has been altered by the hand of man from the natural state. If an "isolated" composition or substance occurs in nature, it has been changed or removed from its original environment, or both. For example, a polynucleotide or a polypeptide naturally present in a living animal is not "isolated," but the same polynucleotide or polypeptide is "isolated" if it has been sufficiently separated from the coexisting materials of its natural state so as to exist in a substantially pure state.

The term "vector" as used herein refers to a vehicle into which a polynucleotide encoding a protein may be operably inserted so as to bring about the expression of that protein. A vector may be used to transform, transduce, or transfect a host cell so as to bring about expression of the genetic element it carries within the host cell. Examples of vectors include plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses. Categories of animal viruses used as vectors include retrovirus (including lentivirus), adenovirus, adeno-associated virus, herpesvirus (e.g., herpes simplex virus), poxvirus, baculovirus, papillomavirus, and papovavirus (e.g., SV40). A vector may contain a variety of elements for controlling expression, including promoter sequences, transcription initiation sequences, enhancer sequences, selectable elements, and reporter genes. In addition, the vector may contain an origin of replication. A vector may also include materials to aid in its entry into the cell, including but not limited to a viral particle, a liposome, or a protein coating.

The phrase "host cell" as used herein refers to a cell into which an exogenous polynucleotide and/or a vector has been introduced. A host cell may be selected from a variety of cell types, including for example bacterial cells such as E. coli or B. subtilis cells, fungal cells such as yeast cells or Aspergillus cells, insect cells such as Drosophila S2 or Spodoptera Sf9 cells, or animal cells such as fibroblasts, CHO cells, COS cells, NSO cells, HeLa cells, BHK cells, HEK 293 cells, or human cells.

A "disease associated with aberrant angiogenesis" as used herein refers to any condition that is caused by, exacerbated by, or otherwise linked to increased angiogenesis, specifically increased angiogenesis associated with or mediated by VEGF signaling. Such conditions include cancers mediated by cells that are dependent on neo-angiogenesis for growth, proliferation, or metastasis, diseases of the eye such as for example wet AMD, and inflammatory conditions such as for example rheumatoid arthritis, psoriasis, scleroderma, chronic obstructive pulmonary disease (COPD), or asthma.

The ability to "block binding" or "compete for binding" as used herein refers to the ability of an antibody or antigen-binding fragment to inhibit the binding interaction between two molecules to any detectable agree. In certain embodiments, an antibody or antigen-binding fragment that blocks binding between two molecules inhibits the binding interaction between the two molecules by at least 50%. In certain embodiments, this inhibition may be greater than 60%, in certain embodiments greater than 70%, in certain embodiments greater than 80%, and in certain embodiments greater than 90%. In certain embodiments, the binding interaction being inhibited may be that of Bevacizumab to hVEGF$_{165}$. In certain other embodiments, the interaction being inhibited may be that of hVEGF$_{165}$ or any other VEGF ligand to VEGF-R1 and/or VEGF-R2.

Fully Human VEGF Antibodies and
Antigen-Binding Fragments

Fully human antibodies have several potential advantages over murine, chimeric, or humanized antibodies in terms of both safety and efficacy. First, their lack of non-human residues makes fully human antibodies less likely to generate a host immune response following administration. Second, fully human antibodies generally exhibit lower clearance rates than other antibody types. This decreased clearance rate allows for the use of lower dosage amounts and frequencies.

Provided herein are anti-hVEGF antibodies and antigen-binding fragments thereof that have been characterized as possessing superior anti-tumor activity in vivo. This represents an unexpected and surprising discovery because of the uncertainty associated with developing antibodies with superior in vitro antigen binding characteristics as a function of $K_D$ in combination with superior in vivo biological effects. Indeed, it is known that antibodies with particularly high in vitro binding affinity for VEGF do not necessarily possess high in vivo efficacy (Liang 2006). Therefore, identification of antibodies with high in vivo efficacy such as those disclosed herein is highly unpredictable and requires extensive scientific experimentation.

Disclosed herein are the fully human parental antibodies XPA.10.064 and XPA.072, both of which specifically bind hVEGF$_{165}$. As discussed below, the parental XPA.10.064 antibody was affinity matured to generate antibodies with high in vivo efficacy. XPA.10.064 and XPA.10.072 were identified by panning a phage display scFv library with hVEGF$_{165}$. The heavy and light chain variable region sequences of XPA.10.072 are set forth below and in SEQ ID NOs:2 and 3, respectively, and the heavy and light chain variable region sequences of XPA.10.064 are set forth below and in SEQ ID NOs:4 and 5, respectively. The XPA.10.072 and XPA.10.064 heavy chain variable regions as set forth in SEQ ID NOs:2 and 4, respectively, contain CDRs at residues 31-35 (HCDR1, SEQ ID NO:6), 50-66 (HCDR2, SEQ ID NO:7), and 99-108 (HCDR3, SEQ ID NO:8). The XPA.10.072 light chain variable region as set forth in SEQ ID NO:3 contains CDRs at residues 26-35 (LCDR1, SEQ ID NO:9), 51-57 (LCDR2, SEQ ID NO:10), and 90-100 (LCDR3, SEQ ID NO:11). The XPA.10.064 light chain variable region as set forth in SEQ ID NO:5 contains CDRs at residues 23-35 (LCDR1, SEQ ID NO:12), 51-57 (LCDR2, SEQ ID NO:13), and 90-100 (LCDR3, SEQ ID NO:14).

Amino acid sequences of the mature XPA.10.072 and XPA.10.064 heavy and light chains (lacking signal sequences) (CDRs are underlined):

XPA.10.072 heavy chain:

(SEQ ID NO: 2)
RLQLVQSGAEVRKPGASVKVSCKASGYSFT<u>GHYIH</u>WARQAPGQGLEWMG

<u>WINPYSGGTNFPREFQG</u>RVTMTRDTSVNTVYMELTRLTSDDTSVYYCAR

<u>DHRIVGGLDY</u>WGQGTLVTVSS.

XPA.10.072 light chain:

(SEQ ID NO: 3)
QSVLTQPPSASGTPGQRVTISCSGSS<u>SNLGSNFVY</u>WYQQLPGTAPKLLI

Y<u>RNHQRPS</u>GVPDRFSGSKSGTSASLAISGLRSEDEADYYC<u>ASWDDSLRV</u>

<u>VV</u>FGGGTKLTVL.

XPA.10.064 heavy chain:

(SEQ ID NO: 4)
EVQLVQSGAEVRKPGASVKVSCKASGYSFT<u>GHYIH</u>WVRQAPGQGLEWMG

<u>WINPYSGGTNFPREFQG</u>RVTMTRDTSVNTVYMELTRLTSDDTSVYYCAR

<u>DHRIVGGLDY</u>WGQGTLVTVSS.

XPA.10.064 light chain (SEQ ID NO: 5)
SYVLTQPPSASGTPGQRVTISC<u>SGSSSNIGINYVY</u>WYQQLPGTAPKLLI Y<u>RNDQRPS</u>GVPDRFSGSKSGTSASLAISGLRSEDEADYYC<u>ATWDDSLSG</u>

<u>VV</u>FGGGTKVTVL.

Based on the ability of XPA.10.064 and XPA.10.072 scFvs to bind hVEGF$_{165}$ with high affinity in an ELISA and to inhibit binding of hVEGF$_{165}$ to VEGF-R1 and VEGF-R2, the antibodies were selected for conversion to scFv-Fc and IgG2 for additional functional studies. XPA.10.064 and XPA.10.072 scFv-Fcs and IgG2s all exhibited similar high binding affinity for hVEGF$_{165}$ as determined by Biacore analysis. Both antibodies also bound hVEGF$_{121}$. XPA.10.064 and XPA.10.072 IgG2s displayed only weak binding to mVEGF$_{165}$. The binding affinities of XPA.10.064 and XPA.10.072 IgG2s for hVEGF$_{165}$ were 1.24-1.71 nM and 1.66-1.7 nM, respectively. Biacore analysis also revealed that XPA.10.064 and XPA.10.072 IgG2s block binding of hVEGF$_{165}$ to VEGF-R1 and VEGF-R2 to a degree similar to that observed for Bevacizumab. The ability of XPA.10.064 and XPA.10.072 to inhibit VEGF signaling was confirmed by ELISA experiments showing that both antibodies inhibit hVEGF$_{165}$-induced VEGF-R2 phosphorylation.

Epitope analysis suggested that XPA.10.064 and XPA.10.072 bind linear epitopes on hVEGF$_{165}$, and that these epitopes may overlap to at least partially with the epitopes bound by Bevacizumab. Immunohistochemical analysis revealed that, unlike Bevacizumab, XPA.10.064 and XPA.10.072 both exhibit broad range tissue cross-reactivity. Both antibodies inhibited HUVEC proliferation, and both inhibited angiogenesis and tumor growth in vivo. A summary of the characteristics of XPA.10.064 and XPA.10.072 is set forth in Table 1.

TABLE 1

Summary of XPA.10.064 and XPA.10.072 characteristics

| | XPA.10.064 | XPA.10.072 | Bevacizumab |
|---|---|---|---|
| HUVEC Proliferation Potency (HPP): HEK293-hVEGF$_{165}$, IgG2 (IC$_{50}$) | 0.07 µg/ml (0.66 in 2nd assay) | 0.68 µg/ml | 0.04 µg/ml |
| HPP: sf21-hVEGF$_{165}$, scFvFc (IC$_{50}$) | 0.41 µg/ml | >1 µg/ml | 0.06 µg/ml |
| HPP: sf21-hVEGF$_{165}$, IgG2 (IC$_{50}$) | 0.15 µg/ml | 0.24 µg/ml | 0.05 µg/ml |
| Binding to hVEGF$_{165}$ (K$_D$) | 1.24-1.71 nM (IgG2) | 1.66-1.70 nM (IgG2) | 0.425-0.605 nM (IgG2) |
| Binding to mVEGF$_{165}$ (K$_D$) | Weak binding (>100 nM) by Biacore analysis | Weak binding (>100 nM) by Biacore analysis | No detectable binding by Biacore analysis |
| Human/murine cross-reactivity | No | No | No |
| Blocks binding of hVEGF$_{165}$ to VEGF-R1 | Yes (scFv-Fc) | Yes (scFv-Fc) | Yes |
| Blocks binding of hVEGF$_{165}$ to VEGF-R2 | Yes (scFv-Fc) | Yes (scFv-Fc) | Yes |
| Binds different hVEGF$_{165}$ epitope than Bevacizumab | No | No | — |
| Conformational vs. linear epitope binding | Linear | Linear | Linear |
| MPA (% αKLH cntr; 2 × 5 mg/kg) | 20 | 26 | 38 |

Affinity maturation was carried out on the heavy chain CDRs of XPA.10.064 in order to generate mutagenized versions of the fully human antibodies with improved binding and efficacy. An antibody library was generated by randomly mutagenizing XPA.10.064 HCDR3 in blocks of five amino acids, and the library was screened for binding to hVEGF$_{165}$ using phage display techniques. The HCDR3 sequences of five affinity matured IgGs (XPA.10.064.03, XPA.10.064.04, XPA.10.064.06, XPA.10.064.07, and XPA.10.064.10) are set forth below and in SEQ ID NOs:15-19, respectively.

```
                              (SEQ ID NO: 15)
XPA.10.064.03: DQMVHGGLDY.

(SEQ ID NO: 16)
XPA.10.064.04: DEMQNGGLDY.

(SEQ ID NO: 17)
XPA.10.064.06: DEMTRGGLDY.

(SEQ ID NO: 18)
XPA.10.064.07: DEMHVGGLDY.

(SEQ ID NO: 19)
XPA.10.064.10: DEMVWGGLDY.
```

Each of the XPA.10.064 affinity matured clones bound hVEGF$_{165}$ with a higher affinity than the parental XPA.10.064 antibody or Bevacizumab as determined by Biacore analysis, and exhibited only weak binding to mVEGF$_{165}$. The affinity matured clones also exhibited the ability to inhibit HUVEC proliferation to a greater extent than parental XPA.10.064. In addition, XPA.10.064.06 exhibited the ability to inhibit tumor growth in vivo in a Rhabdomyosarcoma tumor growth model to a greater extent than Bevacizumab at dosages as low as 0.1 mg/kg. The percent tumor growth inhibition following administration of XPA.10.064.06 at 0.1 mg/kg and 0.5 mg/kg was approximately the same as that obtained by administering Bevacizumab at dosages at least five times greater. When administered at the same dosage, XPA.10.064.06 inhibited tumor growth to a specified size for a duration at least two to three times longer than Bevacizumab. As discussed above, this increase in in vivo efficacy was unexpected because increasing the affinity of a VEGF antibody does not necessarily correlate with an increase in in vivo tumor growth reduction efficacy (Liang 2006).

Provided herein in certain embodiments are antibodies and antigen-binding fragments that comprise the HCDR3 sequence of XPA.10.064.03, XPA.10.064.04, XPA.10.064.06, XPA.10.064.07, or XPA.10.064.10 as set forth in SEQ ID NOs:15-19, respectively. In certain of these embodiments, the antibodies or antigen-binding fragments may further comprise the HCDR1 (GHYIH) and/or HCDR2 (WINPYSGGTNFPREFQG) sequence of XPA.10.064 as set forth in SEQ ID NOs:6 and 7, respectively. In certain embodiments, the antibodies or antigen-binding fragments provided herein comprise the heavy chain variable sequence of XPA.10.064.03, XPA.10.064.04, XPA.10.064.06, XPA.10.064.07, or XPA.10.064.10 as set forth below and in SEQ ID NOs:20-24, respectively. In certain embodiments, the antibodies or antigen-binding fragments further comprise one or more of the LCDR sequences of XPA.10.064 as set forth in SEQ ID NOs:12-14. In certain of these embodiments, the antibodies or antigen-binding fragments comprise the light chain variable sequence of XPA.10.064 as set forth in SEQ ID NO:5. Also disclosed herein in certain embodiments are antibodies and antigen-binding fragments thereof that bind to the same epitope bound by the affinity-matured antibodies XPA.10.064.03, XPA.10.064.04, XPA.10.064.06, XPA.10.064.07, or XPA.10.064.10. The amino acid sequences of the mature affinity matured XPA.10.064 heavy chains (lacking signal sequences) are set forth below and in SEQ ID NOs:20-24 (CDRs underlined):

```
XPA.10.064.03:
                              (SEQ ID NO: 20)
EVQLVQSGAEVRKPGASVKVSCKASGYSFTGHYIHWVRQAPGQGLEWMG

WINPYSGGTNFPREFQGRVTMTRDTSVNTVYMELTRLTSDDTSVYYCAR

DQMVHGGLDYWGQGTLVTVSS.

XPA.10.064.04:
                              (SEQ ID NO: 21)
EVQLVQSGAEVRKPGASVKVSCKASGYSFTGHYIHWVRQAPGQGLEWMG

WINPYSGGTNFPREFQGRVTMTRDTSVNTVYMELTRLTSDDTSVYYCAR

DEMQNGGLDYWGQGTLVTVSS.

XPA.10.064.06:
                              (SEQ ID NO: 22)
EVQLVQSGAEVRKPGASVKVSCKASGYSFTGHYIHWVRQAPGQGLEWMG

WINPYSGGTNFPREFQGRVTMTRDTSVNTVYMELTRLTSDDTSVYYCAR

DEMTRGGLDYWGQGTLVTVSS.
```

XPA.10.064.07:
(SEQ ID NO: 23)
EVQLVQSGAEVRKPGASVKVSCKASGYSFT<u>GHYIH</u>WVRQAPGQGLEWMG

<u>WINPYSGGTNFPREFQG</u>RVTMTRDTSVNTVYMELTRLTSDDTSVYYCAR

<u>DEMHVGGLDY</u>WGQGTLVTVSS.

XPA.10.064.10:
(SEQ ID NO: 24)
EVQLVQSGAEVRKPGASVKVSCKASGYSFT<u>GHYIH</u>WVRQAPGQGLEWMG

<u>WINPYSGGTNFPREFQG</u>RVTMTRDTSVNTVYMELTRLTSDDTSVYYCAR

<u>DEMVWGGLDY</u>WGQGTLVTVSS.
CDRs are underlined.

In certain embodiments, the antibodies and antigen-binding fragments provided herein comprise the HCDR3 sequence of XPA.10.064.06 or XPA.10.064.07 as set forth in SEQ ID NOs:17 and 18, respectively. In certain of these embodiments, the antibodies or antigen-binding fragments may further comprise the HCDR1 and/or HCDR2 sequence of XPA.10.064 as set forth in SEQ ID NOs:6 and 7, respectively. In certain embodiments, the antibodies or antigen-binding fragments provided herein comprise the heavy chain variable sequence of XPA.10.064.06 or XPA.10.064.07 as set forth in SEQ ID NOs:22 and 23, respectively. In certain embodiments, the antibodies or antigen-binding fragments further comprise one or more of the LCDR sequences of XPA.10.064 as set forth in SEQ ID NOs:12-14. In certain of these embodiments, the antibodies or antigen-binding fragments comprise the light chain variable sequence of XPA.10.064 as set forth in SEQ ID NO:5.

Provided herein in certain embodiments are antibodies or antigen-binding fragments thereof that specifically bind VEGF and have one or more of the following properties: (1) a $K_D$ for $hVEGF_{165}$ of about $10^{-10}$ M (i.e., similar to the average $K_D$ exhibited by the affinity matured XPA.10.064 antibodies XPA.10.064.03, XPA.10.064.04, XPA.10.064.06, XPA.10.064.07, and XPA.10.064.10); (2) a $k_a$ for $hVEGF_{165}$ of about $1.89 \times 10^5$ (i.e., similar to the average $K_a$ exhibited by the affinity matured antibodies XPA.10.064.03, XPA.10.064.04, XPA.10.064.06, XPA.10.064.07, and XPA.10.064.10); (3) a $k_d$ for $hVEGF_{165}$ of about $1.73 \times 10^{-5}$ (i.e., similar to the average $k_d$ exhibited by the affinity matured antibodies XPA.10.064.03, XPA.10.064.04, XPA.10.064.06, XPA.10.064.07, and XPA.10.064.10); (4) a binding affinity (as a function of $K_D$) for $hVEGF_{165}$ that is greater than that of Bevacizumab (i.e., about $4.25 \times 10^{-10}$) to about the same degree that the binding affinities of the affinity matured antibodies XPA.10.064.03, XPA.10.064.04, XPA.10.064.06, XPA.10.064.07, and XPA.10.064.10 for $hVEGF_{165}$ are greater than that of Bevacizumab; (5) the ability to inhibit HUVEC cell proliferation with an $IC_{50}$ of about 154 pM (i.e., similar to the average $IC_{50}$ exhibited by the affinity matured antibodies XPA.10.064.03, XPA.10.064.06, XPA.10.064.07, and XPA.10.064.10); (6) the ability to inhibit HUVEC cell proliferation with an $IC_{50}$ about 56% that of Bevacizumab; (7) a $K_D$ for $hVEGF_{165}$ from about $1.97 \times 10^{-10}$ M to about $3.49 \times 10^{-11}$ M (i.e., within the range exhibited by the affinity matured antibodies XPA.10.064.03, XPA.10.064.04, XPA.10.064.06, XPA.10.064.07, and XPA.10.064.10); (8) a $k_a$ for $hVEGF_{165}$ from about $1.5 \times 10^5$ to about $2.16 \times 10^5$ (i.e., within the range exhibited by the affinity matured antibodies XPA.10.064.03, XPA.10.064.04, XPA.10.064.06, XPA.10.064.07, and XPA.10.064.10); (9) a $k_d$ for $hVEGF_{165}$ from about $6.65 \times 10^{-6}$ to about $2.94 \times 10^{-5}$ (i.e., within the range exhibited by the affinity matured antibodies XPA.10.064.03, XPA.10.064.04, XPA.10.064.06, XPA.10.064.07, and XPA.10.064.10); (10) the ability to inhibit HUVEC cell proliferation with an $IC_{50}$ of about 129 pM to about 174 pM (i.e., within the range exhibited by the affinity matured antibodies XPA.10.064.03, XPA.10.064.06, XPA.10.064.07, and XPA.10.064.10); (11) a binding affinity for $hVEGF_{165}$ that is at least about 10 times greater than the binding affinity of the antibody or antigen-binding fragment for $mVEGF_{165}$; and (12) the ability to compete with Bevacizumab for $hVEGF_{165}$ binding.

Further provided herein are complexes comprising one or more of the antibodies or antigen-binding fragments disclosed herein and one or more VEGF ligands or antigenic fragments thereof. These complexes may be formed in vitro or in vivo. For example, in certain embodiments, such complexes may be formed when an antibody or antigen-binding fragment as disclosed herein is administered to a subject and binds to VEGF in the body of the subject.

The affinity matured antibodies XPA.10.064.03, XPA.10.064.04, XPA.10.064.06, XPA.10.064.07, and XPA.10.064.10 as provided herein were generated by random mutagenesis of XPA.10.064 HCDR3 and subsequent binding and functional assays. In certain embodiments, the methionine residue in XPA.10.064.06 HCDR3 may be substituted with another amino acid residue, such as for example an alanine, lysine, proline, threonine, or leucine residue. Examples of such mutated HCDR3 sequences are set forth in SEQ ID NOs:25-29. Therefore, in certain embodiments, antibodies and antigen-binding fragments are provided that comprise the HCDR3 sequence set forth in any of SEQ ID NOs:25-29. In certain of these embodiments, the antibodies or antigen-binding fragments may further comprise the HCDR1 and/or HCDR2 sequence of XPA.10.064 as set forth in SEQ ID NOs:6 and 7, respectively. In certain embodiments, the antibodies or antigen-binding fragments may further comprise one or more of the LCDR sequences of XPA.10.064 as set forth in SEQ ID NOs:12-14. In certain of these embodiments, the antibodies or antigen-binding fragments may comprise the light chain variable sequence of XPA.10.064 as set forth in SEQ ID NO:5.

In certain embodiments, additional affinity matured versions of the parental antibody XPA.10.064 are generated by mutagenizing one or more residues of XPA.10.064 HCDR1, HCDR2, LCDR1, LCDR2, and/or LCDR3. Therefore, in certain embodiments, antibodies and antigen-binding fragments are provided that comprise one or more CDR sequences of XPA.10.064, wherein the one or more CDR sequences contain one or more amino acid substitutions. Antibodies and antigen-binding fragments generated in this manner may be screened for binding to $hVEGF_{165}$ in order to identify affinity matured antibodies with improved binding characteristics. Antibodies with favorable binding characteristics may be subjected to one or more functional assays to determine their ability to, for example, inhibit HUVEC proliferation, angiogenesis, tumor growth, and/or $hVEGF_{165}$-induced phosphorylation of VEGF-R2.

In certain embodiments, the antibodies or antigen-binding fragments provided herein bind $hVEGF_{165}$ with a greater affinity than that of Bevacizumab for $hVEGF_{165}$. For example, in certain embodiments, the antibodies or antigen-binding fragments provided herein bind $hVEGF_{165}$ with a $K_D \leq 500$ pM. In certain of these embodiments, the antibodies or antigen-binding fragments bind $hVEGF_{165}$ with a $K_D \leq 200$ pM, in other embodiments $\leq 150$ pM, in other embodiments $\leq 100$ pM, and in still other embodiments $\leq 50$ pM.

In certain embodiments, the antibodies and antigen-binding fragments provided herein exhibit no detectable binding affinity or weak binding affinity for mVEGF$_{165}$. In certain of these embodiments, the antibodies or antigen-binding fragments exhibit a K$_D$ for mVEGF$_{165}$≧about 100 nM. In certain embodiments, the antibodies and antigen-binding fragments exhibit a binding affinity for hVEGF$_{165}$ that is at least 10-fold greater (e.g., 20-fold, 30-fold, or 40-fold greater) than the binding affinity of the antibody or antigen-binding fragment for mVEGF$_{165}$. In certain of these embodiments, the binding affinity of the antibody or antigen-binding fragment for hVEGF$_{165}$ is at least 50-fold greater (e.g., 60-fold, 70-fold, 80-fold, or 90-fold greater) than the binding affinity of the antibody or antigen-binding fragment for mVEGF$_{165}$, and in certain embodiments at least 100-fold greater (e.g., 110-fold, 120-fold, 150-fold, 175-fold, 200-fold, 250-fold, 300-fold, 400-fold, or 500-fold greater).

Based on their high binding affinity for hVEGF$_{165}$ and hVEGF$_{121}$ and their ability to block VEGF binding to VEGF-R1 and VEGF-R2 and VEGF-induced receptor phosphorylation, the antibodies and antigen-binding fragments provided herein may be used to inhibit VEGF signaling. On this basis, the antibodies and antigen-binding fragments may be used to treat various conditions associated with VEGF expression and/or signaling.

The antibodies and antigen-binding fragments provided herein have been found to inhibit HUVEC proliferation and to inhibit angiogenesis. Therefore, the antibodies and antigen-binding fragments may be used to treat various conditions associated with increased angiogenesis. For example, the antibodies and antigen-binding fragments may be used to treat cancer by inhibiting the proliferation of blood vessels from a tumor site and thus inhibiting tumor growth. Likewise, the antibodies and antigen-binding fragments may used to treat cancer by destroying blood vessels at a tumor site, resulting in tumor necrosis. The efficacy of the antibodies and antigen-binding fragments disclosed herein for the treatment of cancer has been confirmed in vivo.

In certain embodiments, the antibodies and antigen-binding fragments provided herein inhibit angiogenesis and/or tumor growth at a level similar to or greater than Bevacizumab. In in vivo A673 Rhabdomyosarcoma tumor growth inhibition experiments, XPA.10.064 and XPA.10.072 inhibited tumor growth to a degree that was similar to or greater than Bevacizumab at all dosages tested. The affinity matured antibody XPA.10.064.06 inhibited tumor growth more effectively than Bevacizumab. As a function of percent tumor growth inhibition, XPA.10.064.06 was approximately five-fold more effective than Bevacizumab at reducing tumor growth. Likewise, XPA.10.064.06 delayed tumor growth to a specified size for a significantly longer duration than Bevacizumab when the antibodies were administered at the same dosage. Therefore, in certain embodiments, the antibodies and antigen-binding fragments disclosed herein inhibit tumor growth as measured by percent tumor growth inhibition or duration of tumor growth delay at least twice as effectively as Bevacizumab when administered at the same or similar dosages. In certain of these embodiments, the antibodies and antigen-binding fragments disclosed herein inhibit tumor growth at least three times as effectively as Bevacizumab, in other embodiments at least four times as effectively as Bevacizumab, in other embodiments at least five times as effectively as Bevacizumab, and in other embodiments more than five times as effectively as Bevacizumab. Likewise, in certain embodiments the antibodies and antigen-binding fragments disclosed herein inhibit tumor growth to a degree approximately equal to or greater than Bevacizumab when administered at a lower dosage than Bevacizumab. In certain of these embodiments, the antibodies and antigen-binding fragments disclosed herein inhibit tumor growth to a degree approximately equal to or greater than Bevacizumab when administered at one-half the dosage of Bevacizumab, in other embodiments at one-third the dosage of Bevacizumab, in other embodiments at one-fourth the dosage of Bevacizumab, and in other embodiments at one-fifth the dosage of Bevacizumab. The antibodies and antigen-binding fragments provided herein may exhibit similar or improved pharmacokinetic (PK) properties as compared to Bevacizumab. For example, the antibodies or antigen-binding fragments may exhibit increased circulating half-life or decreased immunogenicity as compared to Bevacizumab. In certain embodiments wherein the antibodies or antigen-binding fragments exhibit similar or improved pharmacokinetic properties versus Bevacizumab, the antibodies or antigen-binding fragments may be administered over a longer interval than Bevacizumab without exhibiting negative effects associated with increased intervals of Bevacizumab administration.

The antibodies and antigen-binding fragments disclosed herein may be used in the treatment of any condition associated with aberrant angiogenesis controlled at least in part by VEGF signaling. These conditions, which are generally associated with increased VEGF expression levels, include ocular diseases associated with increased angiogenesis, such as wet AMD or proliferative retinopathies such as diabetic retinopathy, diabetic kidney disease and other diabetic vascular proliferative diseases, cystic fibrosis, and various tumor types (Amoroso 1997; McColley 2000; Khamaisi 2003).

Cancerous conditions and tumor types that may be treated using the antibodies or antigen-binding fragments disclosed herein include but are not limited to carcinoma, blastoma, sarcoma, germ cell tumor, or hematological or lymphoid malignancy such as leukemia, lymphoma, or multiple myeloma. More specifically, cancerous conditions and tumor types that may be treated using the antibodies disclosed herein include but are not limited to squamous cell cancer, lung cancer (e.g., small cell lung cancer, non-small cell lung cancer (NSCLC), adenocarcinoma of the lung, or squamous cell carcinoma of the lung), cancer of the peritoneum, liver cancer (e.g., hepatocellular carcinoma/hepatoma), gastric or stomach cancer (e.g., gastrointestinal cancer), pancreatic cancer, brain tumor (e.g., glioblastoma/glioblastoma multiforme (GBM), non-glioblastoma brain tumor, or meningioma), glioma (e.g., ependymoma, astrocytoma, anaplastic astrocytoma, oligodendroglioma, or mixed glioma such as oligoastrocytoma), cervical cancer, ovarian cancer, liver cancer (e.g., hepatoblastoma, hepatocellular carcinoma/hepatoma, or hepatic carcinoma), bladder cancer (e.g., urothelial cancer), breast cancer, colon cancer, colorectal cancer, rectal cancer, endometrial or uterine carcinoma, salivary gland carcinoma, kidney or renal cancer (e.g., rhabdoid tumor of the kidney), prostate cancer, vulval cancer, penile cancer, anal cancer (e.g., anal squamous cell carcinoma), thyroid cancer, head and neck cancer (e.g., nasopharyngeal cancer), skin cancer (e.g., melanoma or squamous cell carcinoma), osteosarcoma, Ewing's sarcoma, chondrosarcoma, soft tissue sarcoma (e.g., rhabdomyosarcoma, fibrosarcoma, Kaposi's sarcoma), carcinoid cancer, eye cancer (e.g., retinoblastoma), mesothelioma, lymphocytic/lymphoblastic leukemia (e.g., acute lymphocytic/lymphoblastic leukemia (ALL) of both T-cell lineage and B-cell precursor lineage, chronic lymphoblastic/lymphocytic leukemia (CLL), acute myelogenous/myeloblastic leukemia (AML), including mast cell leukemia, chronic myelogenous/myelocytic/myeloblastic leukemia (CML), hairy cell leukemia (HCL), Hodgkin's disease, non-Hodgkin's lymphoma, chronic myelomonocytic leukemia (CMML), follicular lymphoma (FL), diffuse large B cell lymphoma (DLBCL), mantle cell lymphoma (MCL), Burkitt's lymphoma (BL), mycosis fungoides, Sezary syndrome, cutaneous T-cell lymphoma, mast cell neoplasm, medulloblastoma, nephroblastoma, solitary plasmacytoma, myelodysplastic syndrome, chronic and non-chronic myeloproliferative disorder, central nervous system tumor, pituitary adenoma, vestibular schwannoma, primitive neuroectodermal tumor, ependymoma, choroid plexus papilloma, polycythemia vera, thrombocythemia, idiopathic myelofibrosis, and pediatric cancers such as pediatric sarcomas (e.g., neuroblastoma, rhabdomyosarcoma, and osteosarcoma). In addition, tumors can be malignant (e.g., cancers) or benign (e.g., hyperplasia, cyst, pseudocyst, hamartoma, and benign neoplasm).

Tumor types that may be treated using the antibodies or antigen-binding fragments disclosed herein also include cancers associated with a particular biomarker. For example, a biomarker includes, but is not limited to, mutations in the von Hippel-Lindau (VHL) tumor suppressor gene and/or overexpression of Hypoxia-inducible factor-1α (HIF-1α). In certain embodiments, the antibodies can be used to treat cancers displaying mutations in the VHL tumor suppressor gene. Mutations in the VHL gene result in the constitutive stabilization of hypoxia-inducible transcription factors 1α and 2α, which bind to enhancer elements in the VEGF gene and stimulate angiogenesis (Harris 2000). VHL mutant tumor types that may be treated using the antibodies disclosed herein include, for example, central nervous system hemangioblastomas, retinal hemangioblastomas, endolymphatic sac tumors, clear cell renal cell cancers and/or renal cysts, pheochromocytomas, pancreatic cysts, neuroendocrine tumors, and epididymal and broad ligament cystadenomas. Subjects are first selected or screened for the presence of VHL gene mutations through known methods such as the molecular detection using a mutation specific nested reverse transcription polymerase chain reaction or a nested single strand conformational polymorphism analysis (Ashida 2003). The identified subjects are then subject to the treatment with the antibodies or antigen-binding fragments as disclosed herein. In other embodiments, the antibodies can be used to treat cancers displaying overexpression of HIF-1α in a subject. The HIF-1α overexpression can be examined through biopsies of a tissue (e.g., brain, breast, cervical, esophageal, oropharyngeal, ovarian, and prostate tissues). The identified subjects are selected and subject to the treatment with the antibodies or antigen-binding fragments, or with the antibodies or antigen-binding fragments in combination with HIF-1α inhibitors such as 2-methoxyestradiol, 4-O-methylsarcerneol, manassantin A, manassantin B1, NSC-134754, NSC-643735, topotecan, SCH66336, PX-478, R115777, Cetuximab, 103D5R, and NSAID (Kimbro 2006). Provided herein are methods for selecting a subject for therapy with the antibodies or antigen-binding fragments disclosed herein if the subject is observed to possess one or more of the biomarkers discussed above (e.g., VHL gene mutation) and, optionally, treating said subject with the antibody or antibody-binding fragment.

Other conditions that may be treated by the antibodies and antigen-binding fragments described herein include inflammatory conditions such as rheumatoid arthritis, psoriasis, scleroderma, chronic obstructive pulmonary disease, and asthma. In certain embodiments, the antibodies or antigen-binding fragments provided herein may be used to treat a condition that has become resistant to treatment with Bevacizumab.

The antibodies and antigen-binding fragments provided herein may be utilized in various non-therapeutic uses. In certain embodiments, the antibodies or antigen-binding fragments may be used as affinity purification agents to purify $hVEGF_{165}$, other VEGF isoforms, or fragments thereof. In these embodiments, the antibodies or antigen-binding fragments may be immobilized on a solid phase such as a resin or filter paper using methods known in the art. The antibodies or antigen-binding fragments may also be used to precipitate $hVEGF_{165}$, other VEGF isoforms, or fragments thereof from solution. In other non-therapeutic embodiments, the antibodies or antigen-binding fragments may be used in various in vitro or in vivo diagnostic or detection applications. In certain of these embodiments, the antibodies or antigen-binding fragments may be conjugated to a detectable label. In other embodiments, the antibodies or antigen-binding fragments may not be conjugated to a detectable label, but may be detected using a labeled secondary antibody that binds to the antibody. In certain embodiments, the antibodies or antigen-binding fragments disclosed herein may be used to detect $hVEGF_{165}$ expression. In certain of these embodiments, the antibodies or antigen-binding fragments may be used to diagnose a condition associated with increased $hVEGF_{165}$ expression. For example, the antibody or antigen-binding fragment may be contacted with a biological sample from a subject in order to diagnose a condition associated with increased $hVEGF_{165}$ expression in the subject. Likewise, the antibody or antigen-binding fragment may be administered to the subject directly, with binding to $hVEGF_{165}$ detected using methods known in the art.

Mutant epitope binding studies show that the antibodies and antigen-binding fragments disclosed herein may bind linear epitopes on VEGF that may overlap at least partially with the epitope recognized by Bevacizumab. Therefore, in certain embodiments, the antibodies or antigen-binding fragments disclosed herein may bind to an epitope consisting of or comprising residues 79-94 of $hVEGF_{165}$ (SEQ ID NO:1). Likewise, the antibodies or antigen-binding fragments may bind an epitope that completely or partially overlaps with the sequence corresponding to residues 79-94 of SEQ ID NO:1. In certain embodiments the antibodies or antigen-binding fragments disclosed herein competitively inhibit Bevacizumab binding to $hVEGF_{165}$.

The antibodies or antigen-binding fragments provided herein may have a terminal half-life ($t_{1/2}$) in humans that is similar to or greater than that of Bevacizumab, which has a half-life of 17-21 days (Ferrara 2004). For example, in certain embodiments, the antibodies or antigen-binding fragments provided herein may have a terminal half-life of about 21 days, 28 days, 35 days, or 60 days. Terminal half-life, which refers to the time that it takes the plasma concentration of an administered antibody to decrease by one half, may be calculated using methods known in the art. In certain embodiments, the terminal half-life of the antibodies or antigen-binding fragments disclosed herein may be at least 17 days. In certain other embodiments, it may be 17-21 days, and in certain of these embodiments it may be greater than 21 days.

The antigen-binding fragments disclosed herein may comprise a fragment or fragments of an antibody, such as for example a Fab, Fab', F(ab')$_2$, Fv, or scFv fragment. These fragments can be produced from antibodies using methods well known in the art, such as for example proteolytic cleavage with enzymes such as papain to produce Fab fragments or pepsin to produce F(ab')$_2$ fragments. In certain embodiments, the antibodies or antigen-binding fragments disclosed herein may comprise one or more CDRs from SEQ ID NOs:2-5 or 20-24 grafted to one or more human framework regions.

The antibodies or antigen-binding fragments disclosed herein may be administered alone or in combination with one or more additional therapeutic agents. For example, the antibodies or antigen-binding fragments disclosed herein may be administered in combination with chemotherapy, radiation therapy, surgery for the treatment of cancer (e.g., tumorectomy), one or more anti-emetics or other treatments for complications arising from chemotherapy, or any other therapeutic agent for use in the treatment of cancer or any medical disorder mediated by elevated VEGF expression and/or signaling. In certain of these embodiments, an antibody or antigen-binding fragment as disclosed herein that is administered in combination with one or more additional therapeutic agents may be administered simultaneously with the one or more additional therapeutic agents, and in certain of these embodiments the antibody or antigen-binding fragment and the additional therapeutic agent(s) may administered as part of the same pharmaceutical composition. However, an antibody or antigen-binding fragment administered "in combination" with another therapeutic agent does not have to be administered simultaneously with or in the same composition as the agent. An antibody or antigen-binding fragment administered prior to or after another agent is considered to be administered "in combination" with that agent as the phrase is used herein, even if the antibody or antigen-binding fragment and second agent are administered via different routes. Where possible, additional therapeutic agents administered in combination with the antibodies or antigen-binding fragments disclosed herein are administered according to the schedule listed in the product information sheet of the additional therapeutic agent, or according to the Physicians' Desk Reference 2003 (*Physicians' Desk Reference*, 57th Ed; Medical Economics Company; ISBN: 1563634457; 57th edition (November 2002)) or protocols well known in the art.

Those of skill in the art will recognize that a variety of conjugates may be linked to the antibodies or antigen-binding fragments provided herein (see, for example, "Conjugate Vaccines", Contributions to Microbiology and Immunology, J. M. Cruse and R. E. Lewis, Jr. (eds.), Carger Press, New York, (1989)). These conjugates may be linked to the antibodies or antigen-binding fragments by covalent binding, affinity binding, intercalation, coordinate binding, complexation, association, blending, or addition, among other methods. In certain embodiments, the antibodies and antigen-binding fragments disclosed herein may be engineered to contain specific sites outside the epitope binding portion that may be utilized for binding to one or more conjugates. For example, such a site may include one or more reactive amino acid residues, such as for example cysteine or histidine residues, to facilitate covalent linkage to a conjugate. In certain embodiments, the antibodies may be linked to a conjugate indirectly, or through another conjugate. For example, the antibody or antigen-binding fragments may be conjugated to biotin, then indirectly conjugated to a second conjugate that is conjugated to avidin.

In certain embodiments, conjugates linked to the antibodies or antigen-binding fragments disclosed herein may comprise one or more agents meant to alter one or more pharmacokinetic (PK) properties of the antibody or antigen-binding fragment, such as for example polyethylene glycol (PEG) to increase the half-life or decrease the immunogenicity of the antibody or antigen-binding fragment (see, e.g., Katre 1990).

In certain embodiments, conjugates linked to the antibodies or antigen-binding fragments disclosed herein may comprise one or more detectable labels. Such labels include, but are not limited to, radioactive isotopes such as $^{123}$I, $^{124}$I, $^{125}$I, $^{131}$I, $^{35}$S, $^{3}$H, $^{111}$In, $^{112}$In, $^{14}$C, $^{64}$Cu, $^{67}$Cu, $^{86}$Y, $^{88}$Y, $^{90}$Y, $^{171}$Lu, $^{211}$At, $^{186}$Re, $^{188}$Re, $^{153}$Sm, $^{212}$Bi, and $^{32}$P, other lanthanides, luminescent labels, fluorescent labels such as for example fluorescein, rhodamine, dansyl, phycoerythrin, or Texas Red, and enzyme-substrate labels such as for example horseradish peroxidase, alkaline phosphatase, or β-D-galactosidase.

In certain embodiments, compositions are provided comprising antibodies or antigen-binding fragments disclosed herein linked to or in combination with one or more cytokines, which include proteins that act on a cell as an intercellular mediator. Example of cytokines include but are not limited to lymphokines, monokines, human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, fibroblast growth factor, prolactin, placental lactogen, tumor necrosis factor α and β, mullerian-inhibiting substance, mouse gonadotropin-associated peptide, inhibin, activin, integrin, thrombopoietin (TPO), nerve growth factors such as NGF-β, platelet growth factor, transforming growth factors such as TGF-α and TGF-β, insulin-like growth factor I and II, erythropoietin (EPO), osteoinductive factors, interferons such as interferon-α, -β, and -γ, colony stimulating factors such as macrophage-CSF, granulocyte macrophage CSF, and granulocyte-CSF, interleukins such IL-1, IL-1α, IL-2, IL-3, IL-4, IL-5, IL-6, IL-7, IL-8, IL-9, IL-10, IL-11, and IL-12, tumor necrosis factors such as TNF-α and TNF-β, and other polypeptide factors. The antibodies or antigen-binding fragments disclosed herein may be provided and/or administered in combination with any cytokine, including any of those listed above.

In certain embodiments, compositions are provided comprising antibodies or antigen-binding fragments disclosed herein linked to or in combination with one or more chemotherapeutic agents. Examples of chemotherapeutic agents include, but are not limited to, ALT-110, AMN-107 (Nilotinib), amrubicin, ARQ-197, atrasentan (Xinlay®), AV-299, AZD 1152, AZD 2171, batabulin, BIO-111, BIO-140, calcitriol, CC 8490, cilengitide, dasatinib, decatanib, DN-101, edotecarin, enzastaurin, erlotinib, everolimus, gimatecan, gossypol (e.g., gossypol acetate), GSK461364, GSK690693, IL13-PE38QQR, INO 1001, IPdR, ipilimumab, KRX-0402, Lep-etu, lonafarnib, lucanthone, LY 317615, MK-0457, MLN8054, neuradiab, nolatrexed, oblimersen, ofatumumab, ON 0910.Na, oregovomab, panitumumab, pazopanib, PHA-739358, R-763, RTA 744, rubitecan, Sdx 102, talampanel, temsirolimus, tesmilifene, tetrandrine, ticilimumab, TKI-258, TLK 286, trabectedin, vandetanib, vitespan, Xr 311, zanolimumab, 131-I-TM-601, and zolendronate, histrelin, azacitidine, dexrazoxane, alemtuzumab, lenalidomide, gemtuzumab, ketoconazole, nitrogen mustard, ibritumomab tiuxetan, decitabine, hexamethylmelamine, bexarotene, tositumomab, arsenic trioxide, editronate, cyclosporine, Edwina-asparaginase, and strontium 89.

In certain embodiments, an antibody or antigen-binding fragment provided herein is linked to or in combination with romidepsin (FK-228), which has the structure:

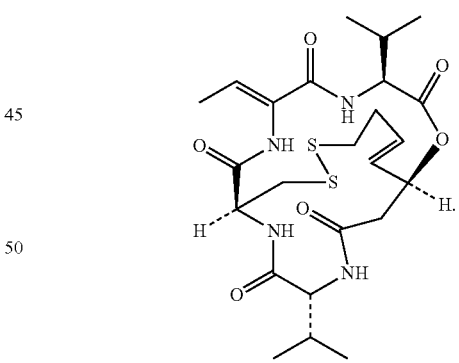

In certain embodiments, an antibody or antigen-binding fragment provided herein is linked to or in combination with ADS-100380, which has the structure:

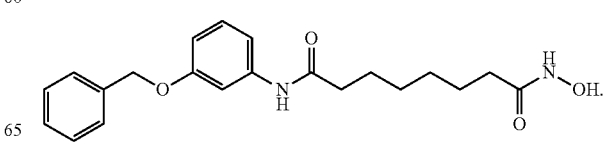

In certain embodiments, an antibody or antigen-binding fragment provided herein is linked to or in combination with CG-781, which has the structure:

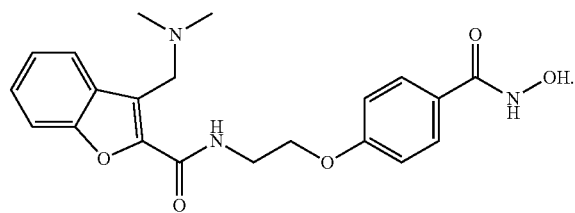

In certain embodiments, an antibody or antigen-binding fragment provided herein is linked to or in combination with CG-1521, which has the structure:

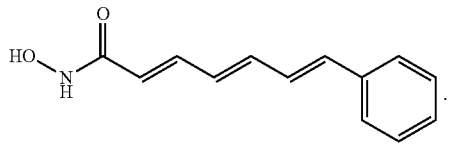

In certain embodiments, an antibody or antigen-binding fragment provided herein is linked to or in combination with SB-556629, which has the structure:

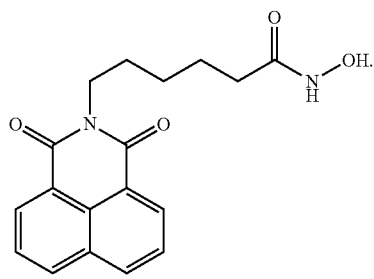

In certain embodiments, an antibody or antigen-binding fragment provided herein is linked to or in combination with chlamydocin, which has the structure:

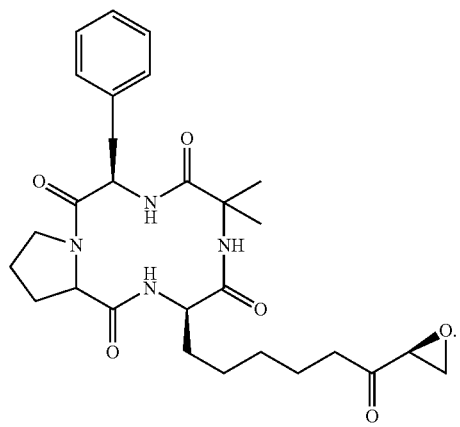

In certain embodiments, an antibody or antigen-binding fragment provided herein is linked to or in combination with JNJ-16241199, which has the structure:

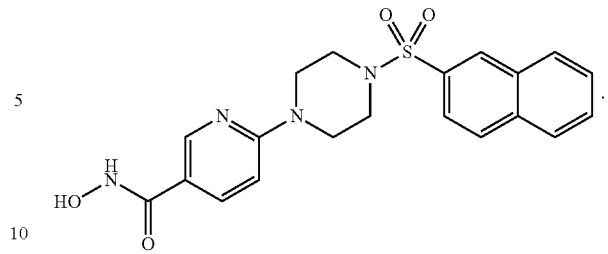

In certain embodiments, an antibody or antigen-binding fragment provided herein is linked to or in combination with:

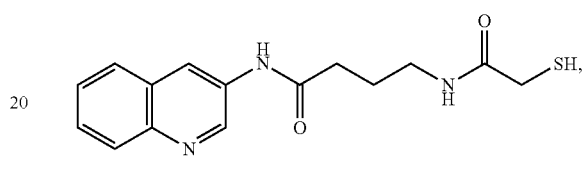

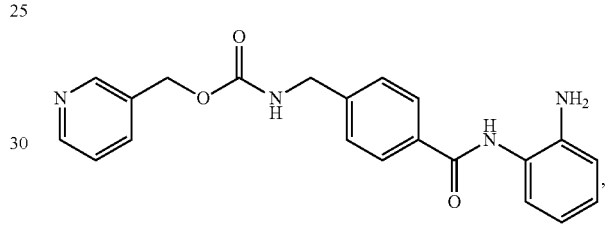

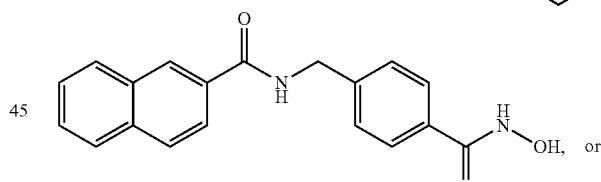

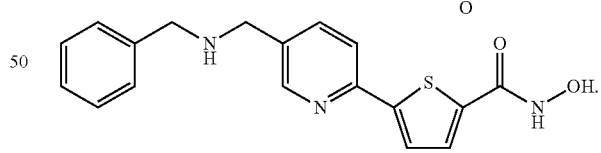

In certain embodiments, an antibody or antigen-binding fragment provided herein is linked to or in combination with vorinostat (SAHA), which has the structure:

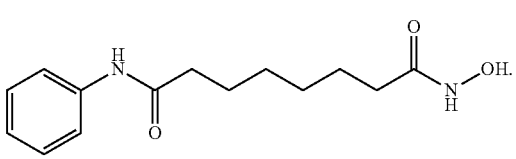

In certain embodiments, an antibody or antigen-binding fragment provided herein is linked to or in combination with etoposide (VP-16), which has the structure:

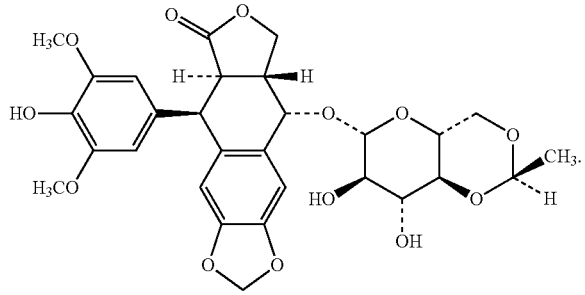

In certain embodiments, an antibody or antigen-binding fragment provided herein is linked to or in combination with gemcitabine, which has the structure:

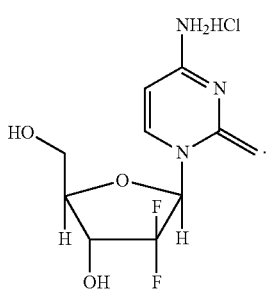

In certain embodiments, an antibody or antigen-binding fragment provided herein is linked to or in combination with a compound disclosed in U.S. Patent Publication No. 2004/0209878A1, wherein the compound has the following core structure:

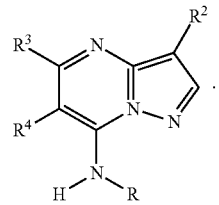

In certain embodiments, an antibody or antigen-binding fragment provided herein is linked to or used in combination with doxorubicin (Adriamycin®), including Caelyx or Doxil® (doxorubicin HCl liposome injection; Ortho Biotech Products L.P., Raritan, N.J.). Doxil® comprises doxorubicin in STEALTH® liposome carriers, which are composed of N-(carbonyl-methoxypolyethylene glycol 2000)-1,2-distearoyl-sn-glycero-3-phosphoethanolamine sodium salt (MPEG-DSPE), fully hydrogenated soy phosphatidylcholine (HSPC), and cholesterol. Doxorubicin has the structure:

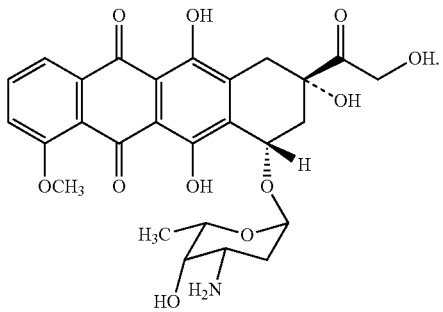

In certain embodiments, an antibody or antigen-binding fragment provided herein is linked to or in combination with 5'-deoxy-5-fluorouridine, which has the structure:

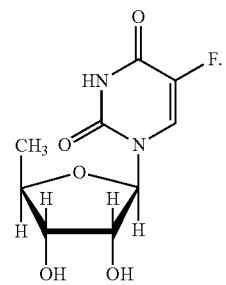

In certain embodiments, an antibody or antigen-binding fragment provided herein is linked to or in combination with vincristine, which has the structure:

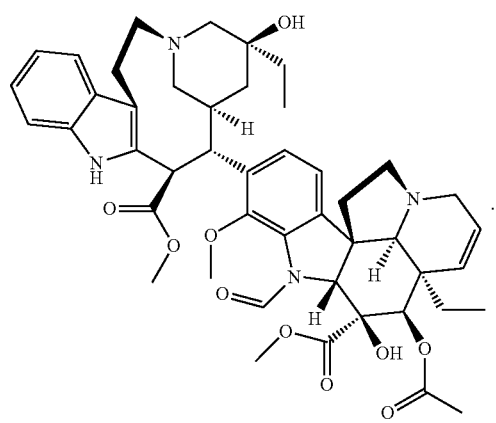

In certain embodiments, an antibody or antigen-binding fragment provided herein is linked to or in combination with temozolomide (methazolastone), which has the structure:

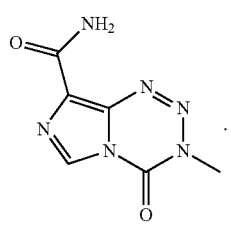

In certain embodiments, an antibody or antigen-binding fragment provided herein is linked to or in combination with a CDK inhibitor, such as ZK-304709 or Seliciclib (R-roscovitine, CYC-202). Seliciclib has the structure:

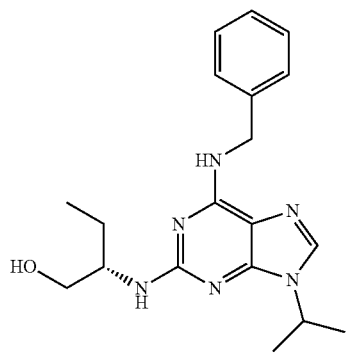

In certain embodiments, an antibody or antigen-binding fragment provided herein is linked to or in combination with a MEK inhibitor, such as PD0325901 or AZD-6244 (ARRY-142886). PD0325901 has the structure:

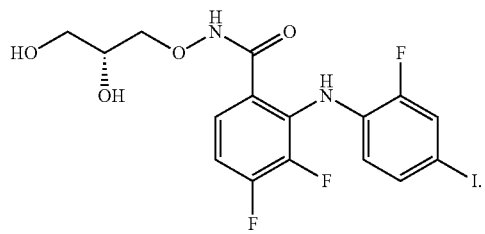

In certain embodiments, an antibody or antigen-binding fragment provided herein is linked to or in combination with capecitabine (5'-deoxy-5-fluoro-N-[(pentyloxy) carbonyl]-cytidine) or Pemetrexed (L-Glutamic acid, N-[4-[2-(2-amino-4,7-dihydro-4-oxo-1 H-pyrrolo[2,3-d]pyrimidin-5-yl) ethyl]benzoyl]-disodium salt, heptahydrate), which has the structure:

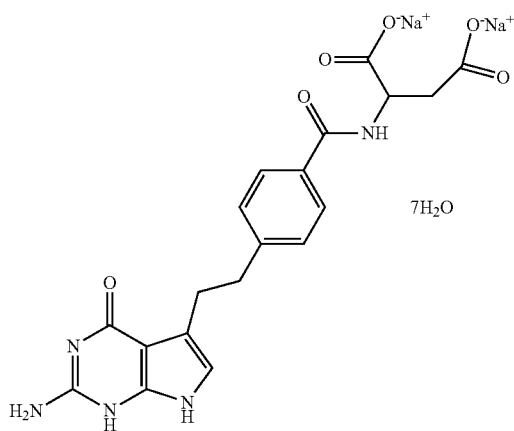

In certain embodiments, an antibody or antigen-binding fragment provided herein is linked to or in combination with camptothecin (Beisler 1971; Stork 1971). Camptothecin has the structure:

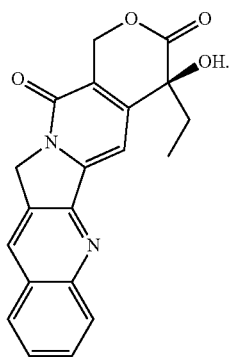

In certain embodiments, an antibody or antigen-binding fragment provided herein is linked to or in combination with irinotecan (sold as Camptosar®; Pharmacia & Upjohn Co.; Kalamazoo, Mich.); a combination of irinotecan, 5-fluorouracil, and leucovorin; or PEG-labeled irinotecan. Irinotecan has the structure:

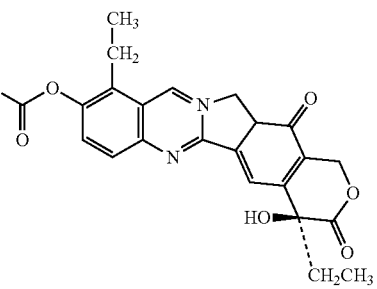

In certain embodiments, an antibody or antigen-binding fragment provided herein is associated with the FOLFOX regimen, which consists of oxaliplatin together with infusional fluorouracil and folinic acid (Chaouche 2000; de Gramont 2000). Oxaliplatin has the structure:

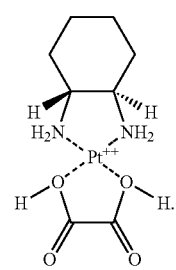

In certain embodiments, an antibody or antigen-binding fragment provided herein is linked to or in combination with an antiestrogen such as tamoxifen sold as Nolvadex® by AstraZeneca Pharmaceuticals LP; Wilmington, Del.) or toremifene citrate (sold as Fareston® by Shire US, Inc.; Florence, Ky.). Tamoxifen has the structure:

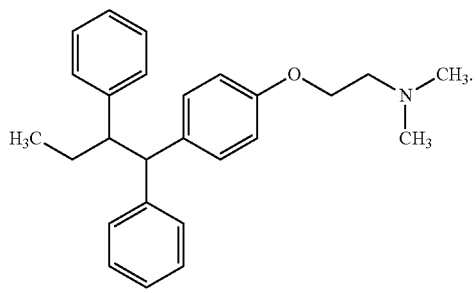

Toremifene citrate has the structure:

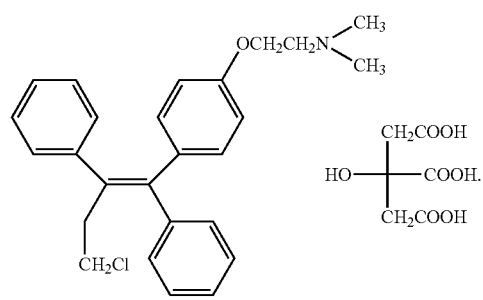

In certain embodiments, an antibody or antigen-binding fragment provided herein is linked to or in combination with an aromatase inhibitor such as anastrazole (sold as Arimidex® by AstraZeneca Pharmaceuticals LP; Wilmington, Del.), exemestane (sold as Aromasin® by Pharmacia Corporation; Kalamazoo, Mich.), or letrozole (sold as Femara® by Novartis Pharmaceuticals Corporation; East Hanover, N.J.). Anastrazole has the structure:

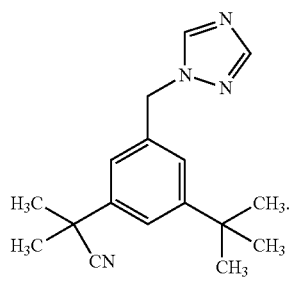

Exemestane has the structure:

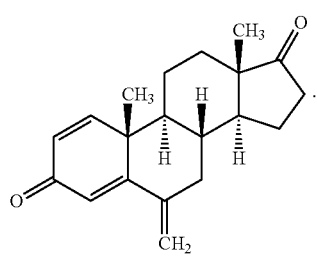

Letrozole has the structure:

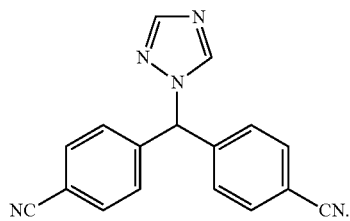

In certain embodiments, an antibody or antigen-binding fragment provided herein is linked to or in combination with an estrogen such as diethylstilbestrol (DES), estradiol (sold as Estrol® by Warner Chilcott, Inc.; Rockaway, N.J.), or conjugated estrogens (sold as Premarin® by Wyeth Pharmaceuticals Inc., Philadelphia, Pa.). DES has the structure:

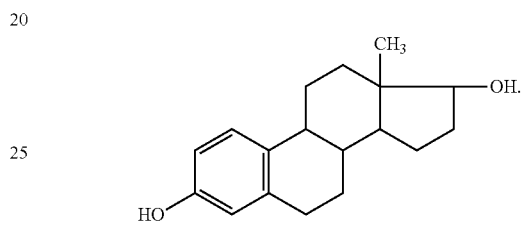

In certain embodiments, an antibody or antigen-binding fragment provided herein is linked to or in combination with an anti-angiogenic agent such as Bevacizumab, VEGFR-2 antibody IMC-1C11, other VEGF-R inhibitors such as CHIR-258, Vatalanib (PTK/ZK; CGP-79787; ZK-222584), AG-013736, 3-[5-(methylsulfonylpiperadinemethyl)-indolyl]-quinolone, or the VEGF trap (AVE-0005), a soluble decoy receptor comprising portions of VEGF receptors 1 and 2. CHIR-258 has the structure:

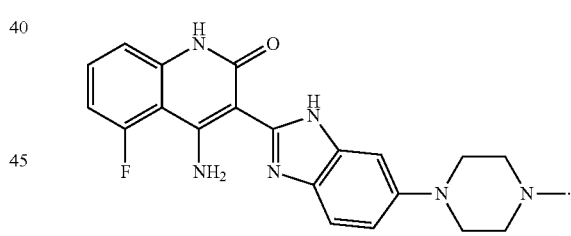

Vatalanib has the structure:

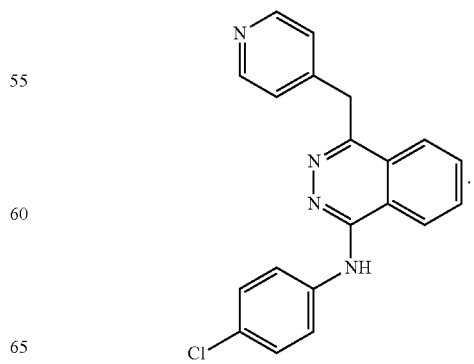

AG-013736 has the structure:

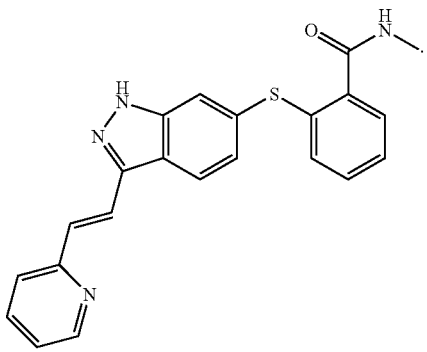

In certain embodiments, an antibody or antigen-binding fragment provided herein is linked to or in combination with an anti-angiogenic agent having the core structure set forth in WO2004/13145:

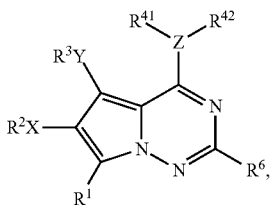

WO2004/09542:

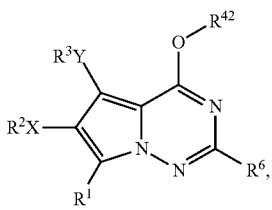

WO00/71129:

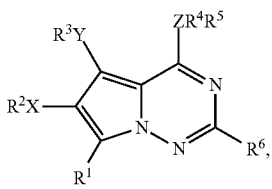

WO2004/09601:

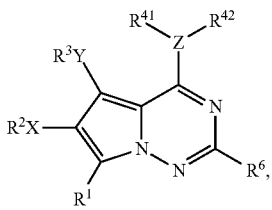

WO2004/0105:

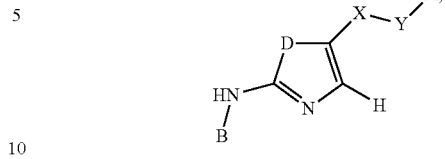

WO01/29025:

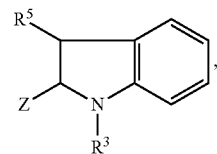

WO02/32861:

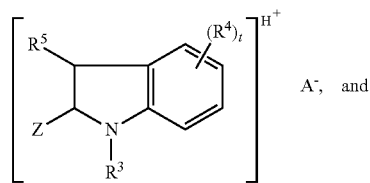

WO03/88900:

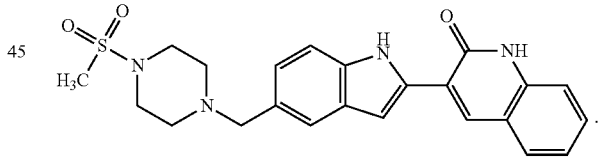

In certain embodiments, an antibody or antigen-binding fragment provided herein is linked to or in combination with a luteinizing hormone-releasing hormone (LHRH) or gonadotrophin releasing hormone (GnRH) agonist such as an goserelin acetate (sold as Zoladex® by AstraZeneca UK Limited; Macclesfield, England), leuprolide acetate (sold as Eligard® by Sanofi-Synthelabo Inc.; New York, N.Y.), or triptorelin pamoate (sold as Trelstar® by Pharmacia Company, Kalamazoo, Mich.).

Goserelin acetate is an acetate salt of [D-Ser(Bu$^t$)$^6$, Azgly$^{10}$]LHRH with the chemical name pyro-Glu-His-Trp-Ser-Tyr-D-Ser(Bu$^t$)-Leu-Arg-Pro-Azgly-NH$_2$ acetate [$C_{59}H_{84}N_{18}O_{14}$·$C_2H_4O_2$)$_x$, where x=1 to 2.4]). The structure of goserelin acetate is:

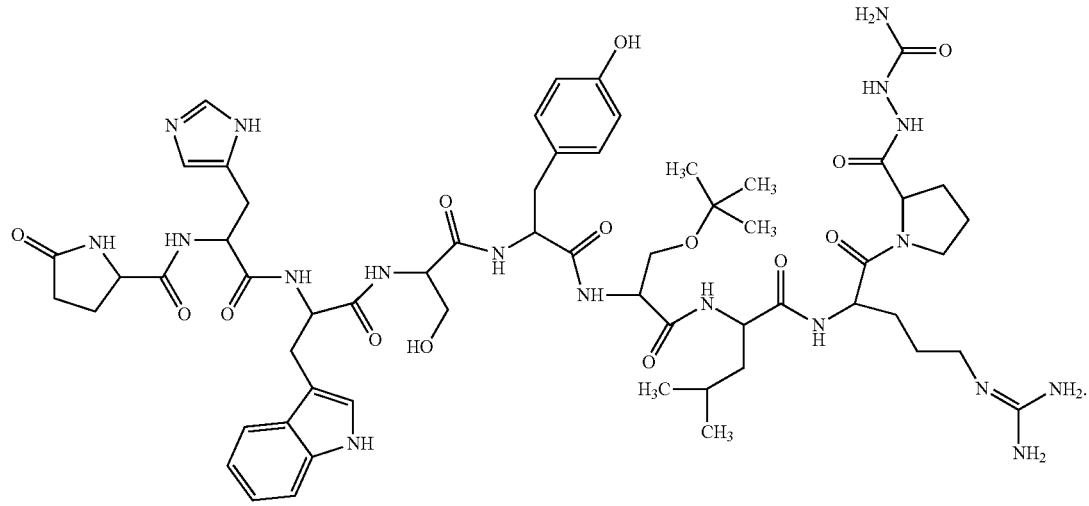
Leuprolide acetate is a synthetic nonapeptide of LHRH with the chemical name 5-oxo-L-prolyl-L-histidyl-L-tryptophyl-L-seryl-L-tyrosyl-D-leucyl-L-leucyl-L-arginyl-N-ethyl-L-prolinamide acetate (salt). The structure of leuprolide acetate is:
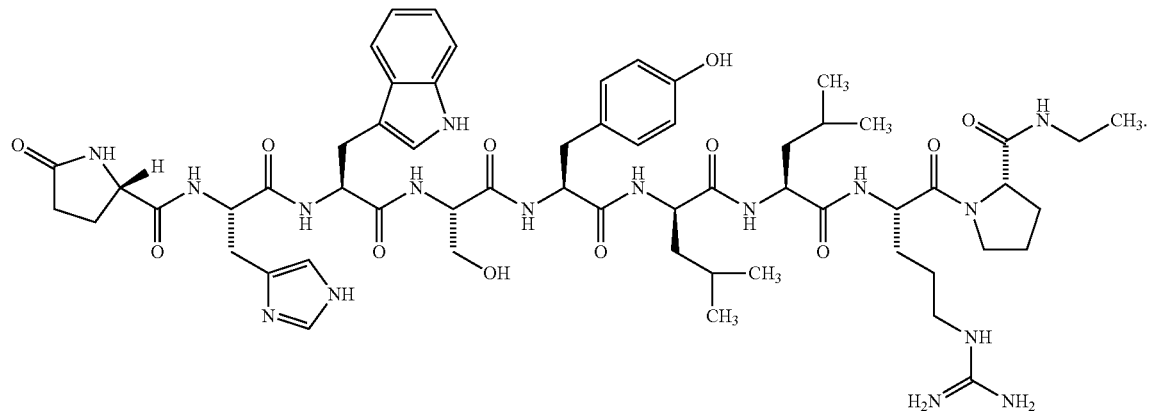
Triptorelin pamoate has the structure:
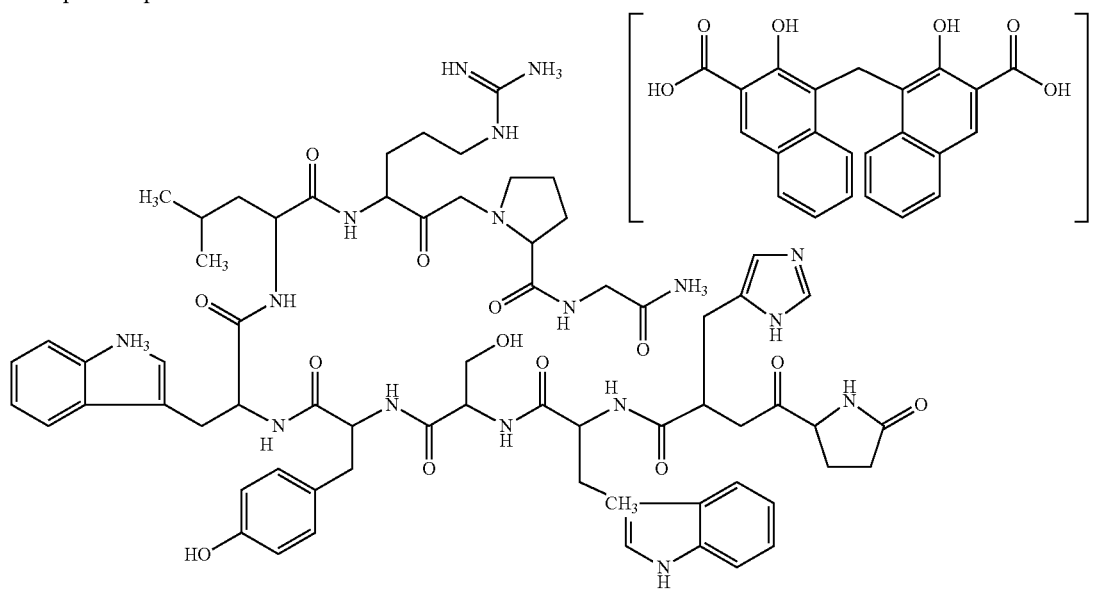

In certain embodiments, an antibody or antigen-binding fragment provided herein is linked to or in combination with sunitinib or sunitinib malate. Sunitinib has the structure:

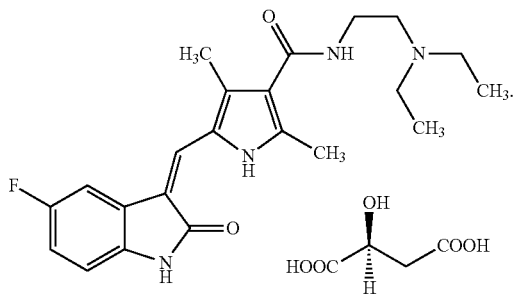

In certain embodiments, an antibody or antigen-binding fragment provided herein is linked to or in combination with a progestational agent such as medroxyprogesterone acetate (sold as Provera® by Pharmacia & Upjohn Co.; Kalamazoo, Mich.), hydroxyprogesterone caproate (17-((1-Oxohexyl)oxy)pregn-4-ene-3,20-dione)), megestrol acetate, or progestins. Medroxyprogesterone acetate has the structure:

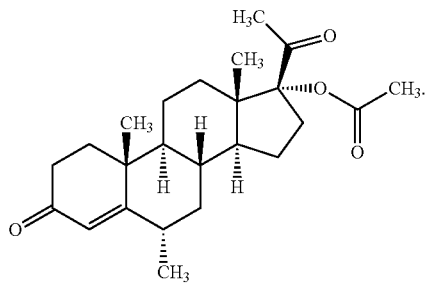

Hydroxyprogesterone caproate has the structure:

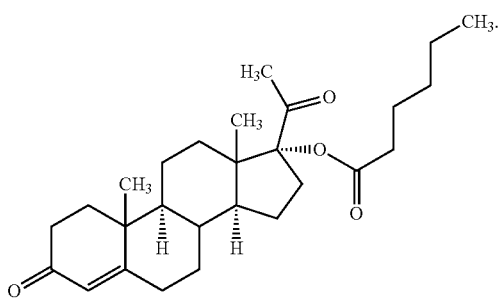

In certain embodiments, an antibody or antigen-binding fragment provided herein is linked to or in combination with a selective estrogen receptor modulator (SERM) such as raloxifene (sold as Evista® by Eli Lilly and Company; Indianapolis, Ind.), which has the structure:

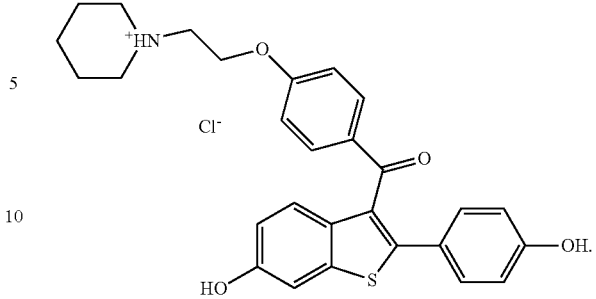

In certain embodiments, an antibody or antigen-binding fragment provided herein is linked to or in combination with an anti-androgen such as bicalutamide (sold at CASODEX® by AstraZeneca Pharmaceuticals LP; Wilmington, Del.), flutamide(2-methyl-N-[4-nitro-3 (trifluoromethyl)phenyl] propanamide; sold as Eulexin® by Schering Corporation; Kenilworth, N.J.), nilutamide (sold as Nilandron® by Aventis Pharmaceuticals Inc.; Kansas City, Mo.), or megestrol acetate (sold as Megace® by Bristol-Myers Squibb). Bicalutamide has the structure:

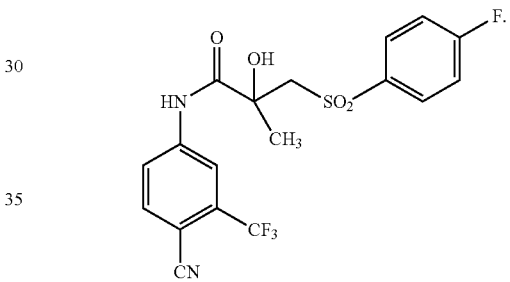

Flutamide has the structure:

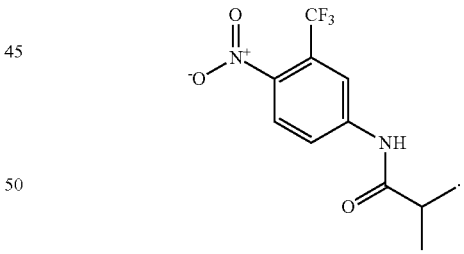

Nilutamide has the structure:

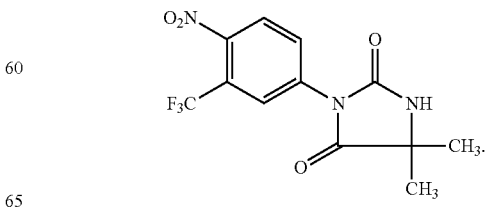

Megestrol acetate has the structure:

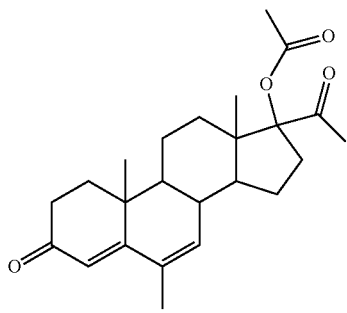

In certain embodiments, an antibody or antigen-binding fragment provided herein is linked to or in combination with one or more inhibitors that antagonize the action of the EGF Receptor or HER2, such as CP-724714, TAK-165 (mubritinib), HKI-272, OSI-774 (erlotinib; Hidalgo 2001), lapatinib (GW2016; Rusnak 2001; N-{3-Chloro-4-[(3-fluorobenzyl)oxy]phenyl}-6-[5-({[2-(methylsulfonyl)ethyl]amino}methyl)-2-furyl]-4-quinazolinamine; PCT Application No. WO99/35146), canertinib (CI-1033; Erlichman 2001; Smaill 2000), EKB-569 (Wissner 2003), PKI-166 (CGP-75166), ABX-EGF antibody (Abgenix, Inc., Freemont, Calif.; Yang 1999; Yang 2001), erbitux (IMC-C225, cetuximab; U.S. Pat. No. 6,217,866; Imclone, New York, N.Y.), GW-572016, or any anti-EGFR or anti-HER2 antibody.

CP-724714 has the structure:

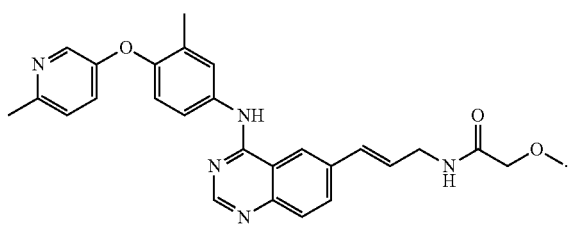

TAK-165 (mubritinib) has the structure:

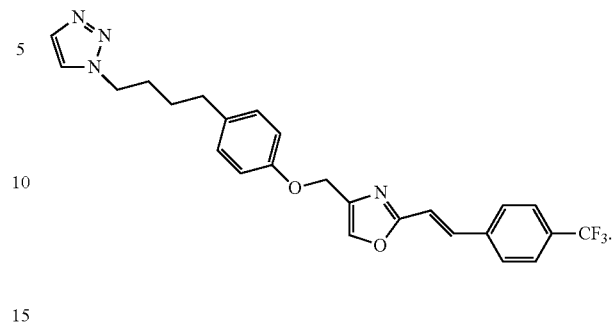

HKI-272 has the structure:

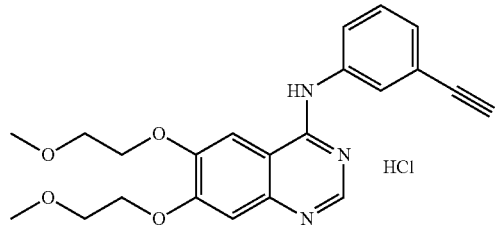

OSI-774 (erlotinib) has the structure:

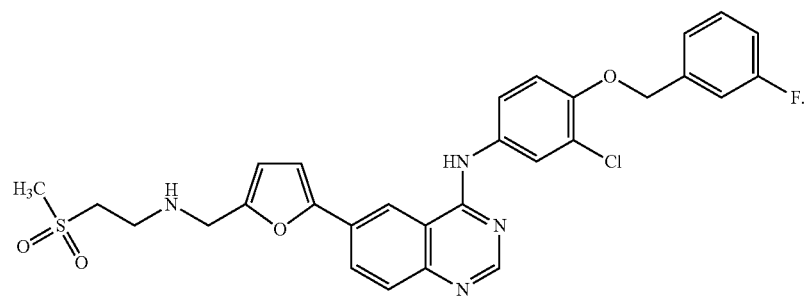

Lapatinib has the structure:

Canertinib has the structure:

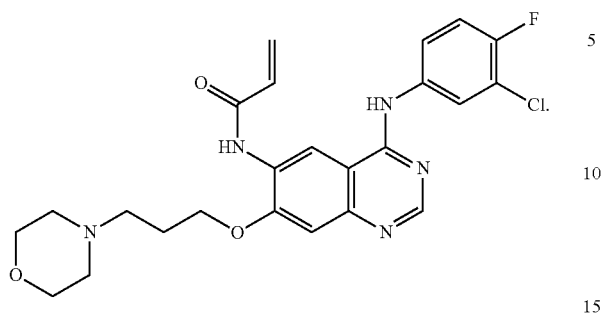

EKB-569 has the structure:

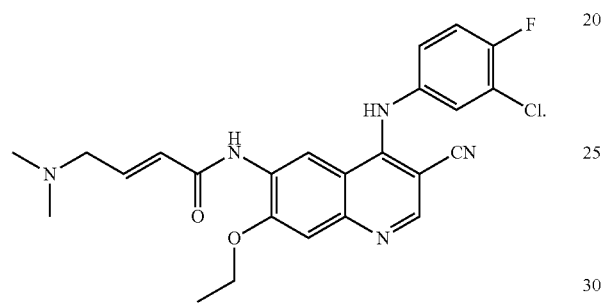

PKI-166 has the structure:

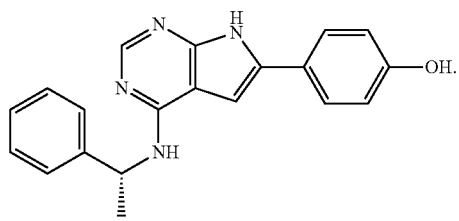

In certain embodiments, an antibody or antigen-binding fragment provided herein is linked to or in combination with lonafarnib (sold as Sarasar® by Schering-Plough, Kenilworth, N.J.), which has the structure:

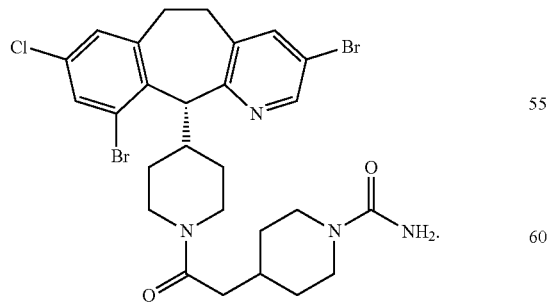

In certain embodiments, an antibody or antigen-binding fragment provided herein is linked to or in combination with an FPT inhibitor having the structure:

![structure]

or

![structure]

In other embodiments, an antibody or antigen-binding fragment provided herein is linked to or in combination with an FPT inhibitor such as BMS-214662 (Hunt 2000; Dancey 2002; (R)-7-cyano-2,3,4,5-tetrahydro-1-(1H-imidazol-4-yl-methyl)-3-(phenylmethyl)-4-(2-thienylsulfonyl)-1H-1,4-benzodiazepine) or R155777 (tipifarnib; Garner 2002; Dancey 2002; (B)-6-[amino(4-chlorophenyl)(1-methyl-1H-imidazol-5-yl)-methyl]-4-(3-chlorophenyl)-1-methyl-2 (1H)-quinolinone]; sold as Zarnestra® by Johnson & Johnson, New Brunswick, N.J.). BMS-214662 has the structure:

![structure]

R155777 has the structure:

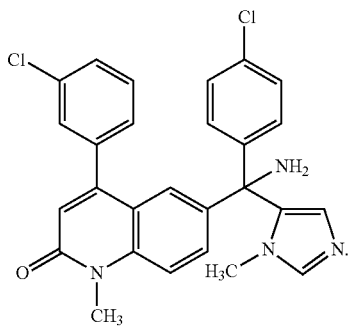

In certain embodiments, an antibody or antigen-binding fragment provided herein is linked to or in combination with amifostine, NVP-LAQ824 (Atadja 2004), suberoyl analide hydroxamic acid, valproic acid (Michaelis 2004), trichostatin A, FK-228 (Furumai 2002), SU11248 (Mendel 2003), BAY43-9006 (sorafenib), KRN951, aminoglutethimide, amsacrine, anagrelide, anastrozole (sold as Arimidex® by AstraZeneca Pharmaceuticals LP, Wilmington, Del.), asparaginase, bacillus Calmette-Guerin (BCG) vaccine (Gamido 1997), bleomycin, buserelin, busulfan (1,4-butanediol dimethanesulfonate; sold as Busulfex® by ESP Pharma, Inc., Edison, N.J.), satraplatin, carboplatin (sold as Paraplatin® by Bristol-Myers Squibb, Princeton, N.J.), carmustine, chlorambucil, cisplatin, cladribine, clodronate, cyclophosphamide, cyproterone, cytarabine, dacarbazine, dactinomycin, daunorubicin, diethylstilbestrol, epirubicin, fludarabine, fludrocortisone, fluoxymesterone, flutamide, hydroxyurea, idarubicin, ifosfamide, imatinib (sold as Gleevec® by Novartis Pharmaceuticals Corporation, East Hanover, N.J.), leucovorin, leuprolide, levamisole, lomustine, mechlorethamine, melphalan (sold as Alkeran® by Celgene Corporation, Warren, N.J.), mercaptopurine, mesna, methotrexate, mitomycin, mitotane, mitoxantrone, nilutamide, octreotide (Katz 1989; sold as Sandostatin LAR® Depot by Novartis Pharm Corp., E. Hanover, N.J.), edotreotide (yttrium-90 labeled or unlabeled), oxaliplatin (sold as Eloxatin® by Sanofi-Synthelabo Inc., New York, N.Y.), pamidronate (sold as Aredia® by Novartis Pharmaceuticals Corp., East Hanover, N.J.), Pentostatin (sold as Nipent® by Supergen, Dublin, Calif.), plicamycin, porfimer (sold as Photofrin® by Axcan Scandipharm Inc., Birmingham, Ala.), procarbazine, raltitrexed, rituximab (sold as Rituxan® by Genentech, Inc.; South San Francisco, Calif.), streptozocin, teniposide, testosterone, thalidomide, thalidomide combined with dexamethasone, thioguanine, thiotepa, tretinoin, vindesine, all trans-retinoic acid, or 13-cis-retinoic acid. Amifostine has the structure:

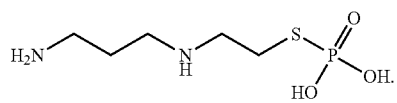

NVP-LAQ824 has the structure:

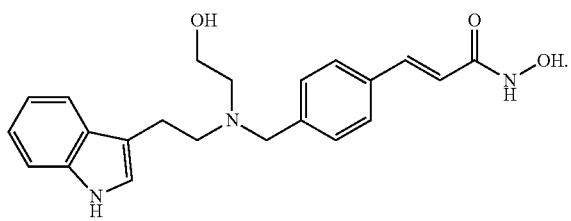

Suberoyl analide hydroxamic acid has the structure:

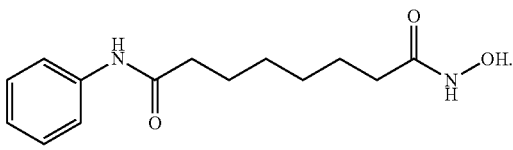

Valproic acid has the structure:

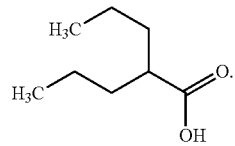

Trichostatin A has the structure:

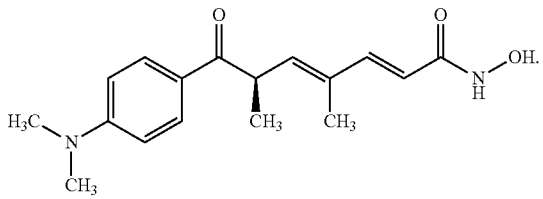

FK-228 has the structure:

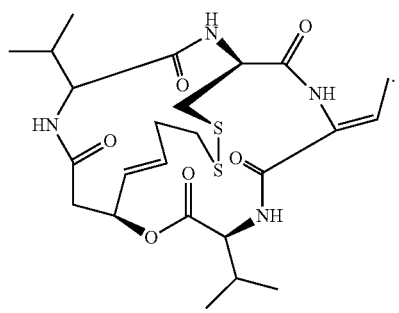

SU11248 has the structure:

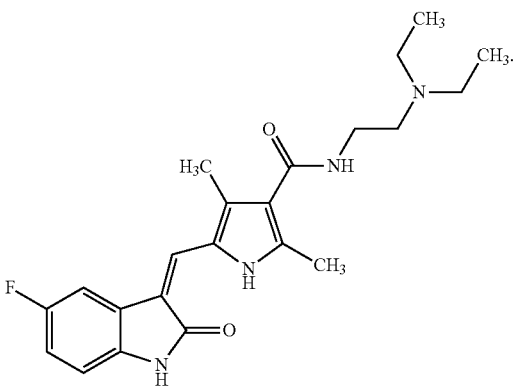

BAY43-9006 has the structure:
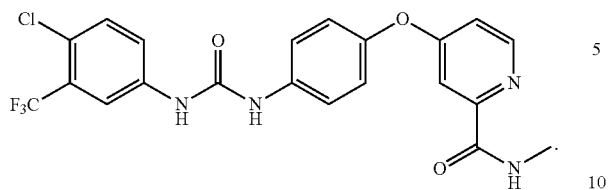
KRN951 has the structure:
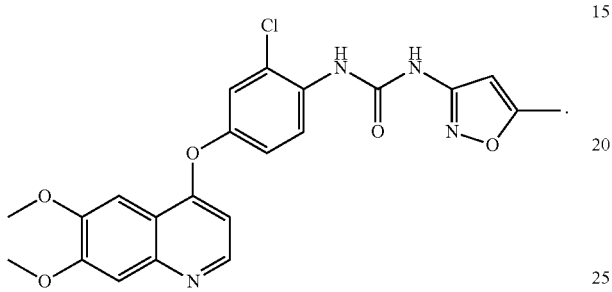
Aminoglutethimide has the structure:
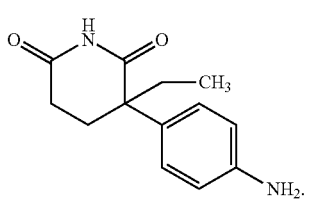
Amsacrine has the structure:
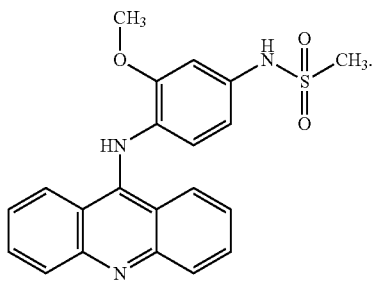
Anagrelide has the structure:
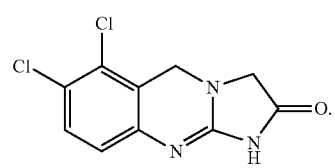
Anastrozole has the structure:
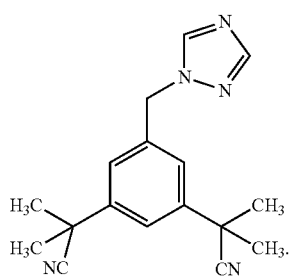
Bleomycin has the structure:
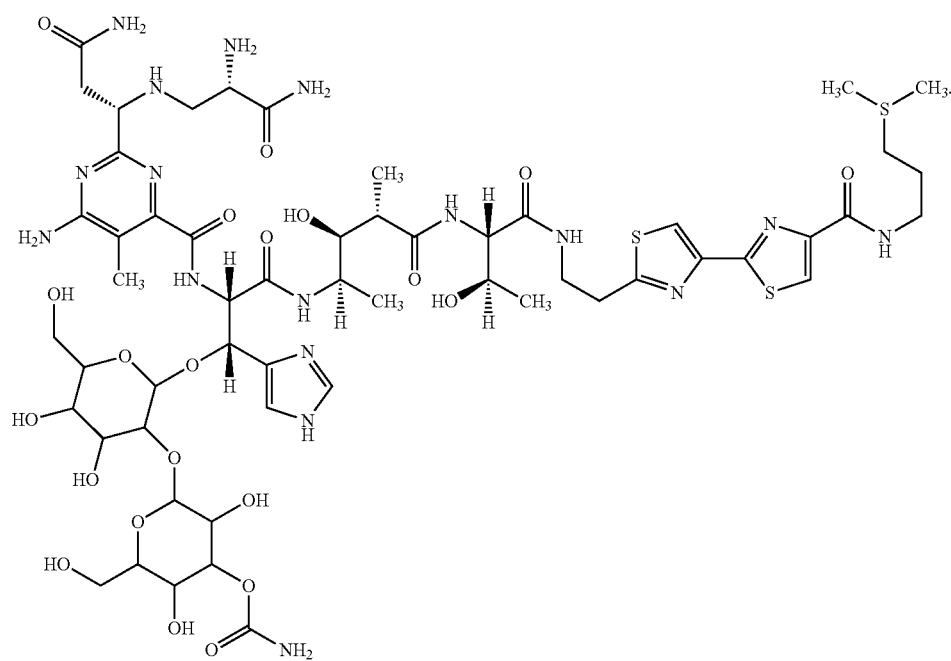

Buserelin has the structure:
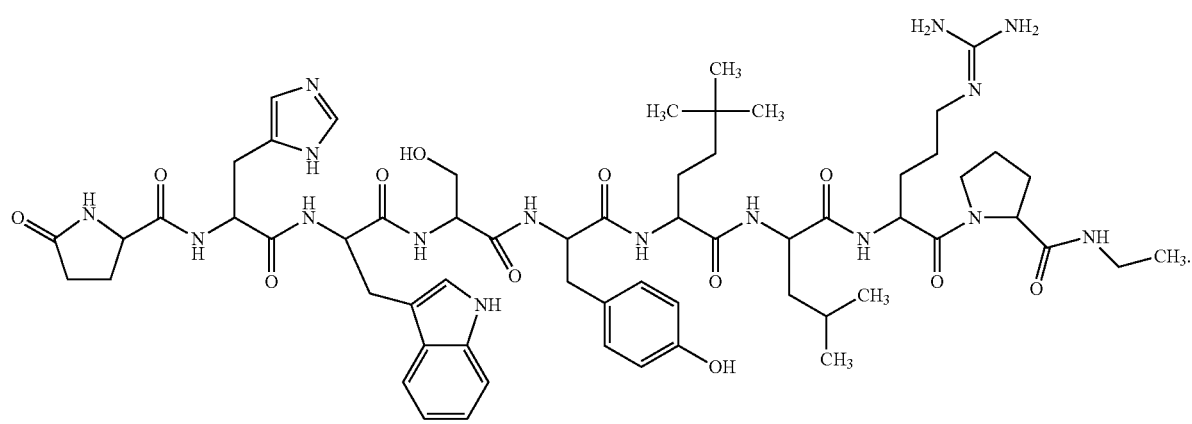
Busulfan has the structure:
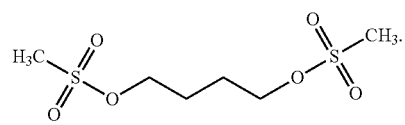
Carboplatin has the structure:
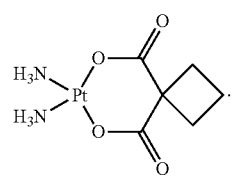
Carmustine has the structure:
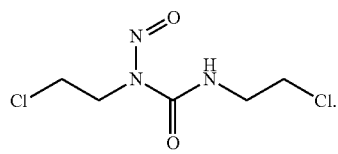
Chlorambucil has the structure:
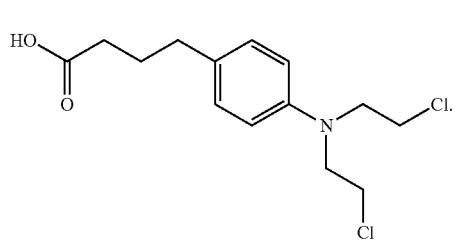
Cisplatin has the structure:
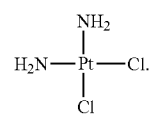
Cladribine has the structure:
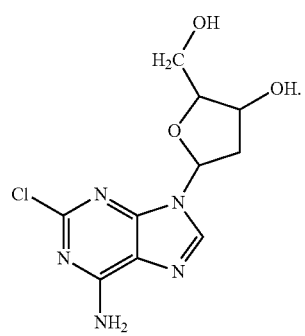
Clodronate has the structure:
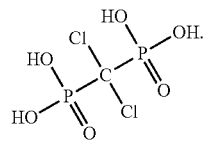
Cyclophosphamide has the structure:
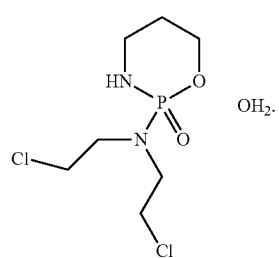

51
Cyproterone has the structure:
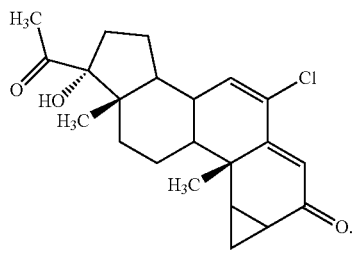
Cytarabine has the structure:
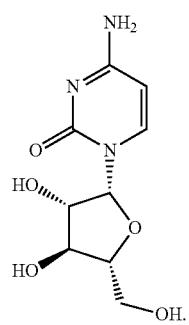
Dacarbazine has the structure:
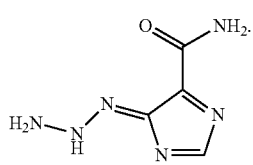
Dactinomycin has the structure:
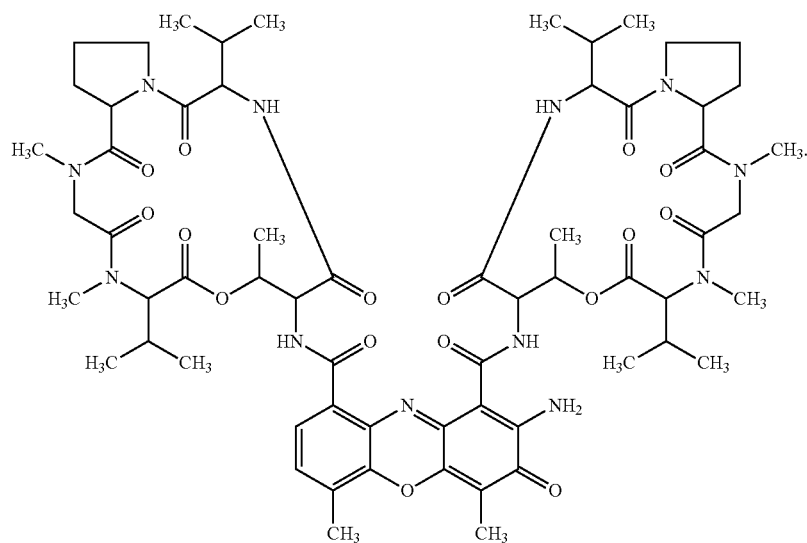
52
Daunorubicin has the structure:
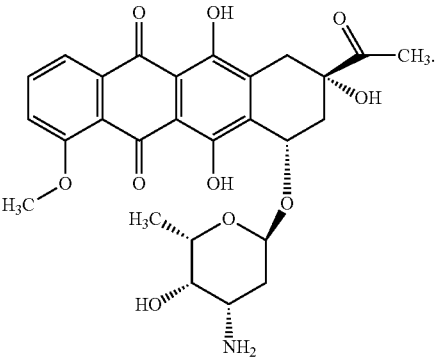
Diethylstilbestrol has the structure:
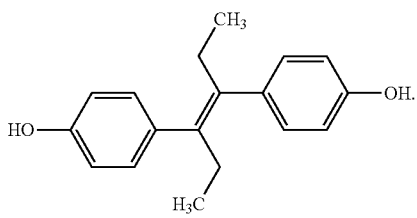
Epirubicin has the structure:
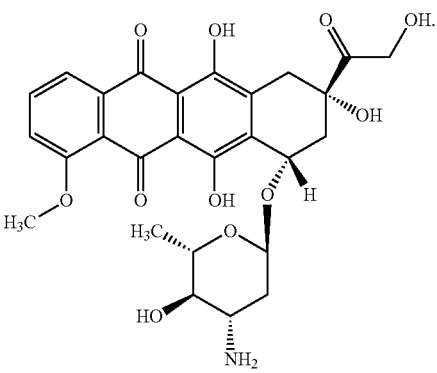

Fludarabine has the structure:
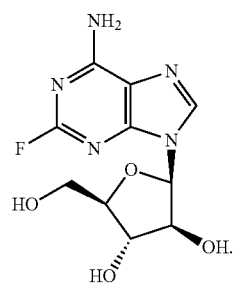
Fludrocortisone has the structure:
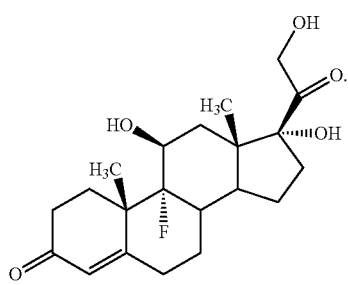
Fluoxymesterone has the structure:
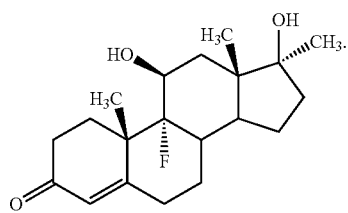
Flutamide has the structure:
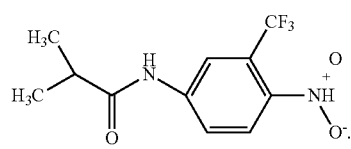
Hydroxyurea has the structure:
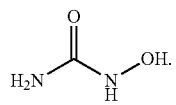
Idarubicin has the structure:
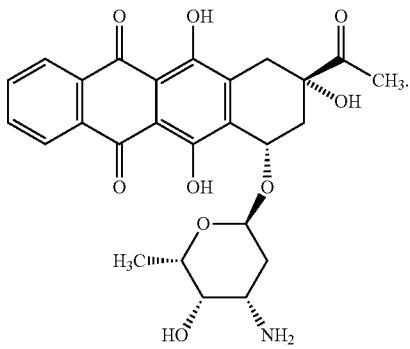
Ifosfamide has the structure:
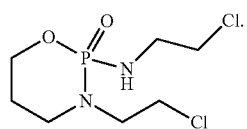
Imatinib has the structure:
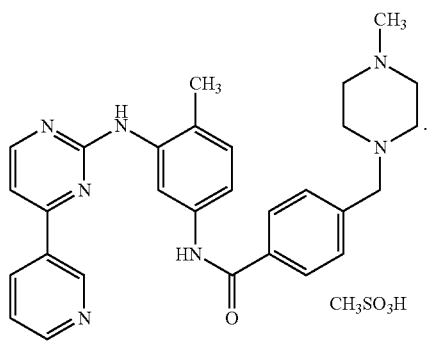
Leucovorin has the structure:
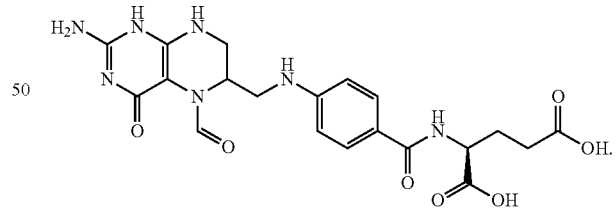
Leuprolide has the structure:
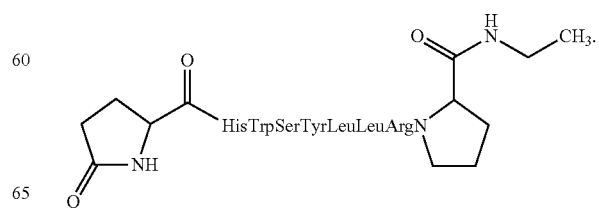

Levamisole has the structure:

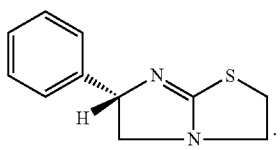

Lomustine has the structure:

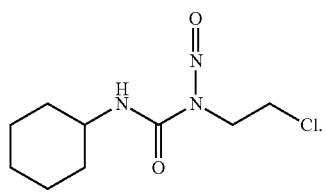

Mechlorethamine has the structure:

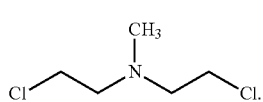

Melphalan has the structure:

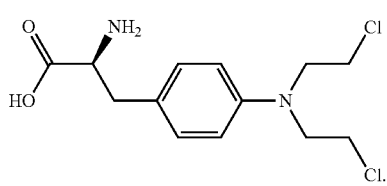

Mercaptopurine has the structure:

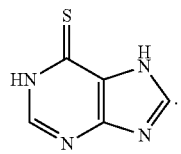

Mesna has the structure:

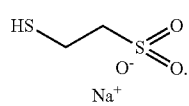

Methotrexate has the structure:

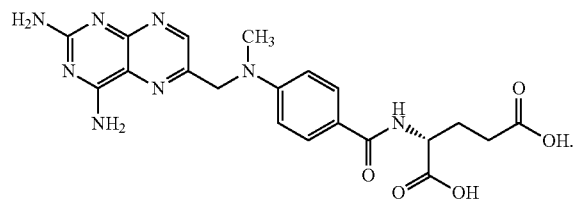

Mitomycin has the structure:

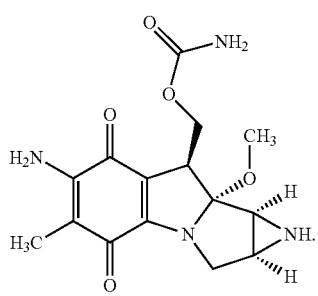

Mitotane has the structure:

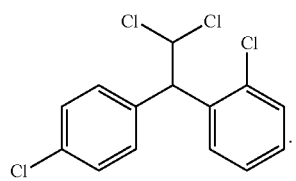

Mitoxantrone has the structure:

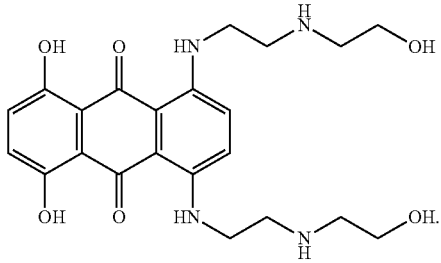

Nilutamide has the structure:

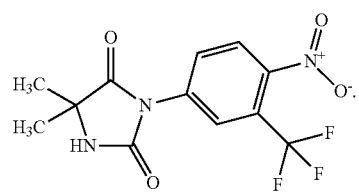

Octreotide has the structure:

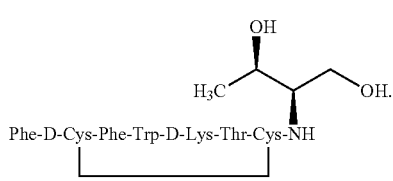

Oxaliplatin has the structure:
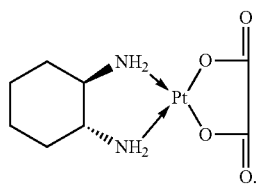
Pamidronate has the structure:
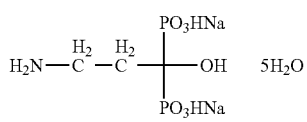
Pentostatin has the structure:
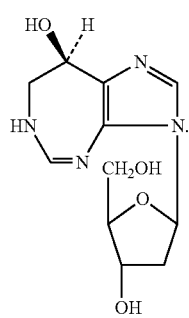
Porfimer has the structure:
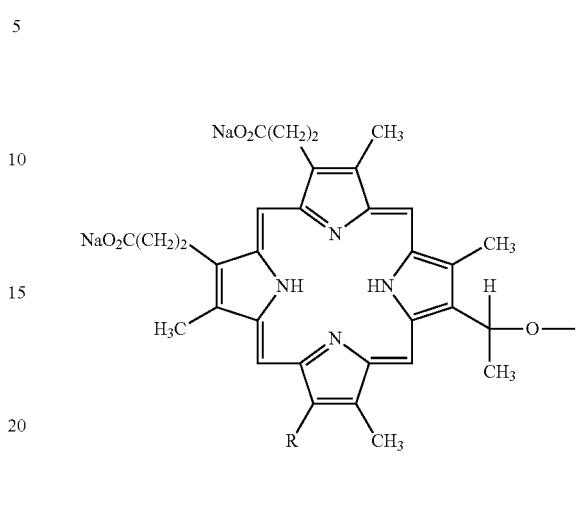
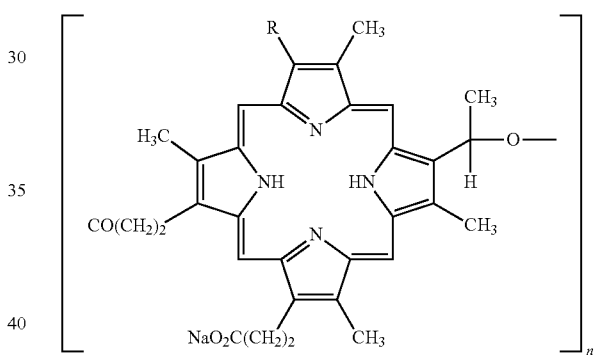
Plicamycin has the structure:
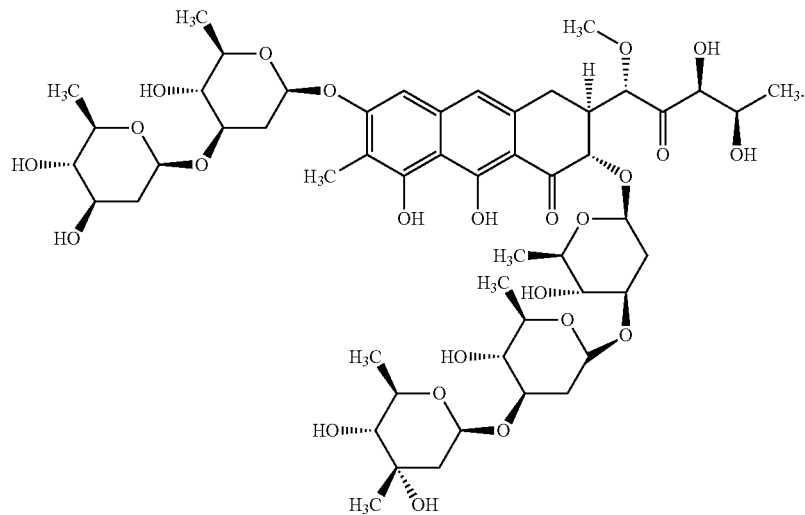

-continued
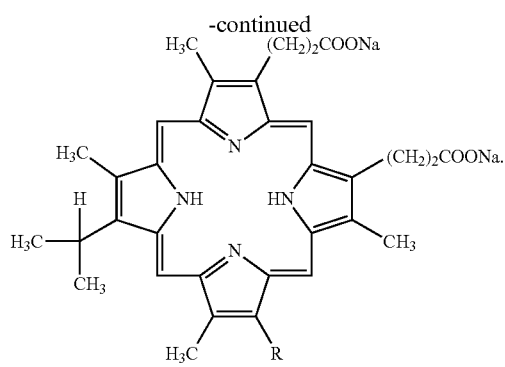
n = 0-6
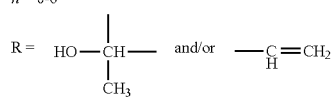
Procarbazine has the structure:
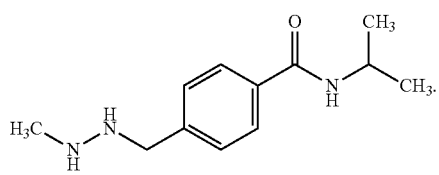
Raltitrexed has the structure:
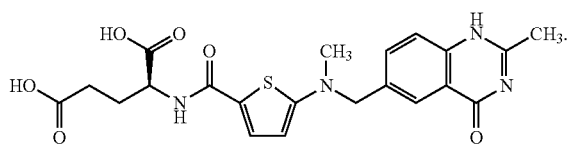
Streptozocin has the structure:
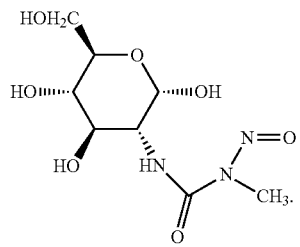
Teniposide has the structure:
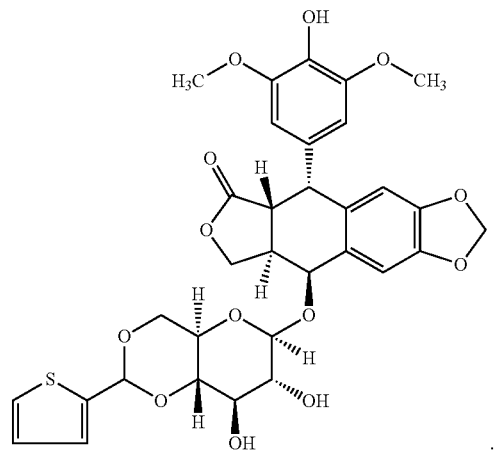
Testosterone has the structure:
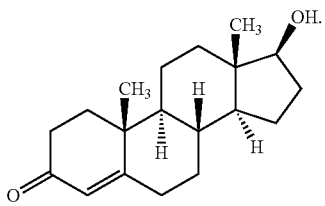
Thalidomide has the structure:
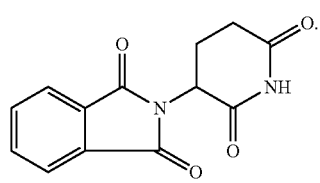
Thioguanine has the structure:
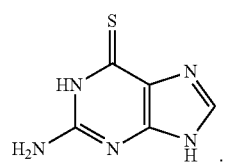
Thiotepa has the structure:
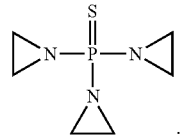
Tretinoin has the structure:
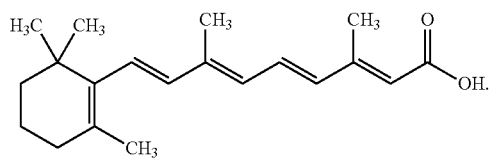
Vindesine has the structure:
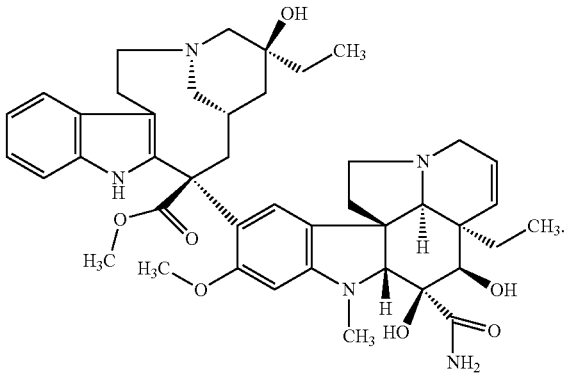

13-cis-retinoic acid has the structure:

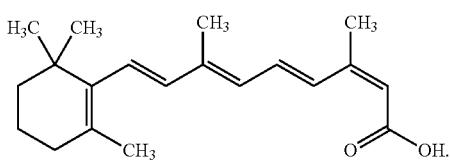

In certain embodiments, an antibody or antigen-binding fragment provided herein is linked to or used in combination with abraxane. Abraxane is an injectable suspension of paclitaxel protein-bound particles comprising an albumin-bound form of paclitaxel with a mean particle size of approximately 130 nanometers. Abraxane is supplied as a white to yellow, sterile, lyophilized powder for reconstitution with 20 mL of 0.9% Sodium Chloride Injection, USP prior to intravenous infusion. Each single-use vial contains 100 mg of paclitaxel and approximately 900 mg of human albumin. Each milliliter (mL) of reconstituted suspension contains 5 mg paclitaxel. Abraxane is free of solvents and cremophor (polyoxyethylated castor oil).

In certain embodiments, an antibody or antigen-binding fragment provided herein is linked to or in combination with one or more of phenylalanine mustard, uracil mustard, estramustine, altretamine, floxuridine, 5-deooxyuridine, cytosine arabinoside, 6-mercaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin, diftitox, gefitinib, bortezimib, paclitaxel, docetaxel, epithilone B, BMS-247550 (Lee 2001), BMS-310705, droloxifene (3-hydroxytamoxifen), 4-hydroxytamoxifen, pipendoxifene, ERA-923, arzoxifene, fulvestrant, acolbifene, lasofoxifene (CP-336156), idoxifene, TSE-424, HMR-3339, ZK186619, topotecan, PTK787/ZK 222584 (Thomas 2003), VX-745 (Haddad 2001), PD 184352 (Sebolt-Leopold 1999), LY294002, LY292223, LY292696, LY293684, LY293646 (Vlahos 1994), wortmannin, BAY-43-9006, (Wilhelm 2002), ZM336372, L-779,450, a Raf inhibitor (Lowinger 2002), flavopiridol (L86-8275/HMR 1275; Senderowicz 2000), UCN-01 (7-hydroxy staurosporine; Senderowicz 2000), any mTOR inhibitor, rapamycin (sirolimus), everolimus (40-O-(2-hydroxyethyl) derivative of rapamycin), CCI-779 (temsirolimus; Sehgal 1994; Elit 2002), AP-23573, RAD001, ABT-578, or BC-210. Rapamycin (sirolimus) has the structure:

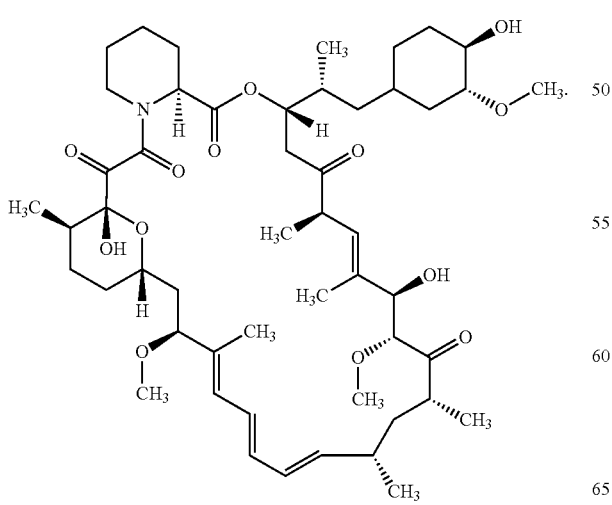

CCI-779 has the structure:

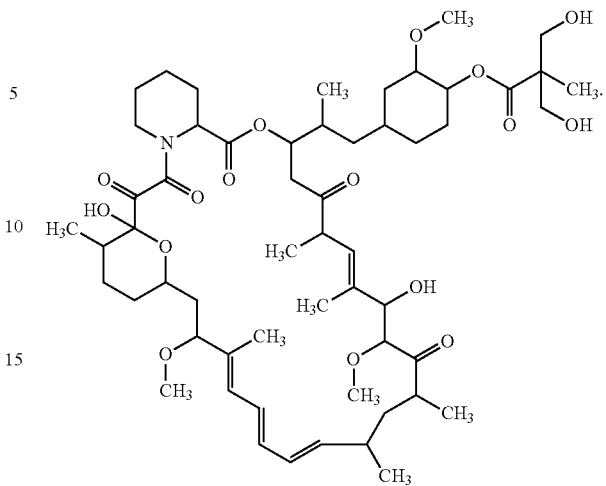

AP-23573 has the structure:

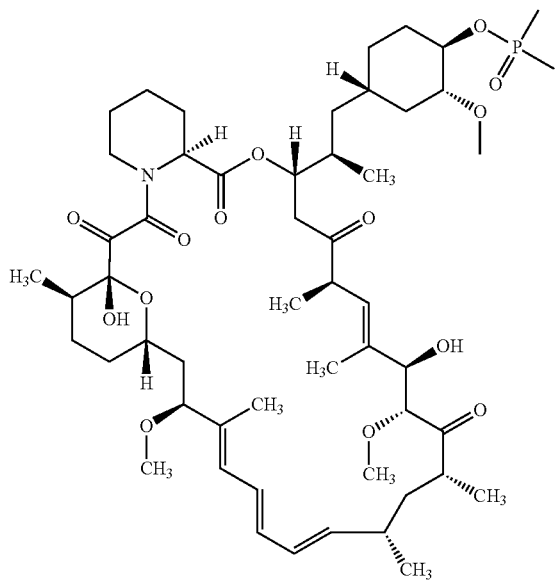

RAD001 has the structure:

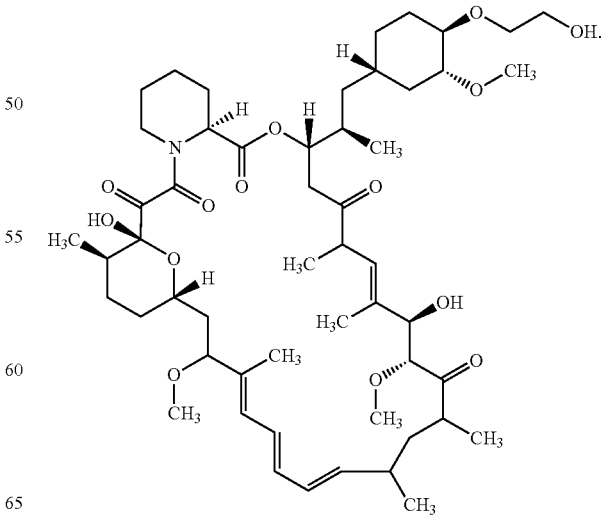

ABT-578 has the structure:

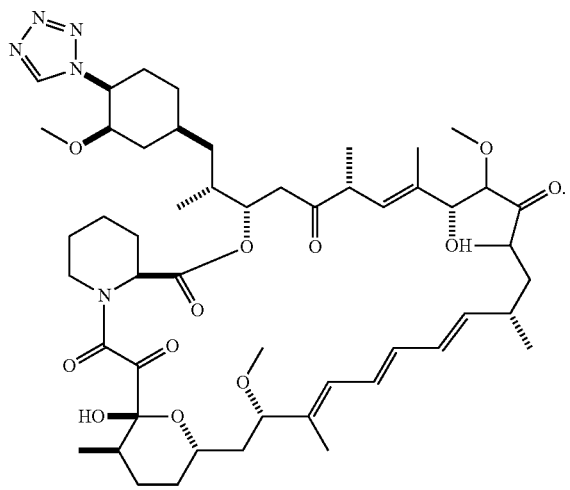

BC-210 has the structure:

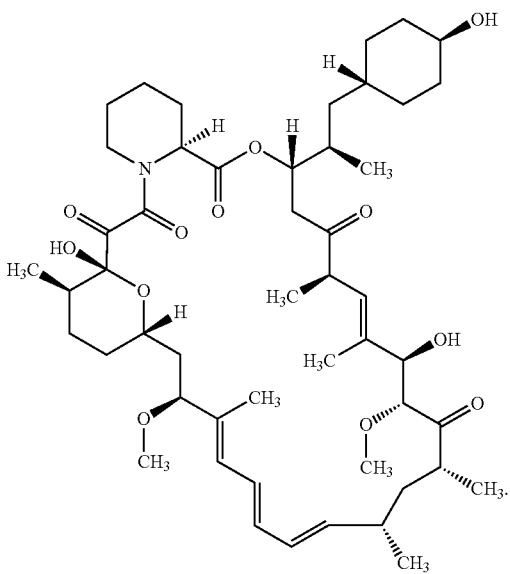

In certain embodiments, an antibody or antigen-binding fragment provided herein is linked to or in combination with one or more of the compounds set forth in U.S. Pat. No. 5,656,655, which discloses styryl substituted heteroaryl EGFR inhibitors; U.S. Pat. No. 5,646,153, which discloses bis mono and/or bicyclic aryl heteroaryl carbocyclic and heterocarbocyclic EGFR and PDGFR inhibitors; U.S. Pat. No. 5,679,683, which discloses tricyclic pyrimidine compounds that inhibit the EGFR; U.S. Pat. No. 5,616,582, which discloses quinazoline derivatives that have receptor tyrosine kinase inhibitory activity; Fry 1994, which discloses a compound having a structure that inhibits EGFR (see FIG. 1 of Fry 1994); U.S. Pat. No. 5,196,446, which discloses heteroarylethenediyl or heteroarylethenediylaryl compounds that inhibit EGFR; and Panek 1997, which discloses a compound identified as PD166285 (6-(2,6-dichlorophenyl)-2-(4-(2-diethylaminoethoxy)phenylamino)-8-methyl-8H-pyrido (2,3-d)pyrimidin-7-one) that inhibits the EGFR, PDGFR, and FGFR families of receptors.

In certain embodiments, an antibody or antigen-binding fragment provided herein is linked to or in combination with one or more of pegylated or unpegylated interferon alfa-2a, pegylated or unpegylated interferon alfa-2b, pegylated or unpegylated interferon alfa-2c, pegylated or unpegylated interferon alfa n-1, pegylated or unpegylated interferon alfa n-3, and pegylated, unpegylated consensus interferon or albumin-interferon-alpha.

Other interferon alpha conjugates can be prepared by coupling an interferon alpha to a water-soluble polymer. A nonlimiting list of such polymers includes other polyalkylene oxide homopolymers such as polypropylene glycols, polyoxyethylenated polyols, copolymers thereof and block copolymers thereof. As an alternative to polyalkylene oxide-based polymers, effectively non-antigenic materials such as dextran, polyvinylpyrrolidones, polyacrylamides, polyvinyl alcohols, carbohydrate-based polymers and the like can be used. Such interferon alpha-polymer conjugates are described, for example, in U.S. Pat. No. 4,766,106, U.S. Pat. No. 4,917,888, EP Application No. 0236987 or 0593868, and International Publication No. WO95/13090. A PEG12000-IFN alfa 2b can be prepared by attaching in a PEG polymer to a histidine residue in the interferon alfa-2b molecule.

Pharmaceutical compositions of pegylated interferon alpha suitable for parenteral administration can be formulated with a suitable buffer, e.g., Tris-HCl, acetate or phosphate such as dibasic sodium phosphate/monobasic sodium phosphate buffer, and pharmaceutically acceptable excipients (e.g., sucrose), carriers (e.g. human plasma albumin), toxicity agents (e.g., NaCl), preservatives (e.g., thimerosol, cresol or benzyl alcohol), and surfactants (e.g., tween or polysorbates) in sterile water for injection. The pegylated interferon alpha can be stored as lyophilized powder under refrigeration at 2°-8° C. The reconstituted aqueous solutions are stable when stored between 2° and 8° C. and used within 24 hours of reconstitution (see, e.g., U.S. Pat. Nos. 4,492,537; 5,762,923 and 5,766,582. The reconstituted aqueous solutions may also be stored in pre-filled, multi-dose syringes such as those useful for delivery of drugs such as insulin. Typical, suitable syringes include systems comprising a prefilled vial attached to a pen-type syringe such as the NOVOLET® Novo Pen available from Novo Nordisk or the REDIPEN®, available from Schering Corporation, Kenilworth, N.J. Other syringe systems include a pen-type syringe comprising a glass cartridge containing a diluent and lyophilized pegylated interferon alpha powder in a separate compartment.

Compositions comprising an antiemetic are useful for preventing or treating nausea; a common side effect of chemotherapy. Accordingly, in certain embodiments compositions are provided that comprise an antibody or antigen-binding fragment provided herein linked to or in combination with one or more anti-cancer chemotherapeutic agents and one or more antiemetics, including but not limited to casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co.; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), prednisolone, methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.). Also provided herein are methods of treating cancer by administering such compositions to a subject (e.g., a mammalian subject such as a human, primate, canine, rat, rabbit, or mouse) in need thereof.

Other side effects of cancer treatment include red and white blood cell deficiency. Accordingly, compositions are provided that comprise an antibody or antigen-binding fragment provided herein linked to or in combination with an agent that treats red and/or white blood cell deficiency such as pegfilgrastim, erythropoietin, epoetin alfa, or darbepoetin alfa.

In certain embodiments, compositions are provided that comprise an antibody or antigen-binding fragment thereof linked to or in combination with one or more anti-hypertensive agents such as a diuretic, an adrenergic receptor antagonist, an adrenergic receptor agonist, a calcium channel blockers, an ACE inhibitor, an angiotensin II receptor antagonist, an aldosterone antagonist, a vasodilator, or a centrally acting adrenergic drug.

In certain embodiments, the antibodies or antigen-binding fragments disclosed herein may be administered as part of a pharmaceutical composition that comprises one or more physiologically tolerable components. Therefore, in certain embodiments, such compositions and methods of formulating such compositions are provided herein. Compositions comprising one or more antibodies or antigen-binding fragments as disclosed herein and one or more physiologically tolerable components may be used in the treatment of diseases associated with high VEGF expression levels and/or signaling, and/or increased angiogenesis.

Physiologically tolerable components for use in the pharmaceutical compositions disclosed herein may include, for example, pharmaceutically acceptable liquid, gel, or solid carriers, diluents, adjuvants, excipients, or non-toxic auxiliary substances, other components known in the art, or various combinations thereof. Suitable components may include, for example, antioxidants, fillers, binders, disintegrants, buffers, preservatives, lubricants, flavorings, thickeners, coloring agents, or emulsifiers.

Suitable antioxidants may include, for example, methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate. As disclosed herein, inclusion of one or more antioxidants such as methionine in a composition comprising an antibody or antigen-binding fragment as provided herein decreases oxidation of the antibody or antigen-binding fragment. This reduction in oxidation prevents or reduces loss of binding affinity, thereby improving antibody stability and maximizing shelf-life. Therefore, in certain embodiments compositions are provided that comprise one or more antibodies or antigen-binding fragments as disclosed herein and one or more antioxidants such as methionine. Further provided are methods for preventing oxidation of, extending the shelf-life of, and/or improving the efficacy of an antibody or antigen-binding fragment as provided herein by mixing the antibody or antigen-binding fragment with one or more antioxidants such as methionine.

Suitable carriers may include, for example, aqueous vehicles such as sodium chloride injection, Ringer's injection, isotonic dextrose injection, sterile water injection, or dextrose and lactated Ringer's injection, nonaqueous vehicles such as fixed oils of vegetable origin, cottonseed oil, corn oil, sesame oil, or peanut oil, antimicrobial agents at bacteriostatic or fungistatic concentrations, isotonic agents such as sodium chloride or dextrose, buffers such as phosphate or citrate buffers, antioxidants such as sodium bisulfate, local anesthetics such as procaine hydrochloride, suspending and dispersing agents such as sodium carboxymethylcellulose, hydroxypropyl methylcellulose, or polyvinylpyrrolidone, emulsifying agents such as Polysorbate 80 (TWEEN-80), sequestering or chelating agents such as EDTA (ethylenediaminetetraacetic acid) or EGTA (ethylene glycol tetraacetic acid), ethyl alcohol, polyethylene glycol, propylene glycol, sodium hydroxide, hydrochloric acid, citric acid, or lactic acid. Antimicrobial agents utilized as carriers may be added to pharmaceutical compositions in multiple-dose containers that include phenols or cresols, mercurials, benzyl alcohol, chlorobutanol, methyl and propyl p-hydroxybenzoic acid esters, thimerosal, benzalkonium chloride and benzethonium chloride. Suitable excipients may include, for example, water, saline, dextrose, glycerol, or ethanol. Suitable nontoxic auxiliary substances may include, for example, wetting or emulsifying agents, pH buffering agents, stabilizers, solubility enhancers, or agents such as sodium acetate, sorbitan monolaurate, triethanolamine oleate, or cyclodextrin.

The term "therapeutically effective amount" or "effective dosage" as used herein refers to the dosage or concentration of a drug effective to treat a disease or condition. For example, with regard to the use of the antibodies or antigen-binding fragments disclosed herein to treat cancer, a therapeutically effective amount is the dosage or concentration of the antibody or antigen-binding fragment capable of eradicating all or part of a tumor, inhibiting or slowing tumor growth, inhibiting growth or proliferation of cells mediating a cancerous condition, inhibiting tumor cell metastasis, ameliorating any symptom or marker associated with a tumor or cancerous condition, preventing or delaying the development of a tumor or cancerous condition, or some combination thereof.

The effective dosage of an antibody or antigen-binding fragment provided herein may be determined using methods well known in the art. For example, the effective dosage may be established by determining whether a tumor being treated in a subject shrinks, ceases to grow, or grows more slowly following administration at a particular dosage. The size and progress of a tumor can be determined using methods well known in the art, such as for example X-ray, magnetic resonance imaging (MRI), CT scan, or visual detection (e.g., a surgical procedure). For example, where the cancer being treated is glioblastoma multiforme, a clinician may monitor treatment progress by imaging the tumor using a CT or MRI scan. Patient interviews regarding the appearance of symptoms of tumor growth (e.g., headaches, behavioral or mood changes) are also informative. Depending on the findings of the clinician, the dosage regimen can be altered accordingly. In another example, where the cancer being treated is melanoma, a clinician can monitor treatment progress by visual inspection of the melanoma lesion. The clinician may evaluate a variety of visual parameters, such as for example size, thickness, changes in growth pattern, or changes in appearance. Depending on the findings of the clinician, the dosage regimen can be altered accordingly.

In general, tumor size and proliferation can be measured using a thymidine PET scan (see, e.g., Wells 1996). The thymidine PET scan generally requires the injection of a radioactive tracer, such as $[2-^{11}C]$-thymidine, followed by a PET scan of the subject's body (Vander Borght 1991a; Vander Borght 1991b). Other tracers that can be used include $[^{18}F]$-FDG (18-fluorodeoxyglucose), $[^{124}I]$IUdR (5-[124I]iodo-2'- deoxyuridine), [$^{76}$Br]BrdUrd (Bromodeoxyuridine), [$^{18}$F] FLT (3'-deoxy-3' fluorothymidine) or [$^{11}$C]FMAU (2'-fluoro-5-methyl-1-β-D-arabinofuranosyluracil).

The effective dosage of an antibody or antigen-binding fragment as provided herein will depend on various factors known in the art, such as for example body weight, age, past medical history, present medications, state of health of the subject and potential for cross-reaction, allergies, sensitivities and adverse side-effects, as well as the administration route and extent of tumor development. Dosages may be proportionally reduced or increased by one of ordinary skill in the art (e.g., physician or veterinarian) as indicated by these and other circumstances or requirements.

In certain embodiments, an antibody or antigen-binding fragment as provided herein may be administered at a therapeutically effective dosage of about 0.01 mg/kg to about 100 mg/kg (e.g., about 0.01 mg/kg, about 0.5 mg/kg, about 1 mg/kg, about 2 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg). In certain of these embodiments, the antibody or antigen-binding fragment is administered at a dosage of about 50 mg/kg or less, and in certain of these embodiments the dosage is 10 mg/kg or less, 5 mg/kg or less, 1 mg/kg or less, 0.5 mg/kg or less, or 0.1 mg/kg or less. A given dosage may be administered at various intervals, such as for example once a day, two or more times per day, two or more times per week, once per week, once every two weeks, once every three weeks, once a month, or once every two or more months. In certain embodiments, the administration dosage may change over the course of treatment. For example, in certain embodiments the initial administration dosage may be higher than subsequent administration dosages. In certain embodiments, the administration dosage may vary over the course of treatment depending on the reaction of the subject.

Dosage regimens may be adjusted to provide the optimum desired response (e.g., a therapeutic response). For example, a single dose may be administered, or several divided doses may be administered over time.

Pharmaceutical compositions comprising the antibodies or antigen-binding fragments disclosed herein, and in certain embodiments various chemotherapeutic agents, may be prepared by methods well known in the art of pharmacy. See, e.g., Gilman, et al., (eds.) (1990), *The Pharmacological Bases of Therapeutics*, 8th Ed., Pergamon Press; A. Gennaro (ed.), *Remington's Pharmaceutical Sciences*, 18th Edition, (1990), Mack Publishing Co., Easton, Pa.; Avis, et al., (eds.) (1993) *Pharmaceutical Dosage Forms: Parenteral Medications* Dekker, New York; Lieberman, et al., (eds.) (1990) *Pharmaceutical Dosage Forms: Tablets* Dekker, New York; and Lieberman, et al., (eds.) (1990), *Pharmaceutical Dosage Forms: Disperse Systems* Dekker, New York.

The antibodies and antigen-binding fragments disclosed herein may be administered by any route known in the art, such as for example parenteral (e.g., subcutaneous, intraperitoneal, intravenous, including intravenous infusion, intramuscular, or intradermal injection) or non-parenteral (e.g., oral, intranasal, intraocular, sublingual, rectal, or topical) routes. In embodiments wherein the antibodies or antigen-binding fragments are administered via injection, injectable pharmaceutical compositions may be prepared in any conventional form, such as for example liquid solution, suspension, emulsion, or solid forms suitable for generating liquid solution, suspension, or emulsion. Preparations for injection may include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use, and sterile emulsions. The solutions may be either aqueous or nonaqueous.

In certain embodiments, unit-dose parenteral preparations are packaged in an ampoule, a vial or a syringe with a needle. All preparations for parenteral administration should be sterile, as is known and practiced in the art.

In certain embodiments, a sterile, lyophilized powder is prepared by dissolving an antibody or antigen-binding fragment as disclosed herein in a suitable solvent. The solvent may contain an excipient which improves the stability or other pharmacological components of the powder or reconstituted solution, prepared from the powder. Excipients that may be used include, but are not limited to, water, dextrose, sorbital, fructose, corn syrup, xylitol, glycerin, glucose, sucrose or other suitable agent. The solvent may contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides a desirable formulation. In one embodiment, the resulting solution will be apportioned into vials for lyophilization. Each vial can contain a single dosage or multiple dosages of the anti-VEGF antibody or antigen-binding fragment thereof or composition thereof. Overfilling vials with a small amount above that needed for a dose or set of doses (e.g., about 10%) is acceptable so as to facilitate accurate sample withdrawal and accurate dosing. The lyophilized powder can be stored under appropriate conditions, such as at about 4° C. to room temperature.

Reconstitution of a lyophilized powder with water for injection provides a formulation for use in parenteral administration. In one embodiment, for reconstitution the lyophilized powder is added to sterile water or other liquid suitable carrier. The precise amount depends upon the selected therapy being given, and can be empirically determined.

In certain embodiments, expression systems are provided for expressing the antibodies or antigen-binding fragments disclosed herein. These expression systems include polynucleotides encoding the antibodies or antigen-binding fragments, vectors comprising these polynucleotides, and host cells comprising these vectors. Polynucleotides encoding the antibodies or antigen-binding fragments disclosed herein may be isolated or synthesized using methods known in the art, and inserted into a replicable vector for amplification or cloning. Polynucleotides encoding variable light ($V_L$) and variable heavy ($V_H$) chains of the antibodies may be expressed from a single vector, or they may be expressed using two separate vectors, followed by in vitro assembly. In certain embodiments, they may be co-expressed from two separate vectors within the same cell and assembled intracellularly (see, e.g., U.S. Pat. No. 4,816,567 or 5,595,898). Suitable vectors may contain various configurations of one or more regulatory sequences, such as promoters, enhancers, or transcription initiation sequences, as well as genes encoding markers for phenotypic selection. Vectors having suitable backbones for expression of the antibodies or antigen-binding fragments disclosed herein are known in the art (see, e.g., U.S. Pat. No. 7,192,737). In certain embodiments, the vector may contain a polynucleotide sequence encoding the constant regions of the heavy chain ($C_H$) and light chain ($C_L$) of a human IgG2 immunoglobulin. Alternatively, the vector may express only the $V_H$ and $V_L$ chains of the antibody, with the expressed polypeptide comprising an Fv fragment rather than a whole antibody. Vectors may be inserted into a suitable host cell for amplification or expression of the polynucleotide sequence. The host cells may be cultured for antibody production in a variety of media known in the art, such as for example Minimal Essential Medium (MEM) (Sigma), RPMI-1640 (Sigma), Dulbecco's Modified Eagle's Medium (DMEM) (Sigma), and Ham's F10 (Sigma). Media may be supplemented with a variety of agents, such as for example hormones, growth factors, salts, buffers, nucleotides, antibiotics, trace elements, glucose, or other energy sources. Culture conditions such as temperature and pH may be adjusted using parameters well known in the art. Following expression, one or more antibodies or antigen-binding fragments as provided herein may be purified using methods known in the art.

The antibodies or antigen-binding fragments disclosed herein may comprise conjugates for specific delivery to cancer cells. In addition, binding of the antibodies or antigen-binding fragments to tumor cells may be used to recruit host immune responses. This host immune response may be increased by utilizing bivalent antibodies, with one binding site corresponding to the fully human antibodies or antigen-binding fragments provided herein and another binding site that recognizes another antigen.

In certain embodiments, the antibodies or antigen-binding fragments disclosed herein may comprise oligosaccharides with high fucose content. In other embodiments, the antibodies or antigen-binding fragments disclosed herein may have reduced fucose content, such as for example fucose-free Fc antibodies. Reduced fucose antibodies may be generated using a cell line with reduced fucosylation activity, such as for example rat YB2/0 cells (Shinkawa 2003) or the CHO variant cell line Lec13 (Shields 2002).

The following examples are provided to better illustrate the claimed invention and are not to be interpreted as limiting the scope of the invention. All specific compositions, materials, and methods described below, in whole or in part, fall within the scope of the present invention. These specific compositions, materials, and methods are not intended to limit the invention, but merely to illustrate specific embodiments falling within the scope of the invention. One skilled in the art may develop equivalent compositions, materials, and methods without the exercise of inventive capacity and without departing from the scope of the invention. It will be understood that many variations can be made in the procedures herein described while still remaining within the bounds of the present invention. It is the intention of the inventors that such variations are included within the scope of the invention.

EXAMPLES

Example 1

Generation of Antibodies that Bind $hVEGF_{165}$

Human single-chain Fv (scFv) phage display libraries were panned against immobilized $hVEGF_{165}$ to identify a panel of antibody fragments with the ability to bind $hVEGF_{165}$. Panning was carried out using standard protocols (see, e.g., Methods in Molecular Biology, vol. 178: Antibody Phage Display: Methods and Protocols Edited by: P. M. O'Brien and R. Aitken, Humana Press; "Panning of Antibody Phage-Display Libraries," Coomber, D. W. J., pp. 133-145, and "Selection of Antibodies Against Biotinylated Antigens," Chames, P., et al., pp. 147-157).

Briefly, three wells of a NUNC® MAXISORP plate were coated with 50 µl of recombinant $hVEGF_{165}$ (R&D Systems, catalog no. 293-VE) at a concentration of 10 µg/ml in PBS. After overnight incubation at 4° C., free binding sites were blocked with 5% milk in PBS for one hour at room temperature. Approximately 200 µl of phage library in 5% milk/PBS was then added to the blocked wells and incubated at room temperature for approximately one to two hours. Wells were washed and bound phage was eluted using standard methods (see, e.g., Sambrook and Russell, Molecule Cloning: A Laboratory Manual, 3rd Edition, Cold Spring Harbor Laboratory Press, 2001). Eluted phage was amplified via infection for one hour at 37° C. into *E. coli* TG1 host cells in logarithmic growth phase. Infected TG1 cells were recovered by centrifugation at 2,500 RPM for five minutes, plated onto 15 cm 2YT-ampicillin-2% glucose agar plates, and incubated at 30° C. overnight. The panning process was then repeated using the amplified phage.

The cycle of panning, elution, and amplification was repeated for three rounds with decreasing concentration (e.g., 50 ug/ml $hVEGF_{165}$ at Round One, 10 ug/ml at Round Two, and then 10 ug/ml at Round Three), at which point single colonies from the plated TG1 cells were used to inoculate media in 96-well plates. Microcultures were grown to an $OD_{600}$ of 0.6, at which point expression of soluble scFv was induced by addition of 1 mM IPTG and overnight incubation in a shaker at 30° C. Bacteria were spun down, and periplasmic extract was used to test scFv binding to immobilized $hVEGF_{165}$ using a standard ELISA assay.

Example 2

Blocking of $hVEGF_{165}$ Binding to VEGF Receptors by scFvs

Phage clones from Example 1 exhibiting $hVEGF_{165}$ binding by ELISA were tested for their ability to block $hVEGF_{165}$ binding to VEGF-R1 and/or VEGF-R2 using the microplate-based competitive screening DELFIA® assay (Perkins Elmer, Waltham, Mass.).

Briefly, biotinylated $hVEGF_{165}$ solution was added 1:1 in volume to periplasmic extracts from Example 1 to a final concentration of 0.5 µg/ml. 100 µl of this mixture was added to a plate coated with VEGF-R1 or VEGF-R2 (R&D Systems: VEGF-R1/Flt-1, catalog no. 321-FL; VEGF-R2/KDR/Flk-1, catalog no. 357-KD) and incubated for 1.5 hours at room temperature. Plates were washed with PBST, and a 1:250 dilution of Europrium-Streptavidin in DELFIA Assay Buffer was added at 50 µl/well. Plates were incubated at room temperature for one hour, then washed with DELFIA Wash Buffer. DELFIA Enhancement Buffer was added at 50 µl/well, and plates were incubated for five minutes at room temperature. Plates were read on a Time-Resolved Fluorescence Gemini plate reader.

Example 3

Conversion of scFv to scFv-Fc and IgG

Two scFvs from Example 2 that inhibited $hVEGF_{165}$ binding to VEGF-R1 or VEGF-R2 by more than 60%, XPA.10.064 and XPA.10.072, were selected for conversion to scFv-Fc and/or IgG. The heavy chain variable regions (including heavy chain CDRs) and light chain variable regions (including light chain CDRs) of XPA.10.064 and XPA.10.072 are set forth in FIG. 1. The heavy chain CDRs (e.g., HCDR1, HCDR2 and HCDR3) and the light chain CDRs (e.g., LCDR1, LCDR2, and LCDR3) were determined by the Kabat numbering system (Kabat, E. A., et al. 1987, in Sequences of Proteins of Immunological Interest, US Department of Health and Human Services, NIH, USA). HCDR1, HCDR2 and HCDR3 amino acid sequences for XPA.10.064 and XPA.10.072 are set forth in SEQ ID NOs: 6, 7, and 8, respectively. LCDR1, LCDR2, and LCDR3 amino acid sequences for XPA.10.064 are set forth in SEQ ID NOs: 12, 13, and 14, respectively. LCDR1, LCDR2, and LCDR3 amino acid sequences for XPA.10.072 are set forth in SEQ ID NOs: 9, 10, and 11, respectively.

For conversion of XPA.10.064 and XPA.10.072 into scFv-Fc fusion proteins, scFv cDNAs were cloned into eukaryotic expression vectors that had been modified to encode the CH2 and CH3 domains of the gamma-2 (γ2) heavy chain constant region gene (U.S. Pat. No. 7,192,737; WO 2004/033693).

For conversion of XPA.10.064 and XPA.10.072 into IgG, the variable regions of both heavy and light chains were cloned into eukaryotic expression vectors encoding the kappa (κ), lambda (λ), or gamma-2 (γ2) heavy and light chain constant region genes (US 2006/0121604).

XPA.10.064 and XPA.10.072 scFv-Fc and IgG antibodies were transiently expressed in 293E cells as described previously (US 2006/0121604). Supernatant from transfected cells was harvested at day six of culture, and IgG was purified by Protein-A chromatography.

Example 4

Biacore Analysis of XPA.10.064 and XPA.10.072 scFv-Fc and IgG Binding Kinetics

Binding affinity of XPA.10.064 and XPA.10.072 scFv-Fcs was assessed using a BIACORE 2000 and a CM5 sensor chip (Biacore) with Protein A/G (Piece) immobilized on all flow cells at high density. Dilution and running buffer for these experiments was HBS-EP (Biacore) with 1:50 dilution of Chemiblocker® (Chemicon). Antibody capture was performed by injecting diluted XPA.10.064 and XPA.10.072 scFv-Fcs over flow cell 2 (fc2) at 20 µl/minute for a variable volume to achieve roughly 50-70 RU of antibody capture. Antibody concentrations were approximately 0.5 µg/ml. hVEGF$_{165}$ expressed from sf21 cells was injected over five minutes at 30 µl/minute using the Kinject feature with 15 minute dissociation over fc1 and 2. Four dilutions of hVEGF$_{165}$ were prepared in a three-fold serial dilution, giving concentrations of 5 µg/ml (119 nM), 1.667 µg/ml (39.7 nM), 0.55 µg/ml (13.2 nM), and 0.185 µg/ml (4.4 nM). Regenerations were performed with two injections of 100 mM HCl at 50 µl/minutes for twelve seconds each. Data was processed in Scrubber2 and fit by a 1:1 Langmuir interaction model after double referencing of the control flow cell and blank injections. XPA.10.064 and XPA.10.072 scFv-Fcs exhibited high and nearly identical binding affinity for hVEGF$_{165}$.

Figure 3:
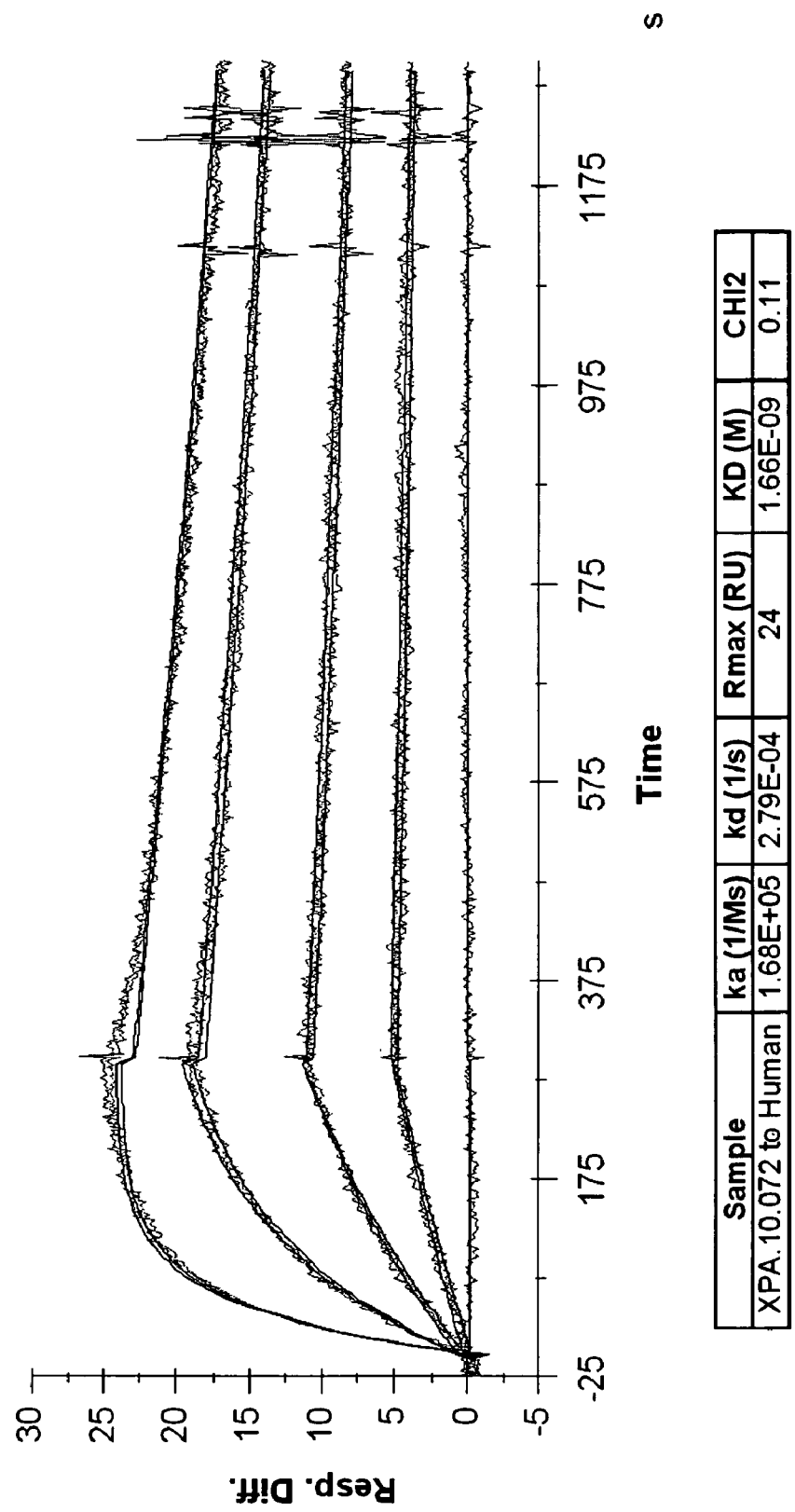
FIG. 3: Biacore analysis of XPA.10.072 IgG2 binding to $hVEGF_{165}$.
Figure 4:
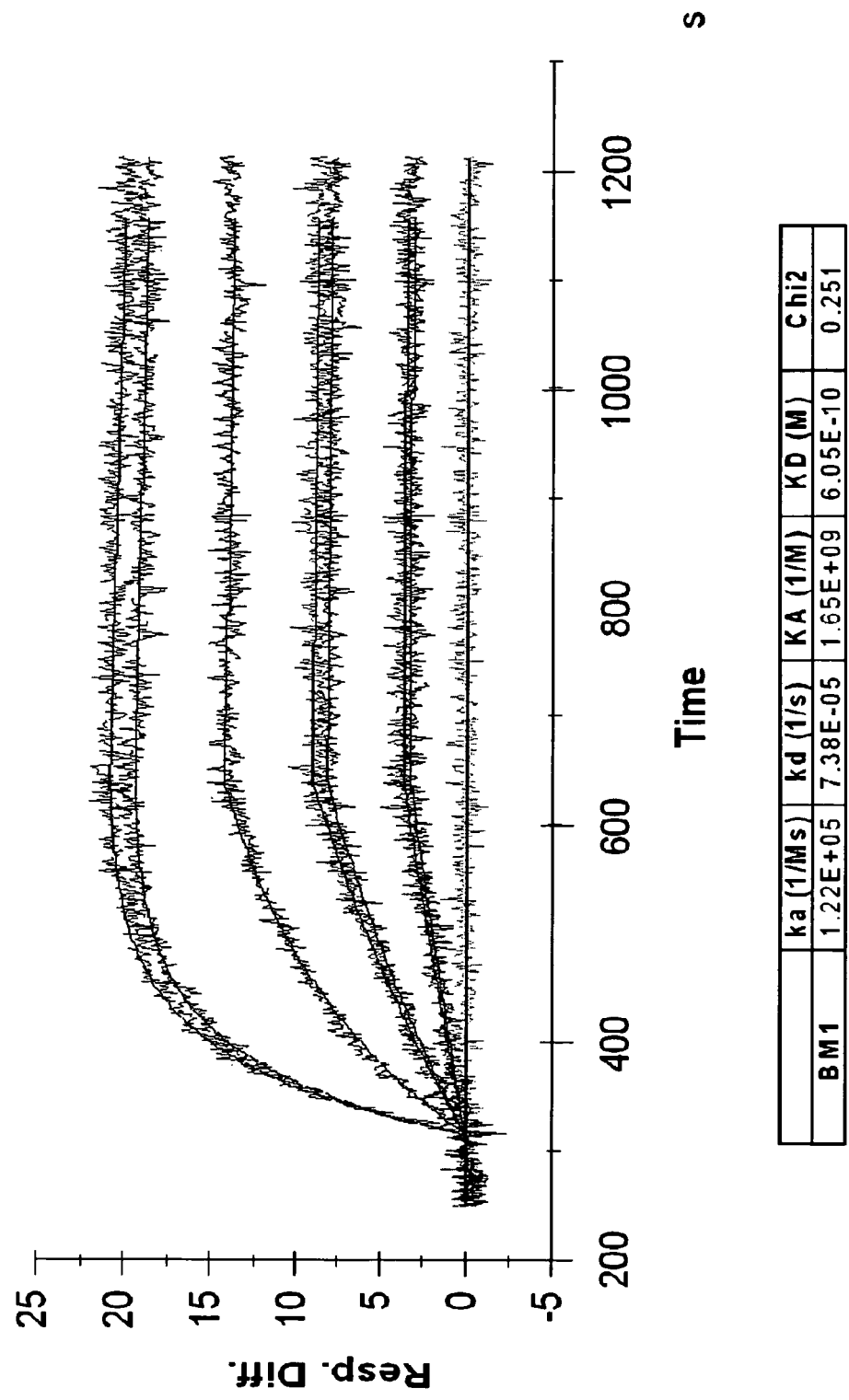
FIG. 4: Biacore analysis of Bevacizumab binding to $hVEGF_{165}$.

A similar protocol was utilized to assess binding kinetics of XPA.10.064 and XPA.10.072 IgG2. Both XPA.10.064 and XPA.10.072 IgG2s bound specifically to hVEGF$_{165}$ with similar low single digit nanomolar affinity (FIGS. 2-4), and exhibited only weak binding (>100 nM) to mVEGF$_{165}$. Both antibodies exhibited binding kinetics similar to those of Bevacizumab (Table 2).

TABLE 2

Binding affinity of XPA.10.064 and XPA.10.072 IgG2s to hVEGF$_{165}$

| | $k_a$ (1/Ms) | $k_d$ (1/s) | $R_{max}$ (RU) | $K_D$ (M) | Chi$^2$ |
|---|---|---|---|---|---|
| Bevacizumab | $1.22 \times 10^5$ | $7.38 \times 10^{-5}$ | 20 | $6.05 \times 10^{-10}$ (605 pM) | 0.251 |
| XPA.10.064 | $2.30 \times 10^5$ | $2.86 \times 10^{-4}$ | 30 | $1.24 \times 10^{-9}$ (1.24 nM) | 0.379 |
| XPA.10.072 | $1.68 \times 10^5$ | $2.79 \times 10^{-4}$ | 24 | $1.66 \times 10^{-9}$ (1.66 nM) | 0.110 |

Example 5

Blocking of hVEGF$_{165}$ Binding to VEGF Receptors by XPA.10.064 and XPA.10.072 IgGs The ability of XPA.10.064 and XPA.10.072 IgG2s to block binding of hVEGF$_{165}$ to VEGF-R1 and/or VEGF-R2 was assessed using a Biacore 2000 with a CM5 chip.

VEGF receptor (R&D Systems) was immobilized on the CM5 chip at a density of approximately 15,000 via amine coupling (Biacore). VEGF-R2 was immobilized on fc2 and VEGF-R1 was immobilized on fc4. Flow cells 1 and 3 served as references, and were activated and blocked in the same manner as the receptor immobilized flow cells. 0.15 µg/ml hVEGF$_{165}$ in HBS-EP running buffer was mixed 1:1 with antibody sample or buffer. Final antibody concentrations were 15, 5, 1.667, 0.556, 0.185, 0.0617, 0.0206, and 0 µg/ml. Samples were incubated for at least one hour prior to initiation of the Biacore analysis run. All samples were injected in duplicate and each set of antibody replicates had its own positive and negative control (no antibody with VEGF and no VEGF, respectively). Samples were injected at 10 µl/minute for 1.5 minutes over all flow cells. Regeneration was performed with a twelve second injection of Glycene, pH 1.75, at 50 µl/minute.

For data analysis, the slope of a linear portion of association (30 seconds to one minute) of the association phase was determined with a linear fit. The signal from each point was subtracted by the nearest blank, then divided by the matched 100% signal (no antibody) control to give the percent inhibition of that cycle. Data was plotted in GraphPad Prism and fit with a sigmoidal dose response curve to calculate the EC$_{50}$.

Figure 5:
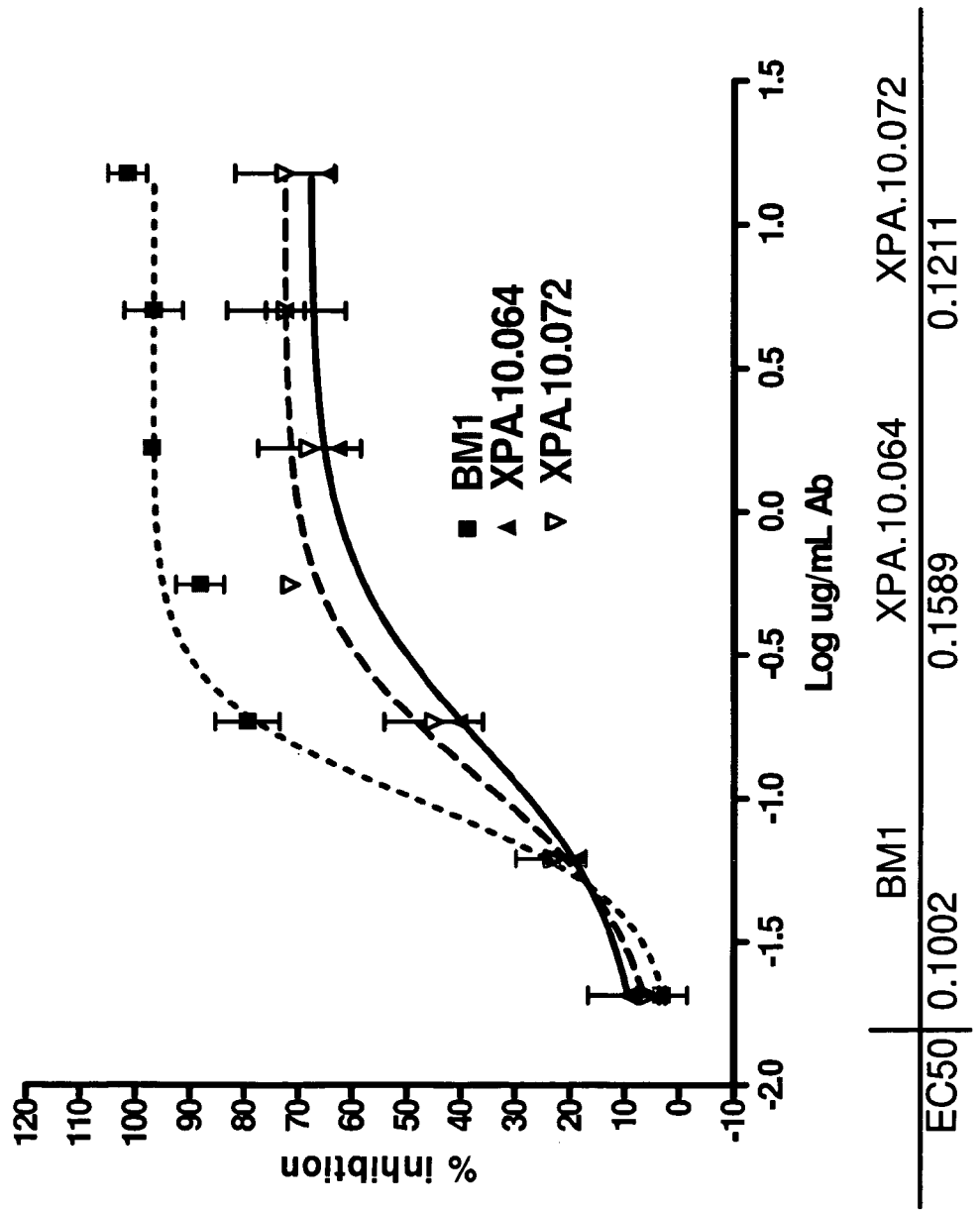
FIG. 5: Inhibition of $hVEGF_{165}$ binding to VEGF-R1 by Bevacizumab (BM1), XPA.10.064, and XPA.10.072.
Figure 6:
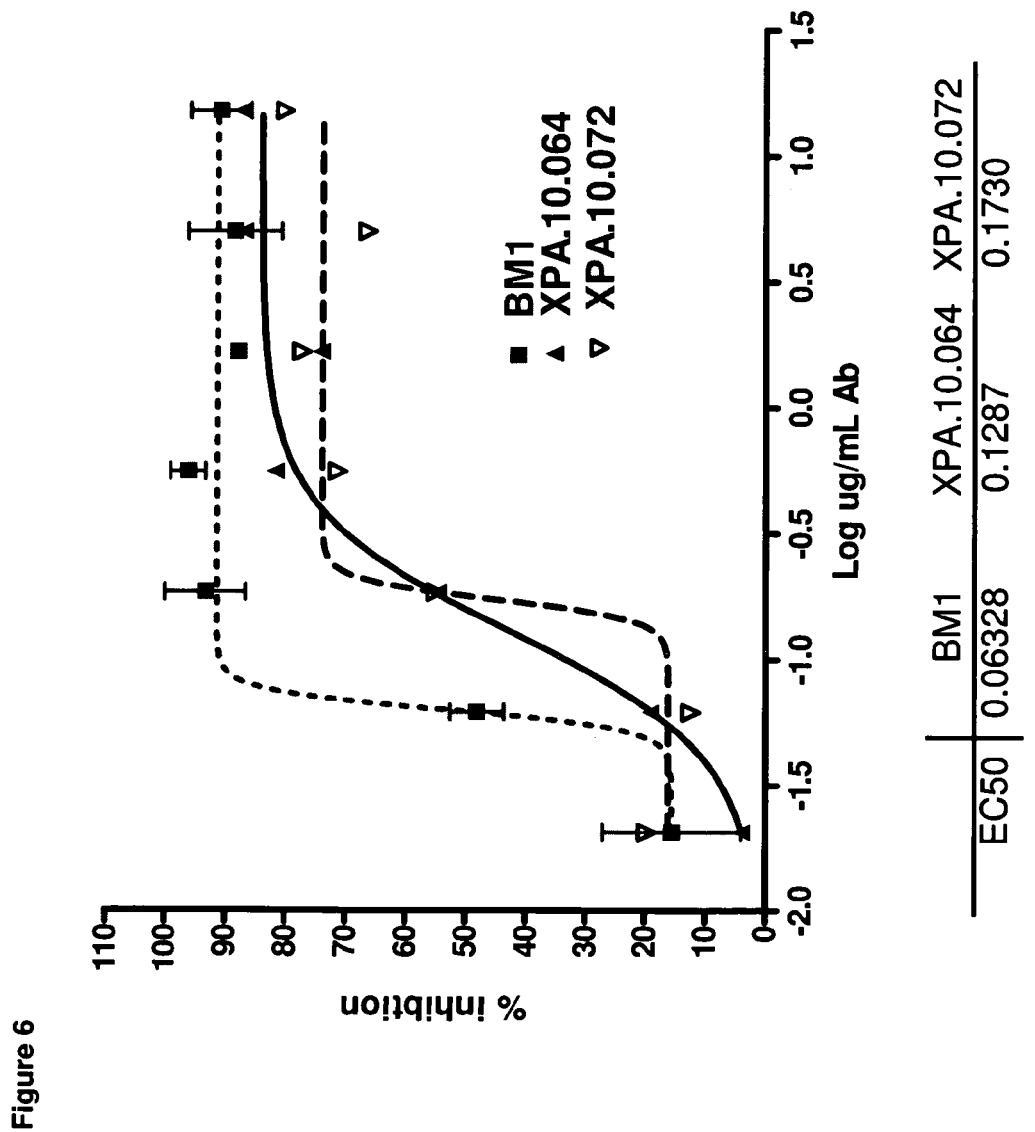
FIG. 6: Inhibition of $hVEGF_{165}$ binding to VEGF-R2 by Bevacizumab (BM1), XPA.10.064, and XPA.10.072.

XPA.10.064 and XPA.10.072 IgG2s both blocked hVEGF$_{165}$ binding to VEGF-R1 and VEGF-R2 at levels similar to Bevacizumab (FIGS. 5-6, Table 3).

TABLE 3

Inhibition of hVEGF$_{165}$ binding to VEGF-R1/R2 by XPA.10.064 and XPA.10.072:

| | Bevacizumab | XPA.10.064 | XPA.10.072 |
|---|---|---|---|
| hVEGF$_{165}$/VEGF-R1 (EC$_{50}$) | 0.1002 µg/ml | 0.1589 µg/ml | 0.1211 µg/ml |
| hVEGF$_{165}$/VEGF-R2 (EC$_{50}$) | 0.06328 µg/ml | 0.1287 µg/ml | 0.1730 µg/ml |

Example 6

Analysis of hVEGF$_{165}$ Epitopes Bound by XPA.10.064 and XPA.10.072

To determine whether the hVEGF$_{165}$ epitopes recognized by XPA.10.064 and XPA.10.072 were linear or conformational, three 200 ng samples of non-reduced or reduced and heat-denatured recombinant hVEGF$_{165}$ were subjected to electrophoresis on three separate SDS-PAGE gels. Electrophoresed proteins were transferred to Immulon-P membranes, and the blots were hybridized with XPA.10.064 IgG, XPA.10.072 IgG or Bevacizumab antibodies and incubated with 1 μg/ml secondary goat anti-human IgG HRP-conjugated antibody. Binding was detected with enhanced chemiluminescence (ECL) substrate (Pierce).

nylated goat polyclonal anti-VEGF antibody for one hour at room temperature. Detection was performed with HRP-conjugated streptavidin, followed by TMB chromogenic substrate (Calbiochem) using manufacturer protocol.

The binding pattern of XPA.10.064 and XPA.10.072 to hVEGF$_{121}$ mutants was similar to that of Bevacizumab (Tables 4-5), indicating that the antibodies bind overlapping or similar epitopes.

TABLE 4

XPA.10.064 and XPA.10.072 binding to hVEGF mutants:

| Antibody | CHO | hVEGF$_{121}$ | hVEGF$_{121}$-M81A | hVEGF$_{121}$-G88S | hVEGF$_{121}$-Q89A | hVEGF$_{121}$-G92A | rHu-VEGF$_{165}$ | rMu-VEGF$_{165}$ |
|---|---|---|---|---|---|---|---|---|
| PAB | 1.0 | 28 | 18.8 | 8.4 | 10.8 | 23.9 | 26.9 | 1.0 |
|  | 0.09 | 2.5575 | 1.7145 | 0.769 | 0.9852 | 2.1765 | 2.4544 | 0.0939 |
| Bevacizumab | 0.9 | 39.4 | 13.1 | 0.9 | 5.3 | 35.6 | 36.7 | 0.9 |
|  | 0.09 | 3.5953 | 1.1941 | 0.0828 | 0.4801 | 3.249 | 3.3501 | 0.0843 |
| XPA.10.064 | 0.9 | 29.1 | 9.5 | 0.9 | 3.5 | 22.8 | 23 | 0.7 |
|  | 0.085 | 2.6504 | 0.8678 | 0.0778 | 0.3194 | 2.0792 | 2.0946 | 0.0667 |
| XPA.10.072 | 1.5 | 31.8 | 13.4 | 1.0 | 3.3 | 30.5 | 29.2 | 1.1 |
|  | 0.142 | 2.902 | 1.2228 | 0.0951 | 0.2964 | 2.7809 | 2.6597 | 0.0982 |

Top row for each antibody: fold binding over CHO background
Bottom row for each antibody: Raw data

TABLE 5

Summary of epitope binding results

| Antibody | hVEGF$_{121}$ | hVEGF$_{121}$-M81A | hVEGF$_{121}$-G88S | hVEGF$_{121}$-Q89A | hVEGF$_{121}$-G92A | rHu-VEGF$_{165}$ | rMu-VEGF$_{165}$ |
|---|---|---|---|---|---|---|---|
| PAB | Yes | Yes | Yes | Yes | Yes | Yes | No |
| Bevacizumab | Yes | Reduced | No | Weak | Yes | Yes | No |
| XPA.10.064 | Yes | Reduced | No | Weak | Yes | Yes | No |
| XPA.10.072 | Yes | Reduced | No | Weak | Yes | Yes | No |

Figure 7:
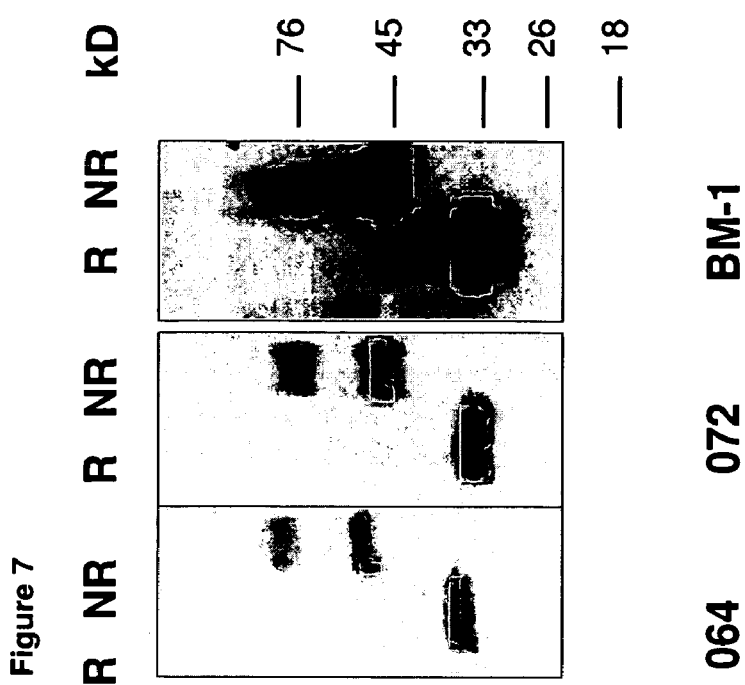
FIG. 7: Analysis of $hVEGF_{165}$ epitopes bound by Bevacizumab (BM1), XPA.10.064 (064), and XPA.10.072 (072).

XPA.10.064, XPA.10.072, and Bevacizumab all bind to linear epitopes on hVEGF$_{165}$ (FIG. 7).

Example 7

XPA.10.064 and XPA.10.072 hVEGF$_{121}$ Epitope Binding Studies

To determine whether XPA.10.064 and XPA.10.072 bind the same hVEGF$_{121}$ epitope as Bevacizumab, three ELISA comparative binding assays were performed using various hVEGF$_{121}$ mutants.

Previous mutation analysis has shown that VEGF residues M81, G88, Q89, and G92 are important for Bevacizumab binding to hVEGF$_{165}$ (Fuh 2006). To determine whether these residues are important for XPA.10.064 and XPA.10.072 binding, the following hVEGF$_{121}$ mutants were generated: hVEGF$_{121}$-M81A, hVEGF$_{121}$-Q89A, hVEGF$_{121}$-G92A, and hVEGF$_{121}$-G88S. Mutants were transiently expressed in CHO-K1 cells, and cell supernatants were collected for binding analysis by ELISA.

A microtiter plate was coated with XPA.10.064, XPA.10.072, Bevacizumab, or a control polyclonal goat anti-human VEGF (PAB) at a concentration of 1, 2, or 5 μg/ml and incubated overnight at 4° C. The plate was blocked with 30% ChemiBlock™ reagent (Millipore) in PBS for one hour at room temperature, and 30, 60, or 100 μl of CHO-K1 culture supernatant for each mutant, or 1 μg/ml of wild-type hVEGF$_{121}$, recombinant hVEGF$_{165}$, or recombinant mVEGF$_{165}$, was added to appropriate wells. After one hour of incubation, the plate was washed and incubated with a bioti- Example 8

Tissue Cross-Reactivity of XPA.10.064 and XPA.10.072

A frozen normal human tissue array (TMA) was used to evaluate immunohistochemical (IHC) reactivity of XPA.10.064 and XPA.10.072 using a single-color chromogenic technique. The TMA comprised 32 normal human tissue types, with each type consisting of tissues from two to three different donors. In addition to the TMA, larger sections of normal human liver, kidney, Fallopian tubes, pancreas, ureter, and adrenal gland were used to confirm staining results from the TMA or to replace missing tissues in the TMA. Positive controls included hVEGF proteins spotted on UV-resin slides and renal carcinoma tissue expressing high level hVEGF as assessed by strong staining with anti-hVEGF rabbit monoclonal antibody.

The TMA and normal human tissues and the hVEGF protein spot and renal carcinoma positive controls were stained with XPA.10.064, XPA.10.072 (human IgG2), or Bevacizumab at 20 μg/ml using a human-on-human IHC staining protocol. A human tonsillitis case was also included to monitor the effectiveness of the staining protocol. The final protocol did not have reactivity with tissue endogenous immunoglobulin in B-cell region of the tonsil tissue. Negative control antibodies were human IgG1 and IgG2 (Sigma, St. Louis, Mo.) and the human KLH antibody CHO.KLHG2.60 (IgG2).

XPA.10.064, XPA.10.072, and Bevacizumab were all reactive with hVEGF protein spots at 2-3+ on a scale of 0-4+, where 4+ indicates the highest staining intensity. For renal carcinoma tissue, Bevacizumab gave equivocal staining, while XPA.10.064 and XPA.10.072 stained cytoplasm of tumor cells.

Human IgG1 and IgG2 did not stain any tissue elements, giving only minimal background staining. CHO.KLHG2.60 had reactivity with cells in the adrenal cortex, epithelial cells in esophagus, mammary gland, pancreas, prostate, stomach, thyroid gland, ureter cervix, and Fallopian tube. Due to this reactivity, human IgG1 and IgG2 were used as reference negative controls.

XPA.10.064 had the broadest tissue reactivity spectrum of the test antibodies. XPA.10.064 stained strongly with smooth muscle cells in bladder, GI track, Fallopian tube, mammary gland, prostate, ureter, and uterus, and with epithelial cells in Fallopian tube, prostate, skin, small intestine, stomach, thyroid gland, ureter, endometrial glands of the uterus, and uterus cervix. In addition, XPA.10.064 stained some neurons and nerve fibers in cerebellum, cerebral cortex, and spinal cord, as well as cardiac and skeletal muscles, cells in pituitary glands, renal glomeruli, liver sinusoid endothelium, stromal cells of thymus, macrophages in lung, and cells in the adrenal cortex. XPA.10.072 stained strongly with nerve fibers in cerebellum, cerebral cortex, and spinal cord. XPA.10.072 also stained smooth muscles of the GI track, Fallopian tube, prostate, ureter, and uterus, epithelial cells in esophagus, Fallopian tube, mammary gland, prostate, stomach, small intestine, thyroid gland, and ureter, macrophages in lung, and fibroblast/histiocytes in placenta. Bevacizumab stained negative with all normal human tissues.

To determine whether the immunohistochemical reactivity of XPA.10.064 and XPA.10.072 represented on- or off-target binding, a multicolor immunofluorescence-based approach was utilized. This approach is based on the simultaneous comparison of immunoreactivity of a known "gold standard" anti-VEGF antibody to test antibodies. On-target reactivity of test antibodies manifests as co-localization with the "gold standard" antibody, while lack of co-localization indicates off-target reactivity.

Frozen sections of cell pellets from positive (Du145) and negative (Hek 293) control cells were stained with commercial mouse anti-human anti-VEGF antibody (BD Pharmingen, clone G153-694) using the same chromogenic IHC methodology employed in the initial experiments. This antibody stained Du145 cells, but failed to stain Hek 293 cells. In addition, frozen sections of colon carcinoma stained with this antibody demonstrated a characteristic pattern of reactivity in the epithelial and tumor associated matrix components with good internal negative controls. Therefore, G153-694 was designated the "gold standard" positive control antibody.

Using a protocol from the Zenon IgG Labeling Kit (Molecular Probes), primary antibody was pre-incubated with a fluorochrome conjugated Fc-targeted anti-human Fab, followed by neutralization of non-reacted Fab with molar excess of the appropriate normal serum. Fluorescent antibody-Fab complex used as the staining reagent, followed by nuclear counterstaining with DAPI. Frozen sections from an adenocarcinoma of the colon (Tissue ID 4558) were used as control VEGF-positive tissue for these co-localization studies. XPA.10.064 and XPA.10.072 antibodies were labeled with red (Alexa Fluor 594), and "gold standard" antibody was labeled with green (Alexa Fluor 488). The assay was repeated using the reverse color combination, which gave essentially the same results. Images were captured using a Leica TCS-SP, model DM RXE laser scanning confocal microscope and Leica Confocal software, version 2.0 (Leica Microsystems, Wetzler, Germany). Multiple fields were imaged at 400× (at least three), and representative fields were analyzed for colocalization using Image Pro software (Media Cybernetics, Silver Spring, Md.). Since Bevacizumab was essentially negative in all of the initial IHC studies on both colon carcinoma and frozen pellet sections, it was not included in the co-localization studies.

Figure 8:
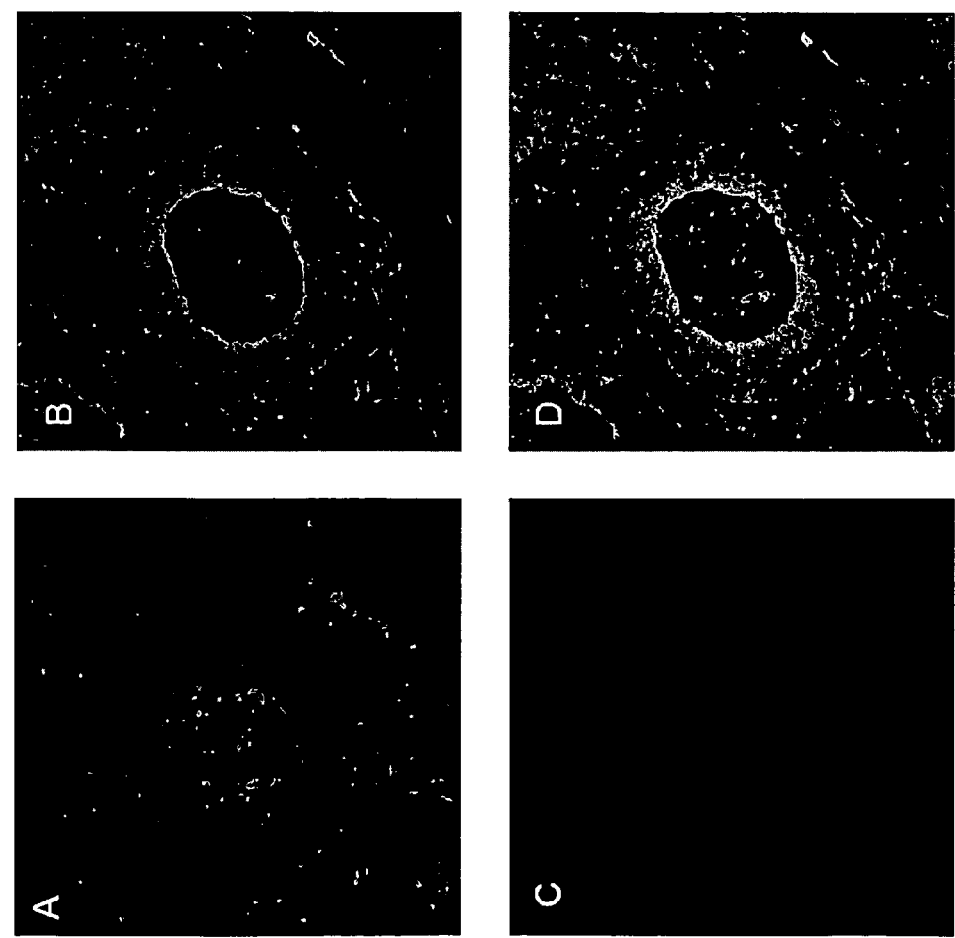
FIG. 8: Co-localization of XPA.10.064 and G153-694 Panel A is shows the staining with XPA.10.064. Panel B shows staining with G153-694. Panel C shows staining with a nuclear dye. Panel D shows the merged image, where greater intensity (white) reflects colocalization.
Figure 9:
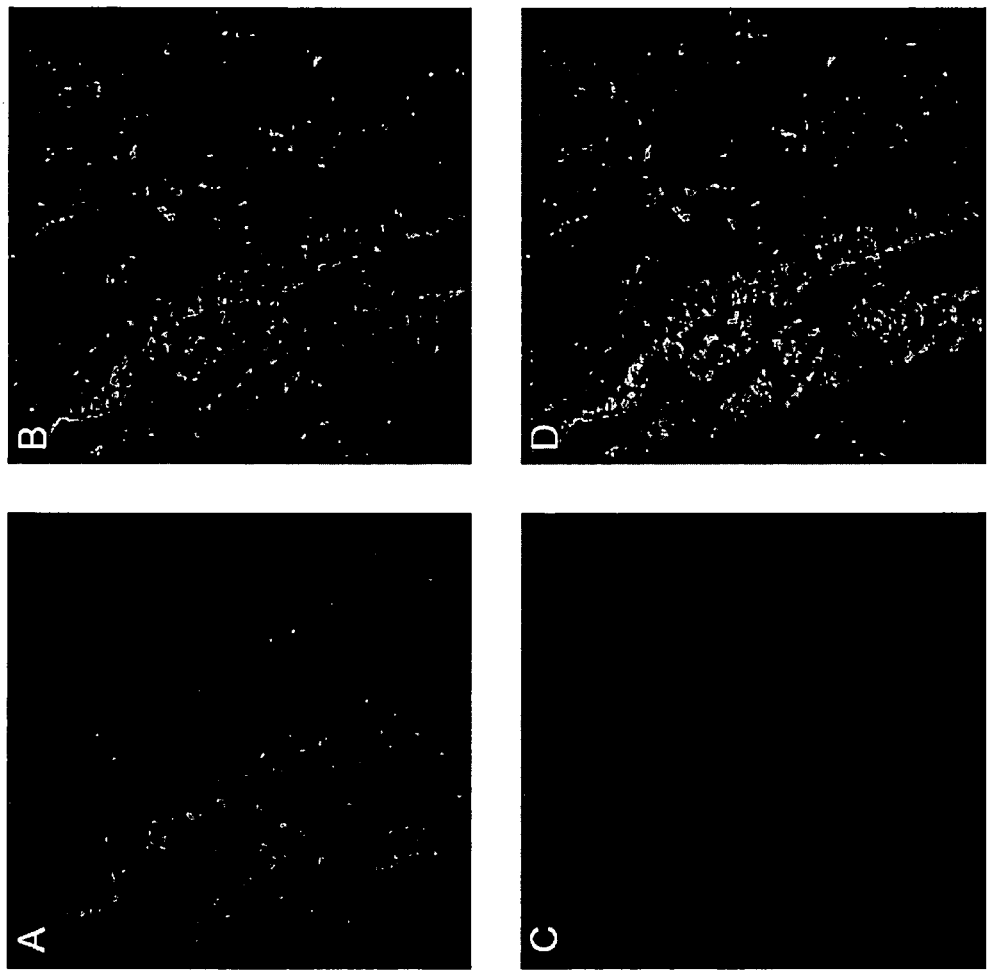
FIG. 9: Co-localization of XPA.10.072 and G153-694. Panel A is shows the staining with XPA.10.072. Panel B shows staining with G153-694. Panel C shows staining with a nuclear dye. Panel D shows the merged image, where greater intensity (white) reflects colocalization.

XPA.10.064 and XPA.10.072 demonstrated similar high degree of colocalization, with XPA.10.064 showing the greatest intensity of tissue staining (FIGS. 8-9).

Example 9

Inhibition of HUVEC Proliferation by XPA.10.064 and XPA.10.072

XPA.10.064 and XPA.10.072 scFv-Fcs and IgG2s were tested for their ability to block proliferation of HUVECs.

Pooled HUVECs (Clonetics #CC-2519) were grown in ECGM Complete Media (Clonetics #CC-3024) plus BulletKit-2 (supplemented with rhEGF, rhFGF, rhVGEF, ascorbic acid, hydrocortisone, IGF, heparin, gentamycin/amphotericin, and 2% FBS). Cells were seeded at 2-3×10$^5$ cells per T-75 flask, and reached confluence at 3-4 days. The sub-confluent monolayer was washed with PBS, trypsinized, and neutralized with complete media containing PBS.

To measure HUVEC proliferation in the presence of hVEGF$_{165}$, a 16-point dose titration of hVEGF$_{165}$ expressed from HEK 293 cells was set up by diluting in basal growth medium (0-200 ng/ml final, 2× dilutions, 2× concentration, 50 µl/well). HUVEC cells were re-suspended at 2×10$^5$ cells/ml in cold basal medium/0.1% BSA, and 50 µl of cells (1×10$^4$ c/w) were added to each well of the hVEGF$_{165}$ titration plate for a final volume of 100 µl/well. Outer wells were flooded with PBS, and plates were sealed with parafilm to prevent dehydration. Plates were incubated for 96 hours in 5% CO$_2$ at 37° C., then brought to room temperature over approximately 15-20 minutes. Cell TiterGlo (TTG, Promega) was thawed and brought to substrate temperature, and 100 µl of substrate/buffer mixture was added to each well. The plate was shaken on an orbital plate shaker for 1-2 minutes, and 150 µl from each well was transferred to white bottom, white walled plates and incubated in the dark for 5-10 minutes. The plate was read on a luminometer with a one second integration.

For the proliferation inhibition assay, titrations of XPA.10.064, XPA.10.072, and Bevacizumab were generated (0-50 µg/ml final, 3× dilutions, 4× concentrations, 25 µl/well final volume). Antibodies were pre-incubated 1:1 with hVEGF$_{165}$ for two hours. After pre-incubation, 50 µl/well of VEGF/antibody complex was added to 50 µl/well of re-suspended HUVEC cells, and the plates were incubated for 96 hours and treated with TiterGlo buffer as described above.

Figure 10A:
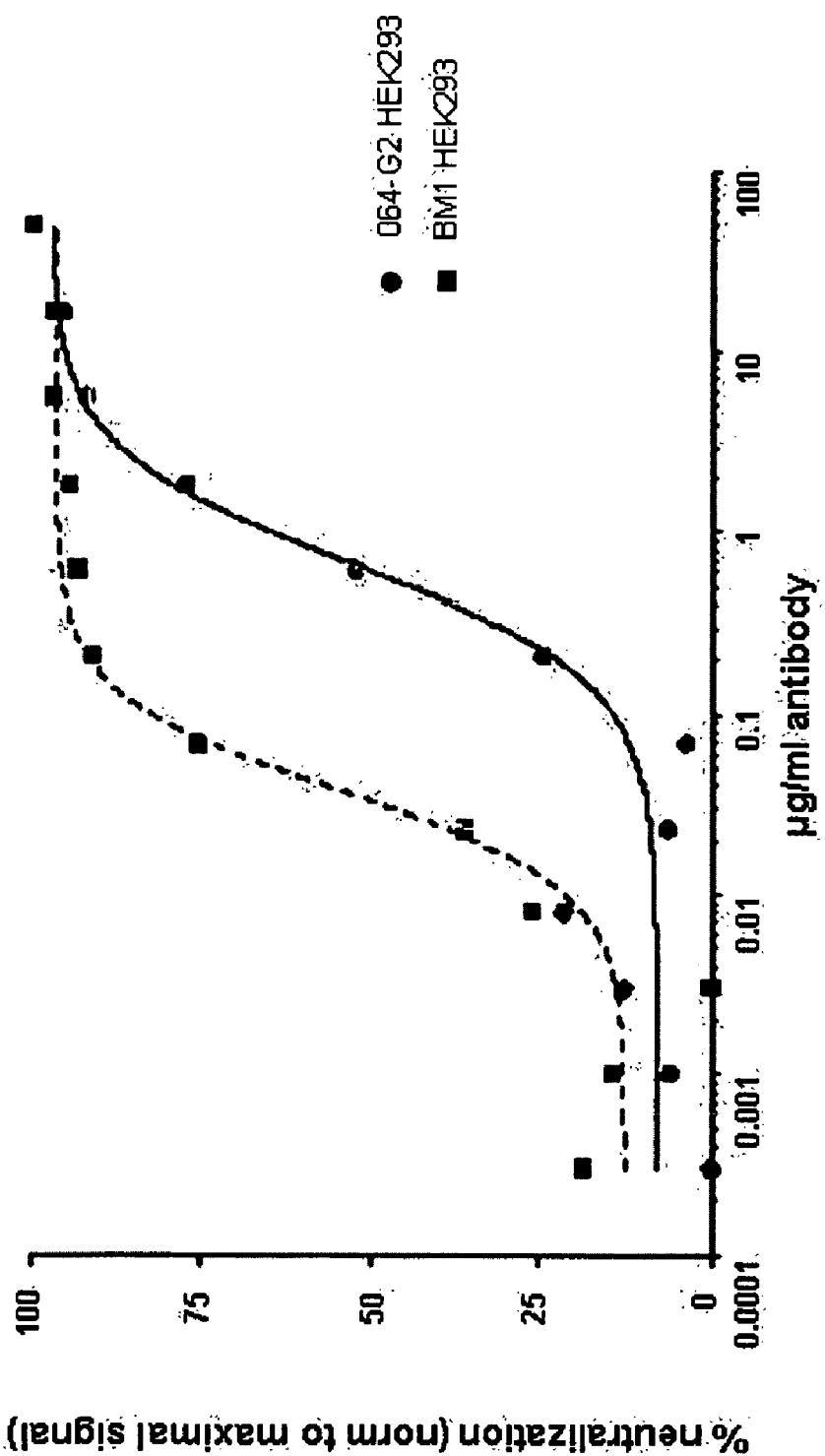
FIG. 10: Inhibition of HUVEC proliferation by (A) XPA.10.064 IgG2 and (B) XPA.10.072 IgG2.
Figure 10B:
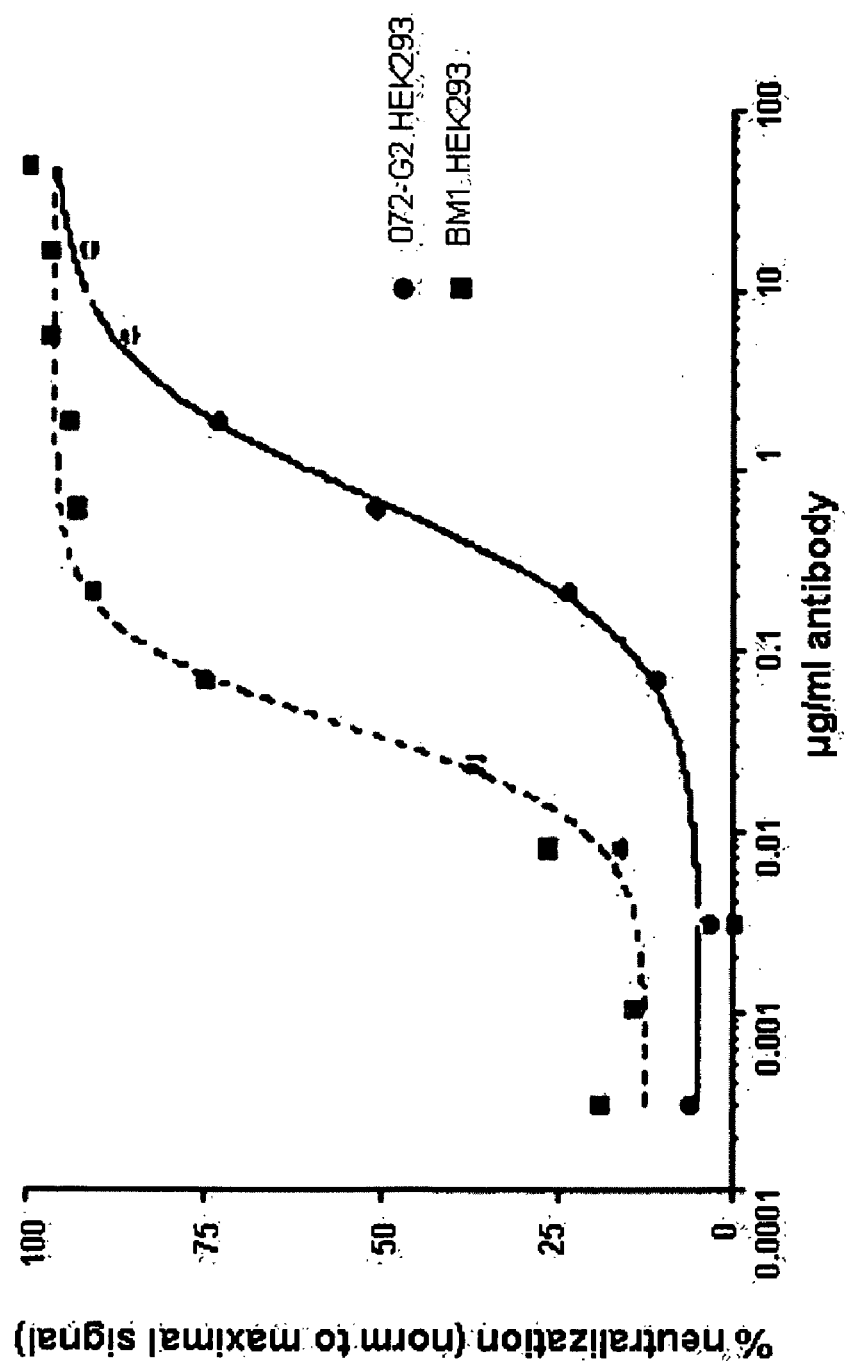

XPA.10.064 and XPA.10.072 scFvs and IgG2s inhibited HUVEC proliferation. IgG2 results are set forth in FIG. 10 and Table 6).

TABLE 6

Inhibition of HUVEC proliferation by XPA.10.064, XPA.10.072, and Bevacizumab.

| | EC$_{50}$ (µg/ml) | | |
|---|---|---|---|
| | XPA.10.064 | XPA.10.072 | BM-1 |
| HEK 293 hVEGF$_{165}$ | 0.66 | 0.68 | 0.04 |

Example 10

Inhibition of VEGF-R2 Phosphorylation by XPA.10.064 and XPA.10.072

The ability of XPA.10.064 and XPA.10.072 to inhibit VEGF-R2 phosphorylation by hVEGF$_{165}$ was analyzed by ELISA.

To generate lysate plates, HUVEC cells between passages two and six were thawed and plated into TC flasks in EGM2 complete media (Lonza), and allowed to grow for one to two passages. Sub-confluent cells were trypsinized, neutralized with complete media, washed twice with PBS, and counted. Cells were plated at 1×10$^5$ cells/well in complete media in 24w format (triplicate wells) and incubated at 37° C. for 24 hours. After incubation, cells were washed twice with room temperature PBS and starved in EBM2 medium (Lonza) plus 0.1% BSA for five hours. PBS was decanted and cells were incubated with a dose titration of hVEGF$_{165}$ (stimulation) or pre-complexed VPA.10.064+hVEGF$_{165}$, VPA.10.072+hVEGF$_{165}$, or Bevacizumab+hVEGF$_{165}$ (inhibition) for five minutes. VPA.10.064+hVEGF$_{165}$ and VPA.10.072+hVEGF$_{165}$ were generated by mixing a 2× dose titration of antibody 1:1 with 2× hVEGF$_{165}$ (final concentration: 20 ng/ml) and incubating at 37° C. for 24 hours. hVEGF$_{165}$, VPA.10.064+hVEGF$_{165}$, and VPA.10.072+hVEGF$_{165}$ were decanted and cells were washed twice with ice cold PBS. 65 µl/well of lysis buffer/well (1% NP-40, 20 mM Tris, pH 8.0, 137 mM NaCl, 10% glycerol, 2 mM EDTA, 1 mM activated sodium orthovanadate, 10 µg/ml Leupeptin) was added, and cells were rocked at 4° C. for 30 minutes until needed.

Capture antibody specific for VEGF-R2 (R&D Systems, VEGF-R2/KDR/Flk-1, catalog no. 357-KD) was diluted to a working concentration of 8.0 g/ml in PBS and coated onto a 96 well microplate at 100 µl/well. VEGF-R2/KDR/Flk-1 binds both phosphorylated and non-phosphorylated VEGF-R2. The plate was sealed and incubated overnight. Each well was aspirated and washed with wash buffer five times, and the plate was blocked by adding 300 µl/well of block buffer and incubating at room temperature for one to two hours. Each well was aspirated and washed with wash buffer five more times, and 100 µl of HUVEC lysate was added to each. The plate was incubated for two hours at room temperature, and wells were aspirated and washed five times with wash buffer. 100 µl of HRP-conjugated detection antibody specific for phosphorylated tyrosine was added to each well, and the plate was covered and incubated for two hours at room temperature out of direct light. Wells were aspirated and washed five times with wash buffer, and 100 µl of substrate solution was added to each well. The plate was incubated for 20 minutes at room temperature out of direct light, and 50 µl of stop solution was added to each well. The optical density of each well was read on a microplate reader at 450 nm.

Figure 11:
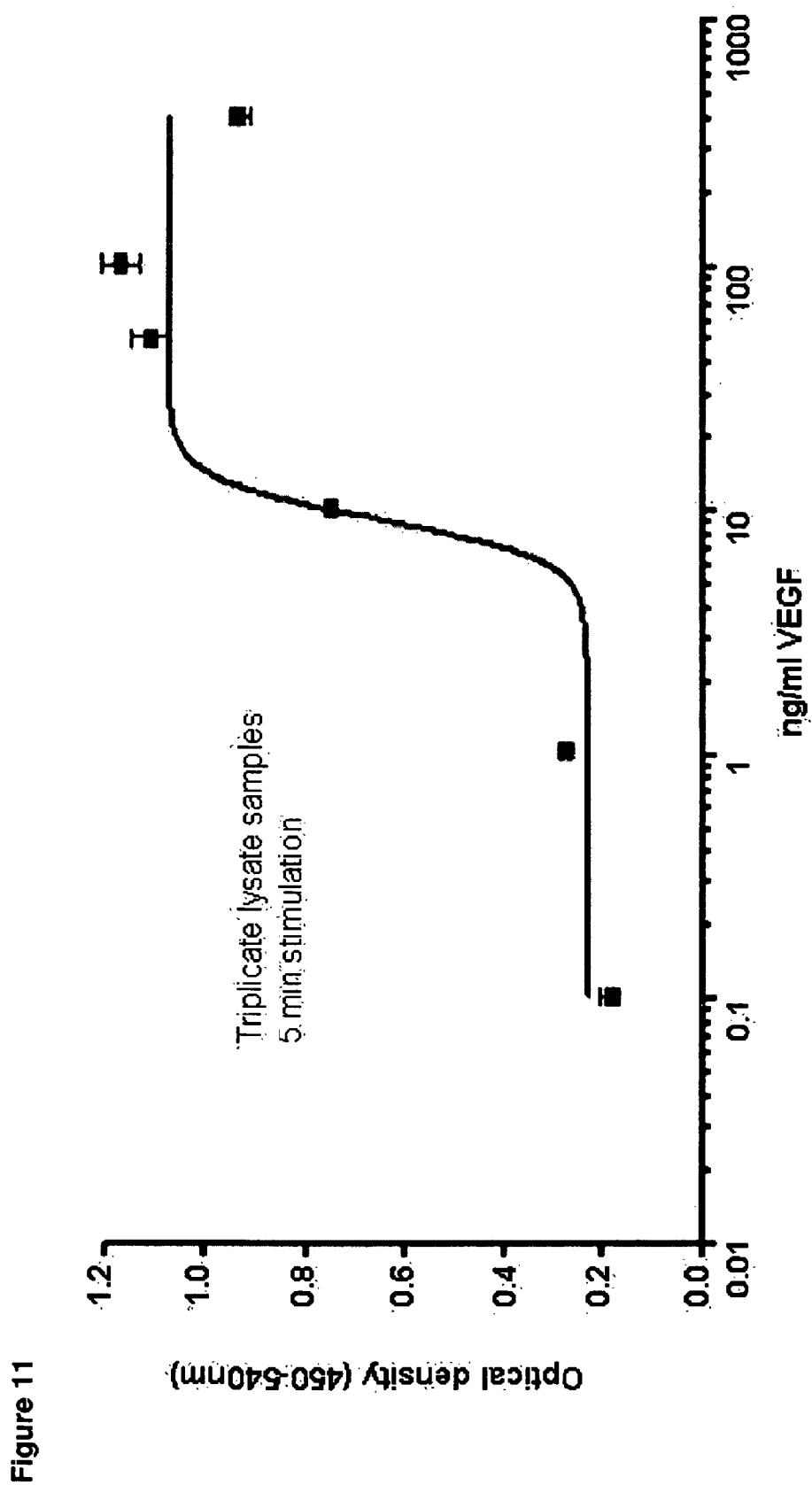
FIG. 11: Treatment of HUVECs with a dose titration of hVEGF$_{165}$ leads to an increase in phosphorylation of VEGF-R2.
Figure 12:
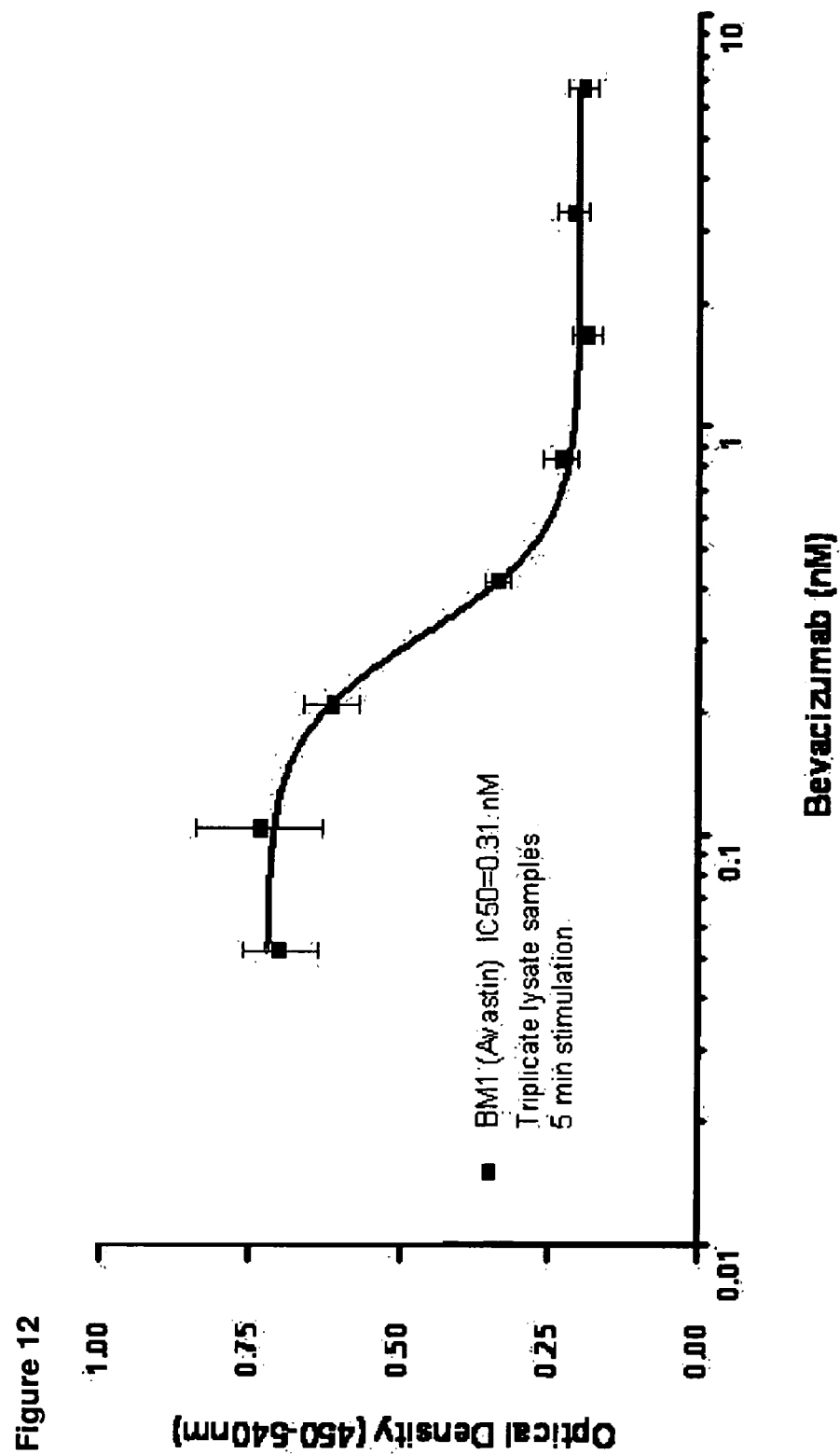
FIG. 12: Treatment of HUVECs with a dose titration of hVEGF$_{165}$ plus Bevacizumab resulted in a decrease in VEGF-R2 phosphorylation.
Figure 13:
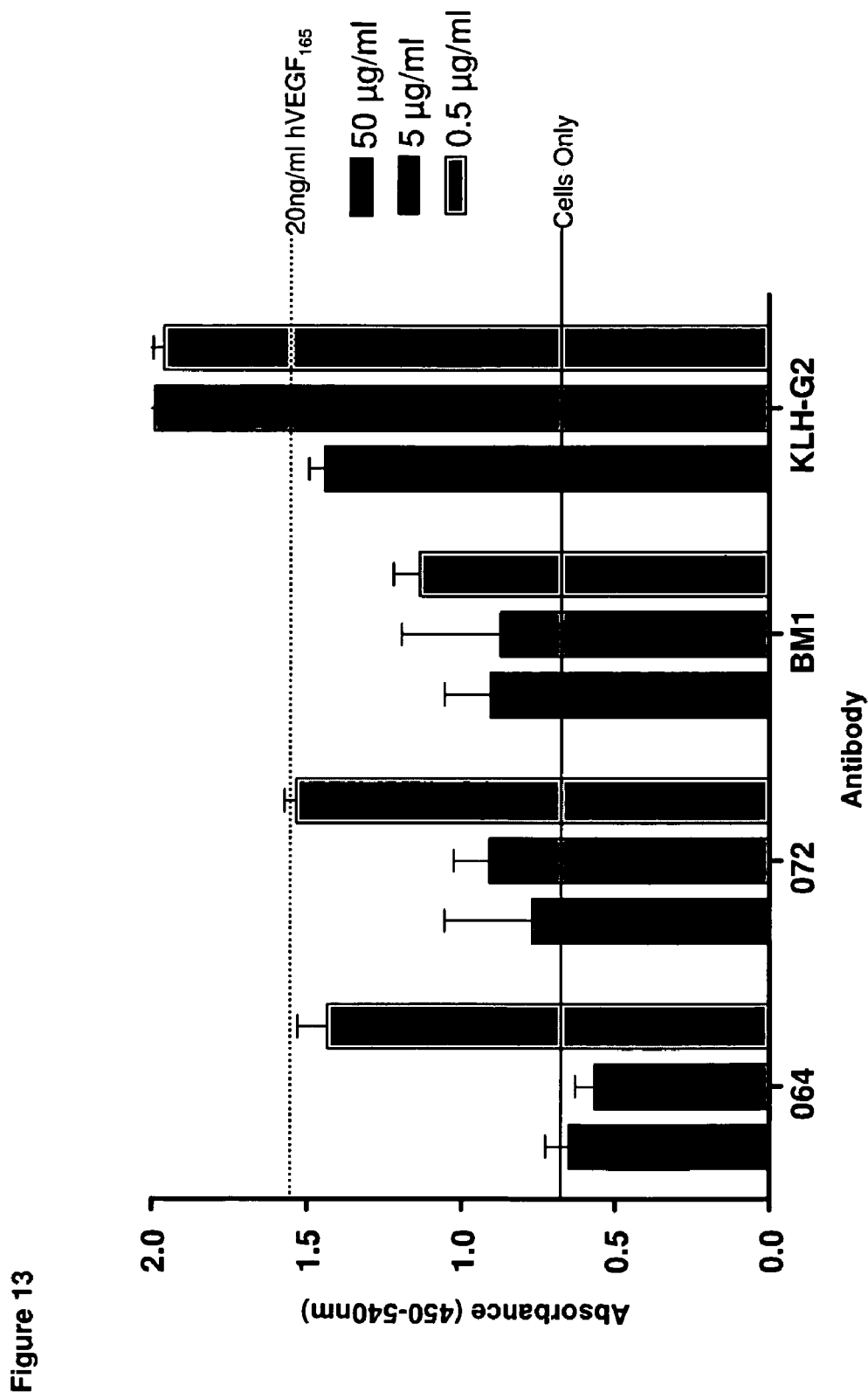
FIG. 13: XPA.10.064 (064) and XPA.10.072 (072) IgG2s inhibit hVEGF$_{165}$-induced phosphorylation of VEGF-R2.

HUVECs treated with a dose titration of hVEGF$_{165}$ exhibited an increase in phosphorylated VEGF-R2 (FIG. 11). HUVECs treated with a dose titration of Bevacizumab+hVEGF$_{165}$ exhibited a decrease in VEGF-R2 phosphorylation (FIG. 12). HUVECs treated with a dose titration of XPA.10.064+hVEGF$_{165}$ or XPA.10.072+hVEGF$_{165}$ exhibited a decrease in VEGF-R2 phosphorylation. Results for each antibody are summarized in FIG. 13.

Example 11

Inhibition of Angiogenesis by XPA.10.064 and XPA.10.072

A Matrigel® plug assay was used to measure the ability of XPA.10.064 and XPA.10.072 to inhibit angiogenesis in vivo.

Figure 14:
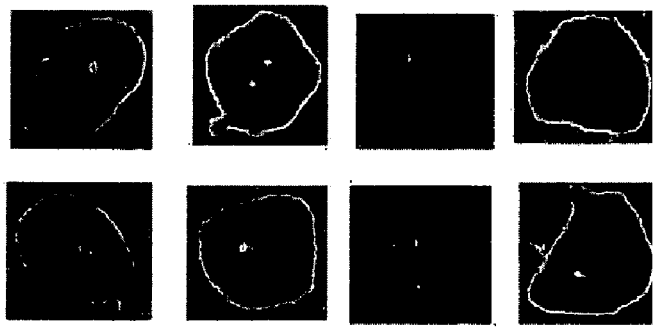
FIG. 14: Visual scoring system for Matrigel® plugs. Examples of each score 0 to 3 are shown.

Female NU/NU mice age 6-7 weeks were injected s.c. in the abdomen with 0.5 ml Matrigel® (BD Biosciences, San Jose, Calif.) containing 2×10$^6$ DU145 cells, which produce human VEGF to induce angiogenesis. Mice were injected i.p. on days 0 and 3 with vehicle control or 0.1, 1, or 5 mg/kg XPA.10.064, XPA.10.072, or Bevacizumab. On day 7, mice were sacrificed and Matrigel® plugs were excised, weighed, and photographed. Plugs were given a visual score of 0 to 3 based on the following scheme: 0, no color or obvious vessels; 1, hint of color and few vessels; 2, yellow-red with distinct vessels; and 3, homogenous red or pink with dark vessels (FIG. 14). Plugs were evaluated by blinded scorers who received photographs in which the plug order was scrambled.

Figure 15:
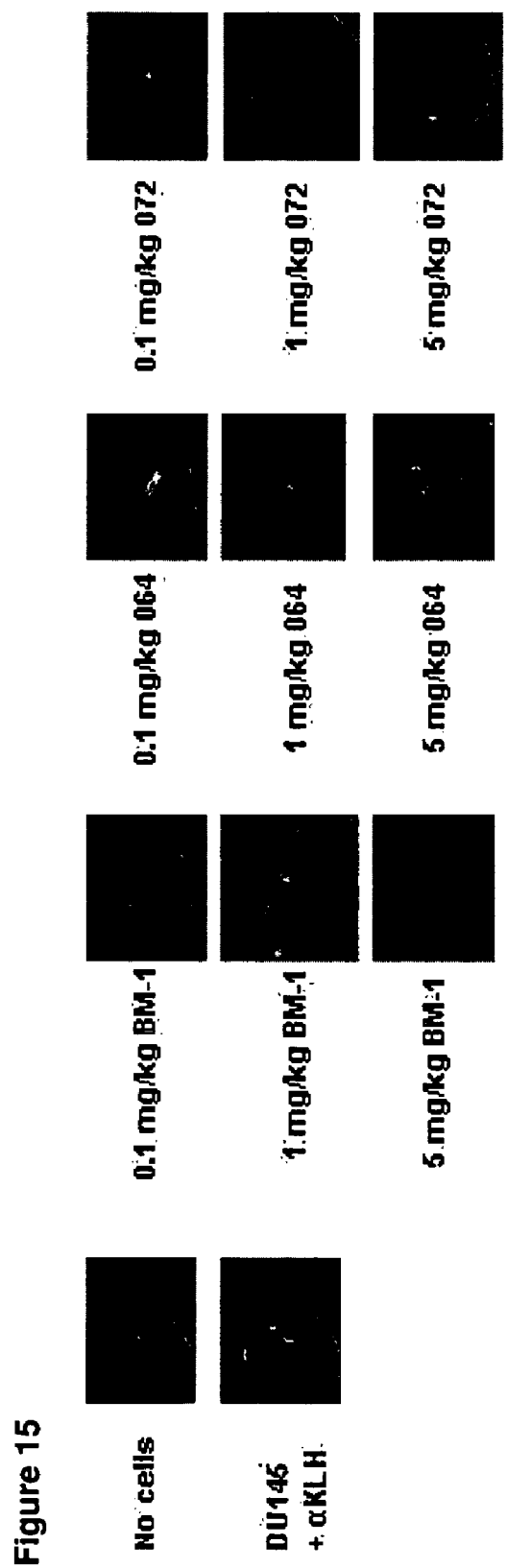
FIG. 15: Matrigel® plug assay showing the level of angiogenesis inhibition in the presence of Bevacizumab (BM-1), XPA.10.064 (064), and XPA.10.072 (072) at various dosages.
Figure 16:
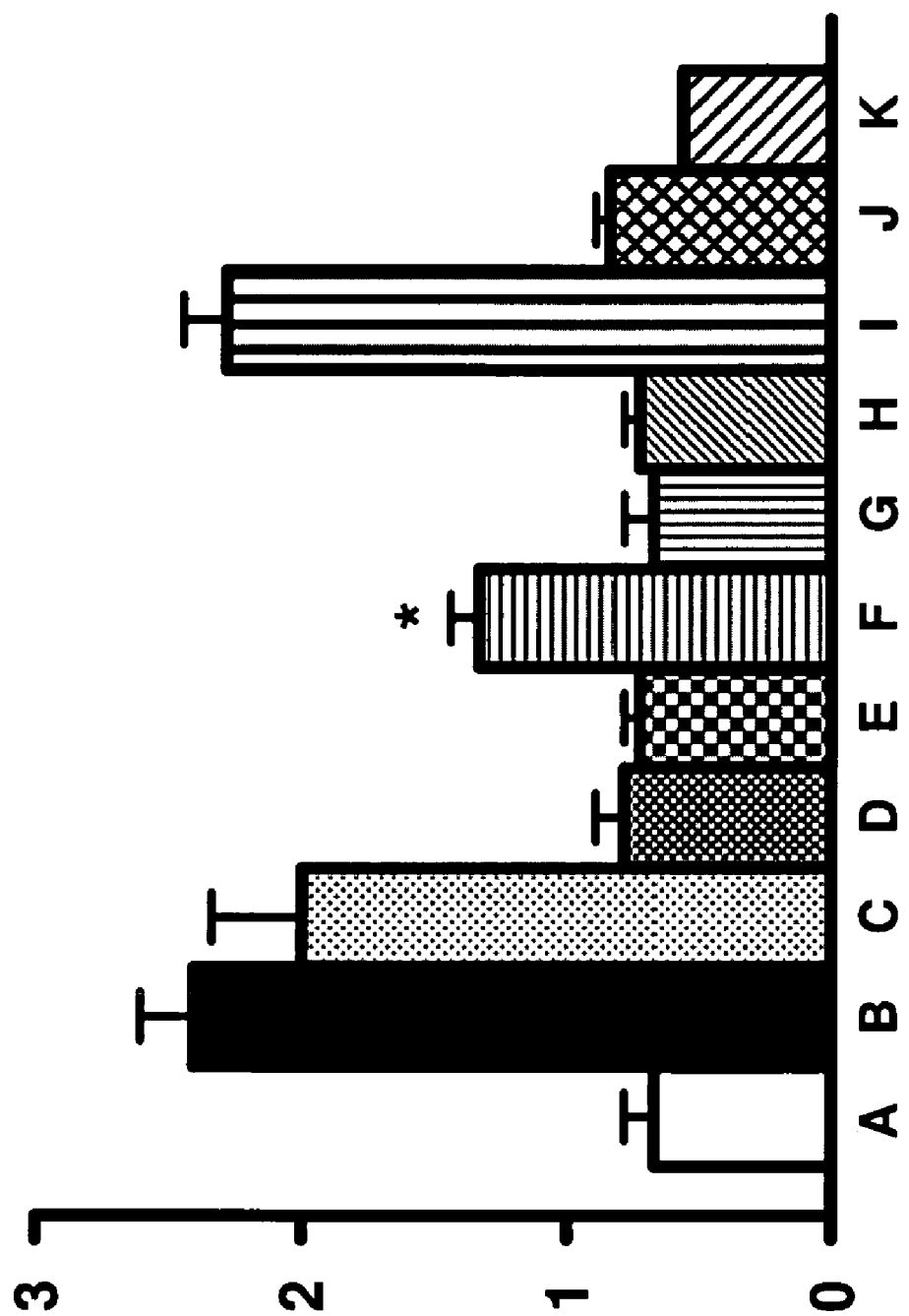
FIG. 16: Inhibition of angiogenesis as determined by Matrigel® plug assay. Numbers are the mean of results from two blinded scorers. (A) no cells; (B) DU145 plus αKLH; (C) Bevacizumab (0.1 mg/kg); (D) Bevacizumab (1 mg/kg); (E) Bevacizumab (5 mg/kg); (F) XPA.10.064 (0.1 mg/kg); (G) XPA.10.064 (1 mg/kg); (H) XPA.10.064 (5 mg/kg); (I) XPA.10.072 (0.1 mg/kg); (J) XPA.10.072 (1 mg/kg); (K) XPA.10.072 (5 mg/kg).

Administration of XPA.10.064 resulted in a significant decrease in angiogenesis at all dosages tested, while administration of XPA.10.072 resulted in a significant decrease at 1 mg/kg and 5 mg/kg (FIGS. 15 & 16). The level of angiogenesis inhibition was similar to that observed in the presence of Bevacizumab.

XPA.10.064, XPA.10.072, and Bevacizumab concentrations in mouse serum were measured by ELISA at four days after the last antibody dose. There was no significant difference in antibody levels between the three antibodies at any of the dosages tested.

Example 12

Inhibition of Tumor Growth by XPA.10.064 and XPA.10.072

The ability of XPA.10.064 and XPA.10.072 to inhibit tumor growth was tested with the A673 Rhabdomyosarcoma tumor growth model using a previously disclosed protocol (Liang 2006). A673 cells maintained in culture were grown until confluent, then harvested and re-suspended in sterile 50% Matrigel®. Xenografts were established by s.c. injection of 5×10$^6$ cells in Matrigel® into the flanks of six-week-old female nude mice. When tumor size reached about 100 mm$^3$, mice were randomized into eight groups of ten and injected i.p. with vehicle only (Group 1), 0.5 mg/kg XPA.10.064 IgG2 (Group 2), 5 mg/kg XPA.10.064 IgG2 (Group 3), 0.5 mg/kg XPA.10.072 IgG2 (Group 4), 5 mg/kg XPA.10.072 IgG2 (Group 5), 5 mg/kg isotype control anti-KLH IgG2 (Group 6), 0.5 mg/kg Bevacizumab (Group 7), or 5 mg/kg Bevacizumab (Group 8) twice a week for 18 days (six total doses). Blood and tissue samples were collected at 24, 72, and 168 hours after the last dose.

Figure 17:
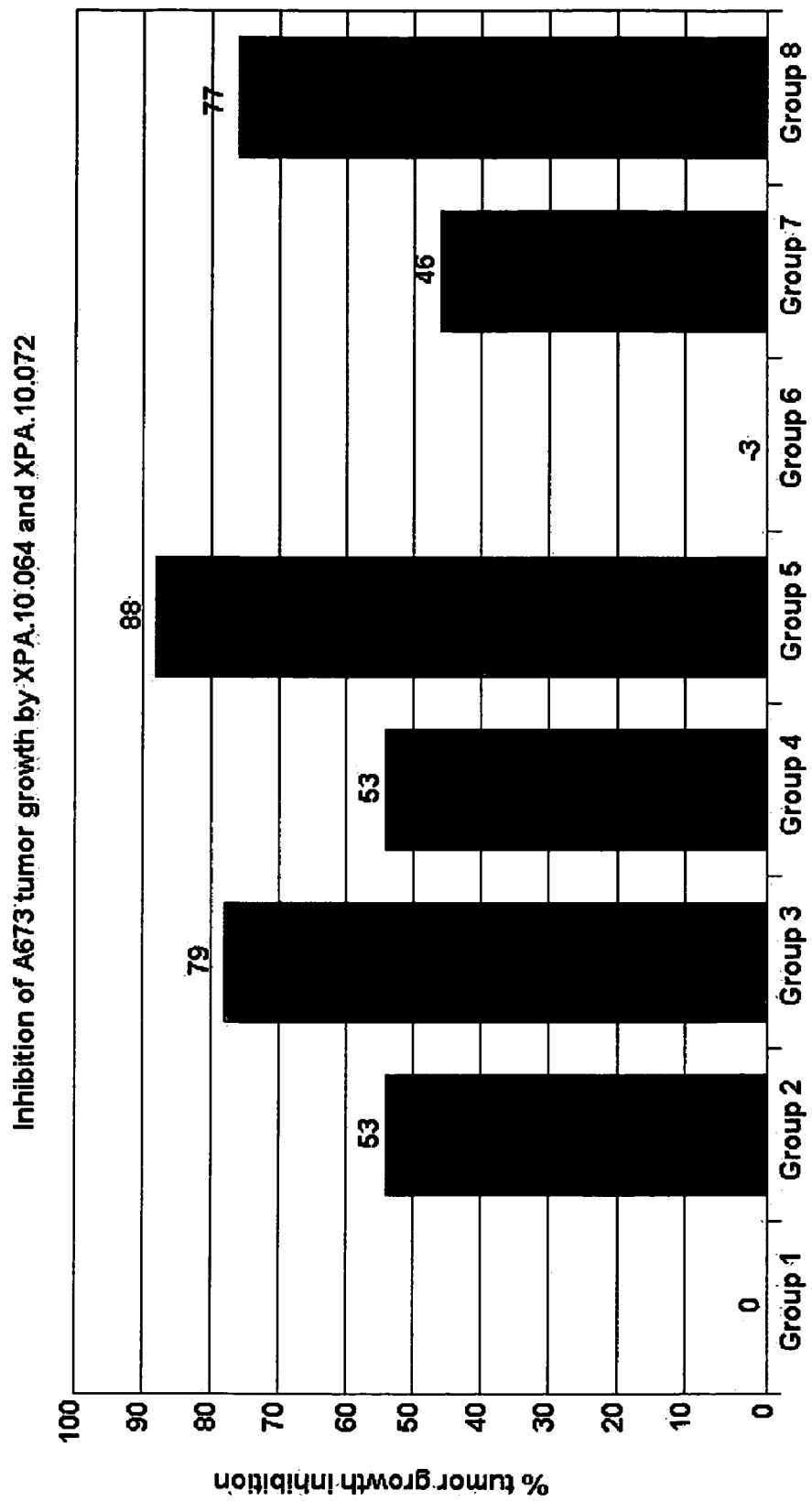
FIG. 17: Inhibition of A673 tumor growth in vivo by XPA.10.064 and XPA.072. (1) Vehicle only; (2) 0.5 mg/kg XPA.10.064 IgG2; (3) 5 mg/kg XPA.10.064 IgG2; (4) 0.5 mg/kg XPA.10.072 IgG2; (5) 5 mg/kg XPA.10.072 IgG2; (6) 5 mg/kg CHO.KLH IgG2; (7) 0.5 mg/kg Bevacizumab; (8) 5 mg/kg Bevacizumab.
Figure 18:
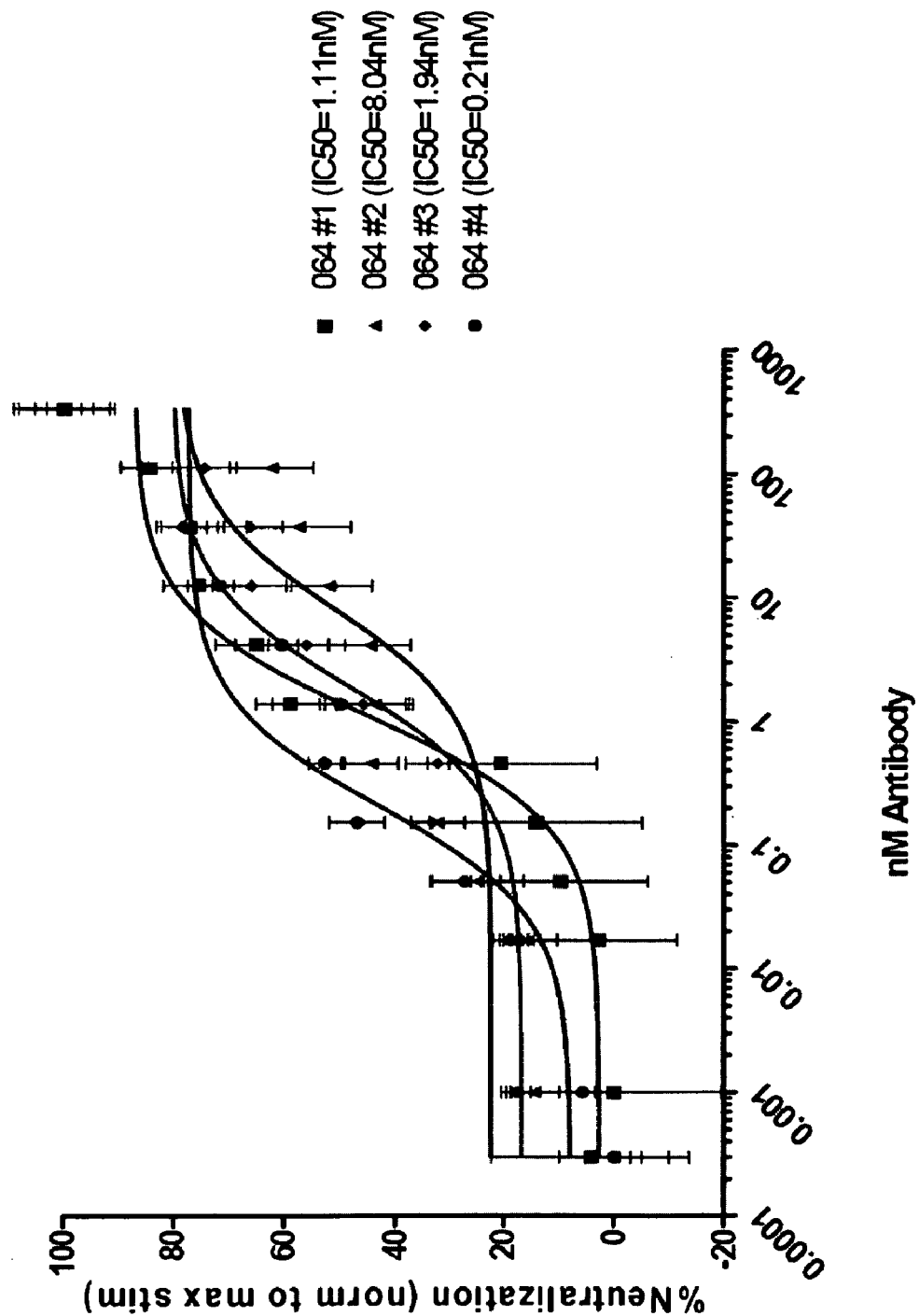
FIG. 18: Inhibition of HUVEC proliferation by XPA.10.064 IgG2 over four separate assays (#'s 1-4).
Figure 19:
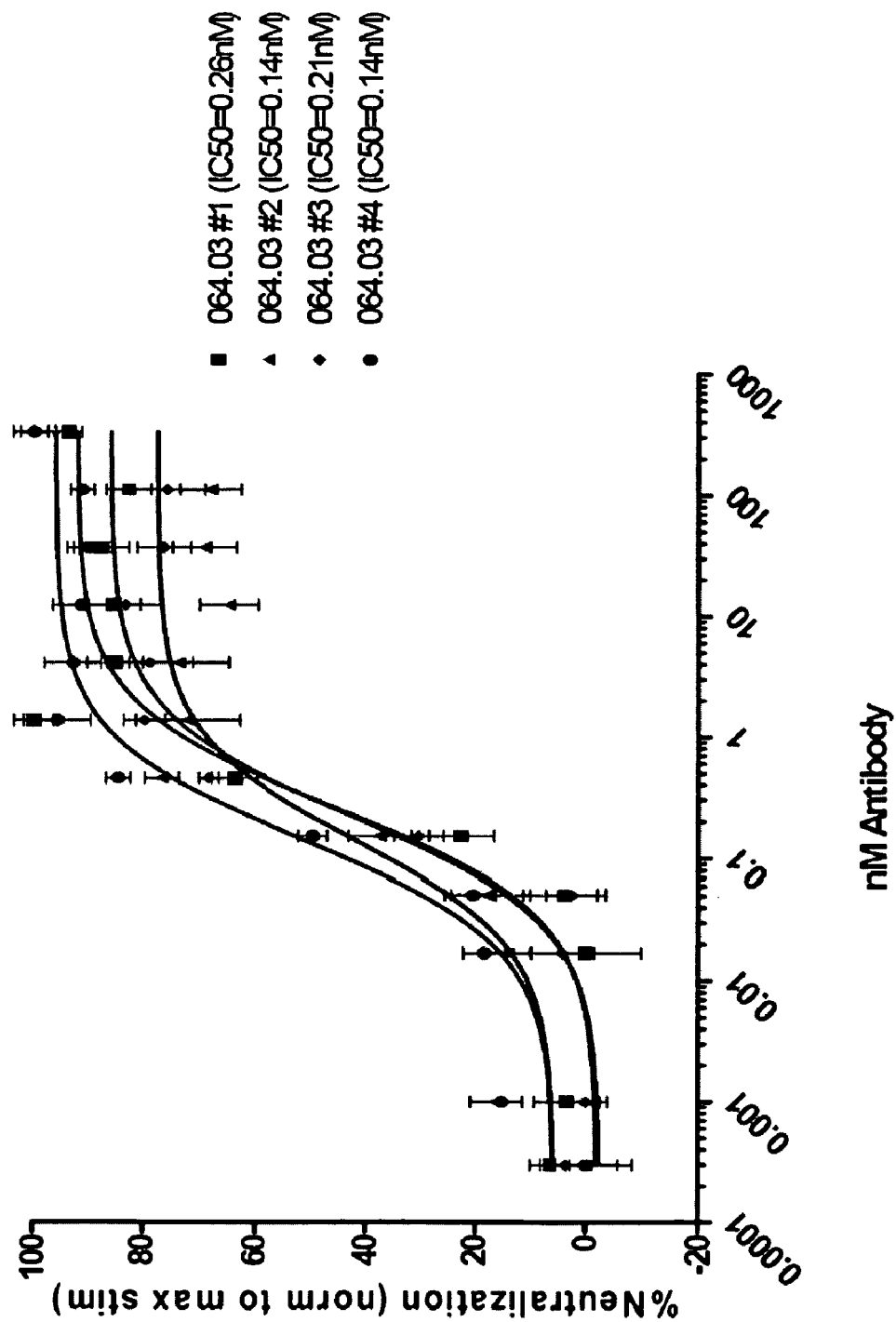
FIG. 19: Inhibition of HUVEC proliferation by XPA.10.064.03 IgG2 over four separate assays (#'s 1-4).
Figure 20:
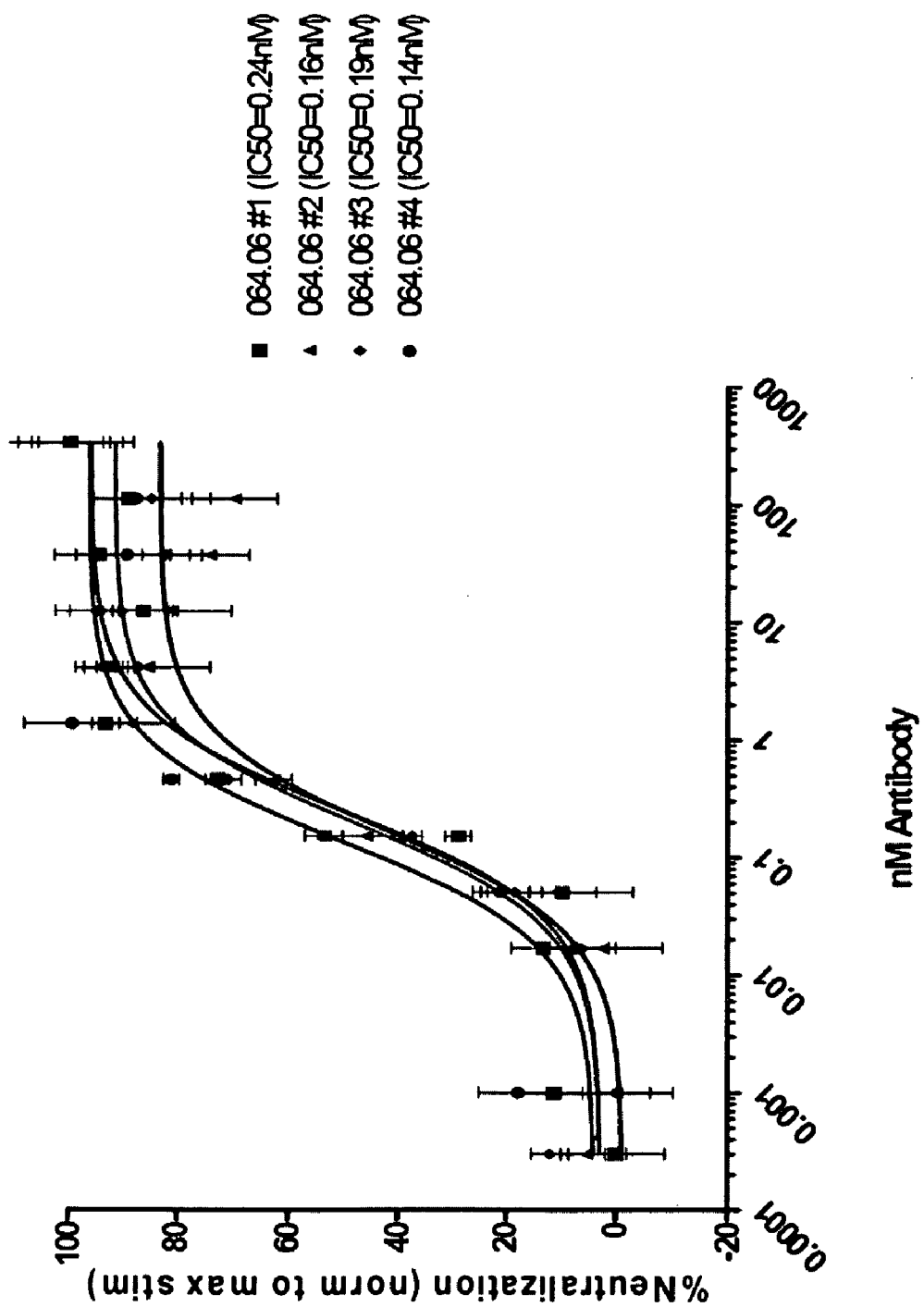
FIG. 20: Inhibition of HUVEC proliferation by XPA.10.064.06 IgG2 over four separate assays (#'s 1-4).
Figure 21:
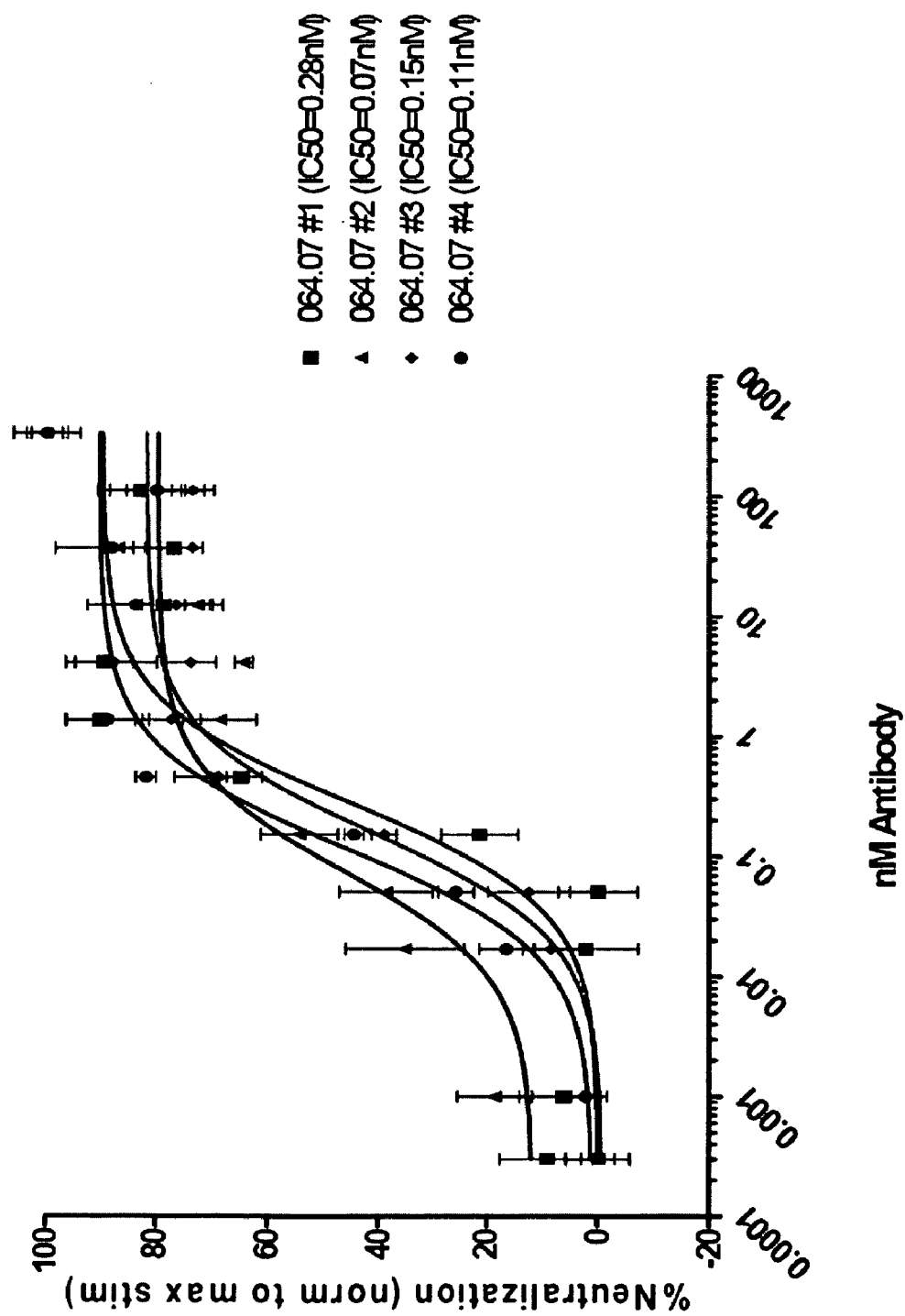
FIG. 21: Inhibition of HUVEC proliferation by XPA.10.064.07 IgG2 over four separate assays (#'s 1-4).
Figure 22:
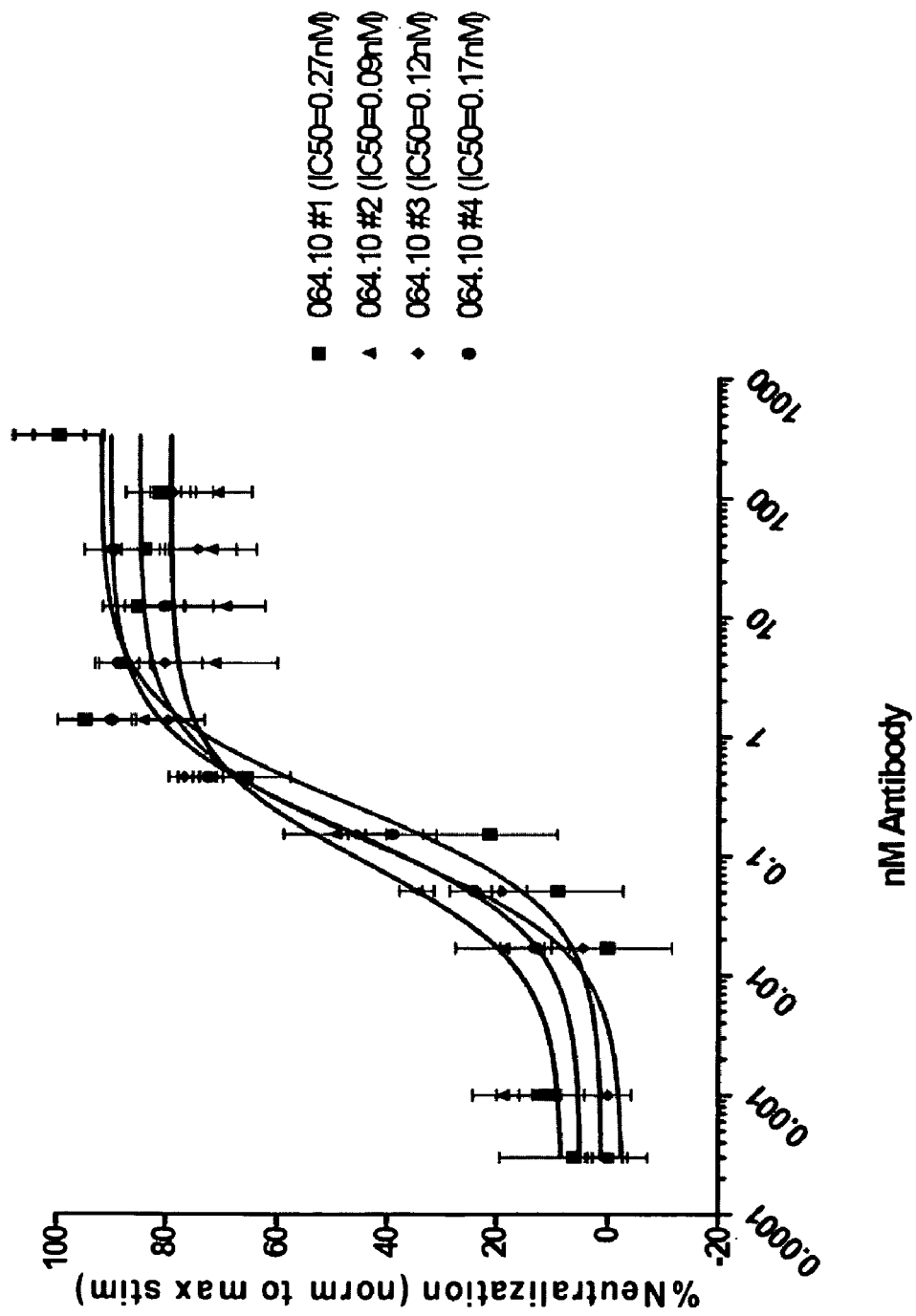
FIG. 22: Inhibition of HUVEC proliferation by XPA.10.064.10 IgG2 over four separate assays (#'s 1-4).
Figure 23:
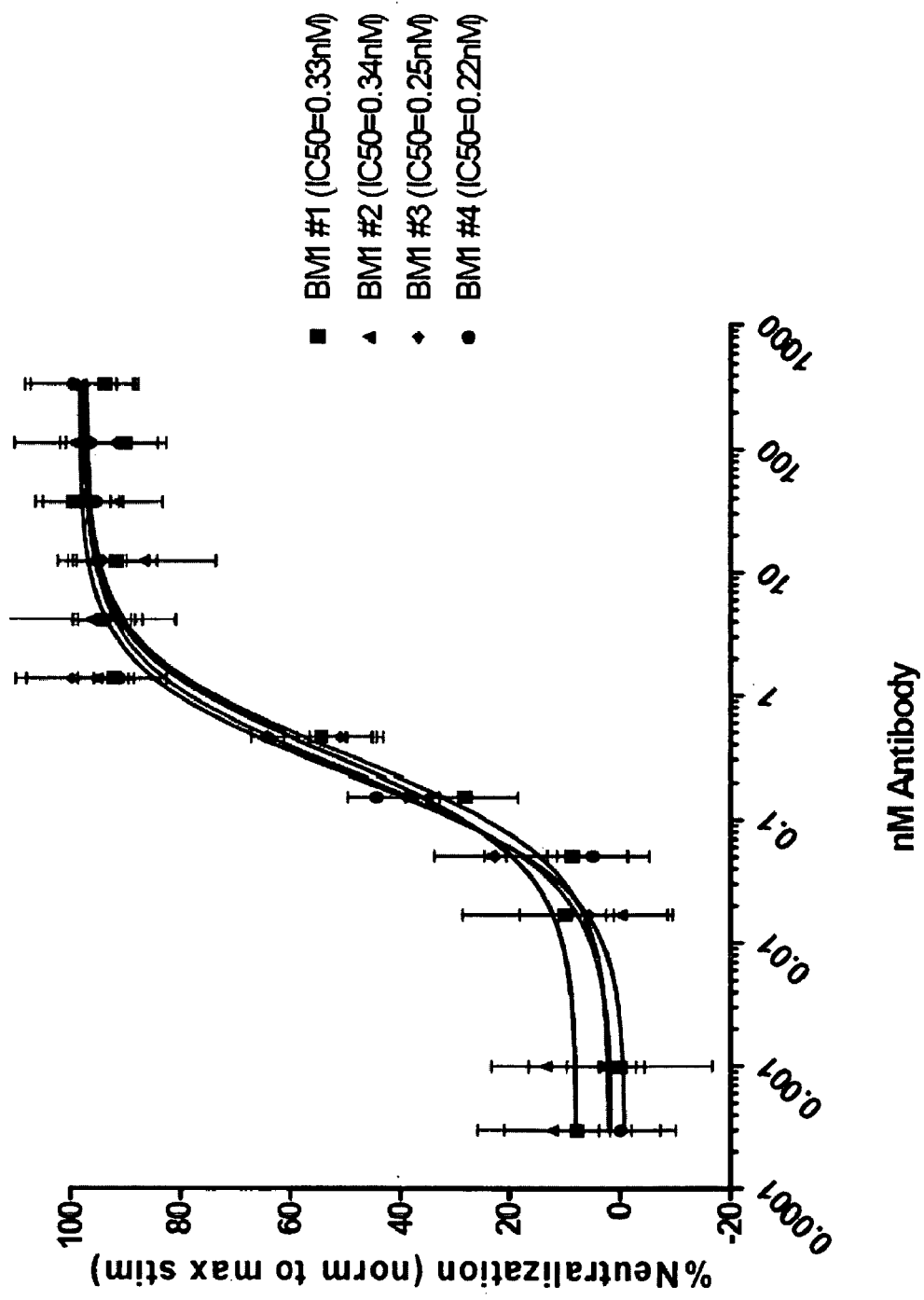
FIG. 23: Inhibition of HUVEC proliferation by Bevacizumab IgG2 over four separate assays (#'s 1-4).

Administration of XPA.10.064 and XPA.10.072 resulted in significant in vivo tumor growth inhibition at both dosages tested (FIG. 17). The level of growth inhibition for both antibodies was slightly higher than that observed with Bevacizumab at all dosages tested. Serum levels were similar for all antibodies administered at a given dosage (0.5 mg/kg, serum level approximately 5-7 µg/ml; 5 mg/kg, serum level approximately 75-100 µg/ml).

Example 13

Affinity Maturation

Affinity maturation was carried out for XPA.10.064 to optimize affinity. scFv libraries were generated by random mutagenesis of HCDR3 using standard molecular biology techniques (see, e.g., Clackson & Lowman, Phage Display—A Practical Approach (Oxford University Press, 2004)). HCDR3 was randomized in two blocks of five amino acids in order to cover the entire 10 amino acid CDR, resulting in libraries H3B1 (N-terminal five amino acid block of HCDR3) and H3B2 (C-terminal five amino acid block of HCDR3). Phage selections were performed on both libraries using techniques similar to those described in Example 1. The coating concentration of target antigen was reduced with each successive round of panning.

Five scFv clones exhibiting improved $k_{off}$ rates for binding to hVEGF$_{165}$ versus the parental antibody were converted to IgGs using techniques similar to those described in Example 3. The VEGF binding affinity of these IgGs was tested on a Biacore 2000® by injecting the antibodies over a very low density antigen surface. Human or murine VEGF$_{165}$ was immobilized via standard amine coupling methods to flow cells on a C1 (planar carboxy surface) chip. Approximately 85 RU of each antigen was immobilized and a reference flow cell was activated and blocked. Antibodies were injected over the chip surface for 400 seconds at two different concentrations, after which dissociation was monitored. Data was analyzed by Scrubber® using double referencing and fitting with a 1:1 interaction. Regenerations were performed with 90 mM HCl with 500 mM NaCl.

The affinity matured clones XPA.10.064.03, XPA.10.064.04, XPA.10.064.06, XPA.10.064.07, and XPA.10.064.10 each bound hVEGF$_{165}$ with greater affinity than parental XPA.10.064 or Bevacizumab (Table 7). The HCDR3 amino sequence for XPA.10.064.03, XPA.10.064.04, XPA.10.064.06, XPA.10.064.07, and XPA.10.064.10 are set forth in SEQ ID NOs:15-19, respectively. The complete heavy chain sequences of XPA.10.064.03, XPA.10.064.04, XPA.10.064.06, XPA.10.064.07, and XPA.10.064.10 are set forth in SEQ ID NOs:20-24, respectively. The light chain sequences of XPA.10.064.03, XPA.10.064.04, XPA.10.064.06, XPA.10.064.07, and XPA.10.064.10 are identical to those of XPA.10.064 and XPA.10.072 (SEQ ID NO:5). All five of these affinity matured antibodies contain a methionine residue in HCDR3.

TABLE 7

Binding affinity of parental and affinity matured XPA.10.064 to hVEGF$_{165}$:

| IgG2 clone | $k_a$ (1/Ms) | $k_d$ (1/s) | $K_D$ |
|---|---|---|---|
| Bevacizumab | $1.92 \times 10^5$ | $8.08 \times 10^{-5}$ | $4.25 \times 10^{-10}$ M (425 pM) |
| XPA.10.064 | $1.93 \times 10^5$ | $3.35 \times 10^{-4}$ | $1.71 \times 10^{-9}$ M (1.71 nM) |
| XPA.10.064.03 | $1.96 \times 10^5$ | $1.80 \times 10^{-5}$ | $9.17 \times 10^{-11}$ M (92 pM) |
| XPA.10.064.04 | $1.50 \times 10^5$ | $2.94 \times 10^{-5}$ | $1.966 \times 10^{-10}$ M (197 pM) |
| XPA.10.064.06 | $1.78 \times 10^5$ | $2.07 \times 10^{-5}$ | $1.21 \times 10^{-10}$ M (121 pM) |
| XPA.10.064.07 | $2.07 \times 10^5$ | $6.65 \times 10^{-6}$ | $3.49 \times 10^{-11}$ M (35 pM) |
| XPA.10.064.10 | $2.16 \times 10^5$ | $1.16 \times 10^{-5}$ | $5.56 \times 10^{-11}$ M (56 pM) |

Parental XPA.10.064 and the affinity matured clones XPA.10.064.06 and XPA.10.064.07 each exhibited only weak binding (>100 nM) binding to mVEGF$_{165}$ (Table 8).

TABLE 8

Binding affinity of parental and affinity matured XPA.064 to mVEGF$_{165}$:

| IgG2 clone | $K_D$ |
|---|---|
| Bevacizumab | No binding |
| XPA.10.064 | 197 nM |
| XPA.10.064.06 | 208 nM |
| XPA.10.064.07 | 130 nM |

Example 14

Inhibition of HUVEC Proliferation by Affinity Matured XPA.10.064

Affinity matured XPA.10.064 IgG2s were tested for their ability to block proliferation of HUVECs using a protocol similar to that described above in Example 9. Titrations of XPA.10.064, XPA.10.064.03, XPA.10.064.06, XPA.10.064.07, XPA.10.064.10, and Bevacizumab were generated, and the antibodies were pre-incubated with hVEGF$_{165}$ for two hours. After pre-incubation, the VEGF/antibody complex was added to the suspended HUVEC cells. The experiment was repeated four times for each antibody.

Figure 24:
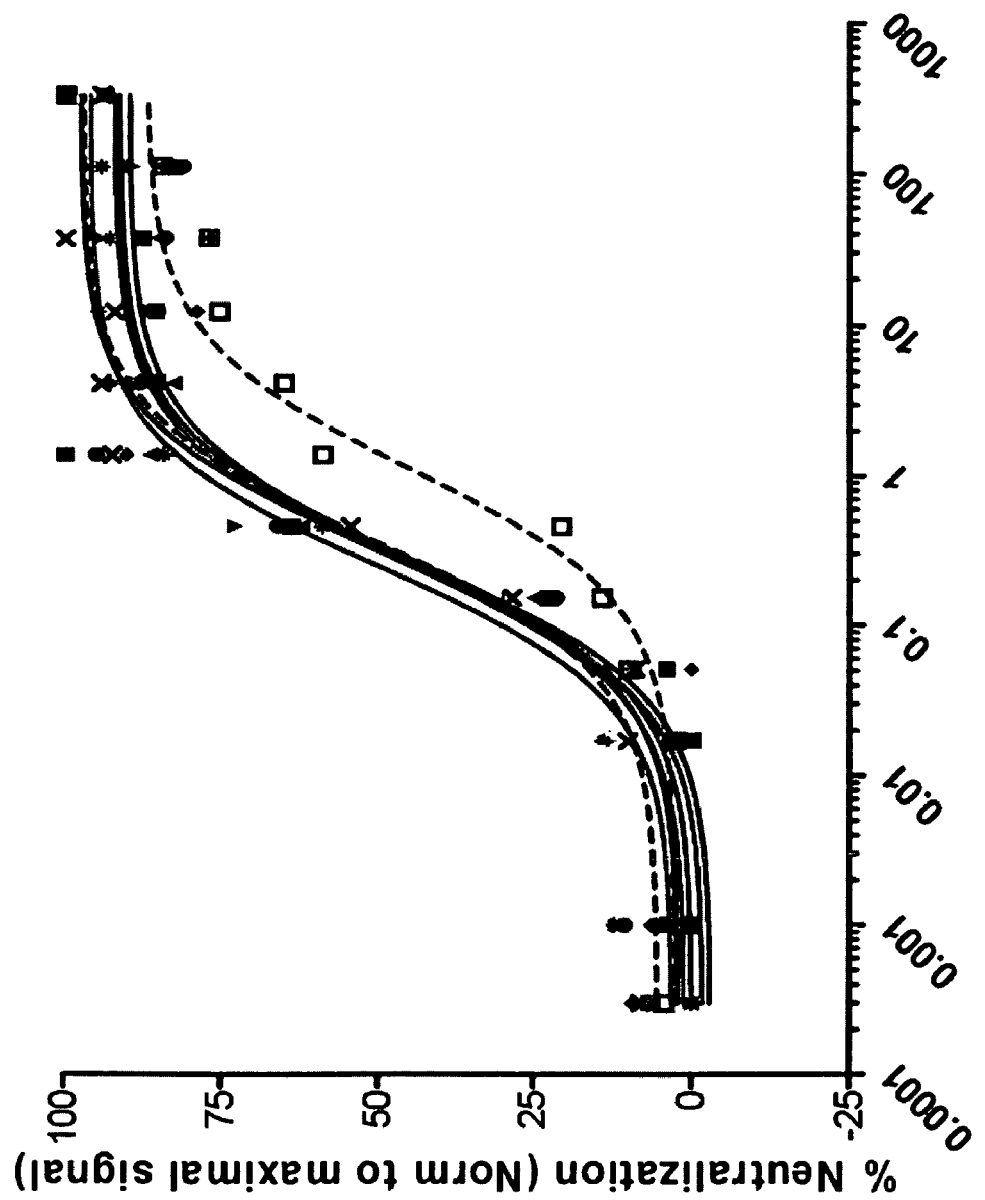
FIG. 24: Inhibition of HUVEC proliferation by XPA.10.064.03 (■), XPA.10.064.04 (▲), XPA.10.064.06 (▼), XPA.10.064.07 (♦), XPA.10.064.10 (●), XPA.10.064 (□), and Bevacizumab (x, *). Results for each antibody are mean of four separate assays.

Individual results for each antibody are set forth in FIGS. 18-23, and the results are summarized in FIG. 24. The affinity matured antibodies XPA.10.064.03, XPA.10.064.04, XPA.10.064.06, XPA.10.064.07, and XPA.10.064.10 each inhibited HUVEC proliferation to a greater degree than parental XPA.10.064. The geometric mean IC$_{50}$ for each antibody is set forth in Table 9. The P-values presented in Table 9 are based on a paired within experiment one-tailed t-test on log(IC$_{50}$) for each antibody relative to that of Bevacizumab. In this analysis, the affinity matured XPA.10.064.03, XPA.10.064.06, XPA.10.064.07, and XPA.10.064.10 antibodies were not statistically different from one another.

TABLE 9

Affinity matured XPA.10.064 HUVEC assay summary:

| Antibody | Geometric mean IC$_{50}$ (SE) | P-value (power to detect 2X change in IC$_{50}$) |
|---|---|---|
| Bevacizumab | 275 pM (29) | — |
| XPA.10.064 | 1320 pM (984) | — (10%) |
| XPA.10.064.03 | 174 pM (29) | 0.0394 (90%) |
| XPA.10.064.06 | 173 pM (22) | 0.0132 (98%) |
| XPA.10.064.07 | 129 pM (40) | 0.0525 (40%) |
| XPA.10.064.10 | 139 pM (38) | 0.04625 (50%) |

Example 15

Inhibition of Tumor Growth by XPA.10.064.06

The ability of XPA.10.064.06 to inhibit tumor growth was tested using the same A673 Rhabdomyosarcoma tumor growth model discussed above in Example 12. $2.5 \times 10^6$ tumor cells were injected s.c. in 50% Matrigel® into the midline thoracic vertebral region of six-week old nude mice starting at day 0. At day 3, when tumor size had reached about 200 mm$^3$, mice were randomized into seven groups of 20 mice and injected i.p. twice a week with isotype control anti-KLH IgG2, XPA.10.064.06 at 0.1, 0.5, or 5 mg/kg, or Bevacizumab at 0.1, 0.5, or 5 mg/kg. Tumor size was measured on days 3, 7, 10, 14, 17, 21, 24, 28, and 31. Mice were sacrificed if and when tumor size reached 2000 mm$^3$. Tumors and serum samples were collected following the final tumor measurement for each mouse.

Figure 25:
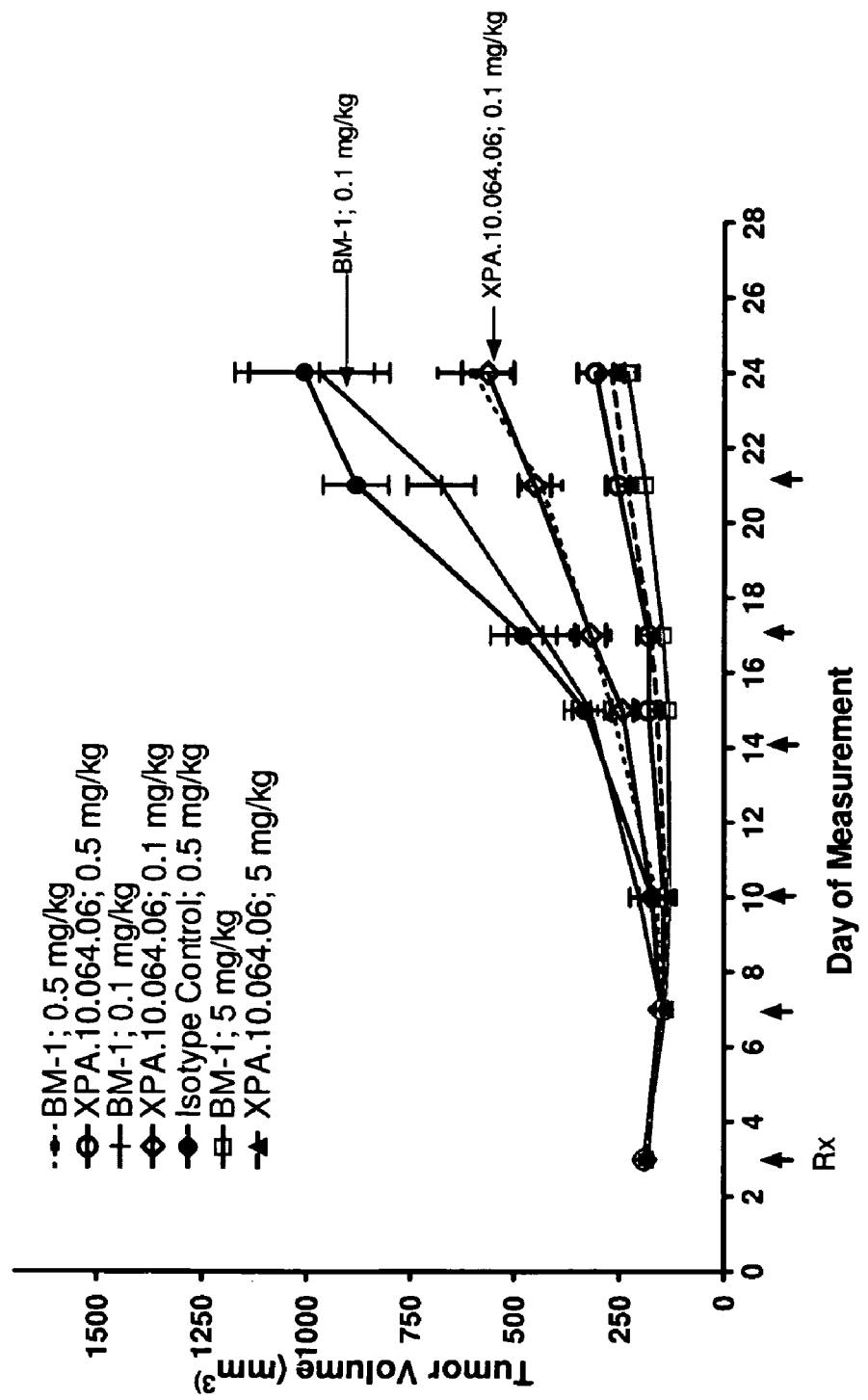
FIG. 25: Inhibition of A673 tumor growth in vivo by XPA.10.064.06 and Bevacizumab through day 24. (●) 0.5 mg/kg isotype control antibody; (▼) 0.1 mg/kg Bevacizumab; (♦) 0.1 mg/kg XPA.10.064.06 IgG2; (■) 0.5 mg/kg Bevacizumab; (▲) 0.5 mg/kg XPA.10.064.06 IgG2; (□) 5 mg/kg Bevacizumab; and (Δ) 5 mg/kg XPA.10.064.06 IgG2. Arrows on X-axis indicate dosing days.
Figure 26:
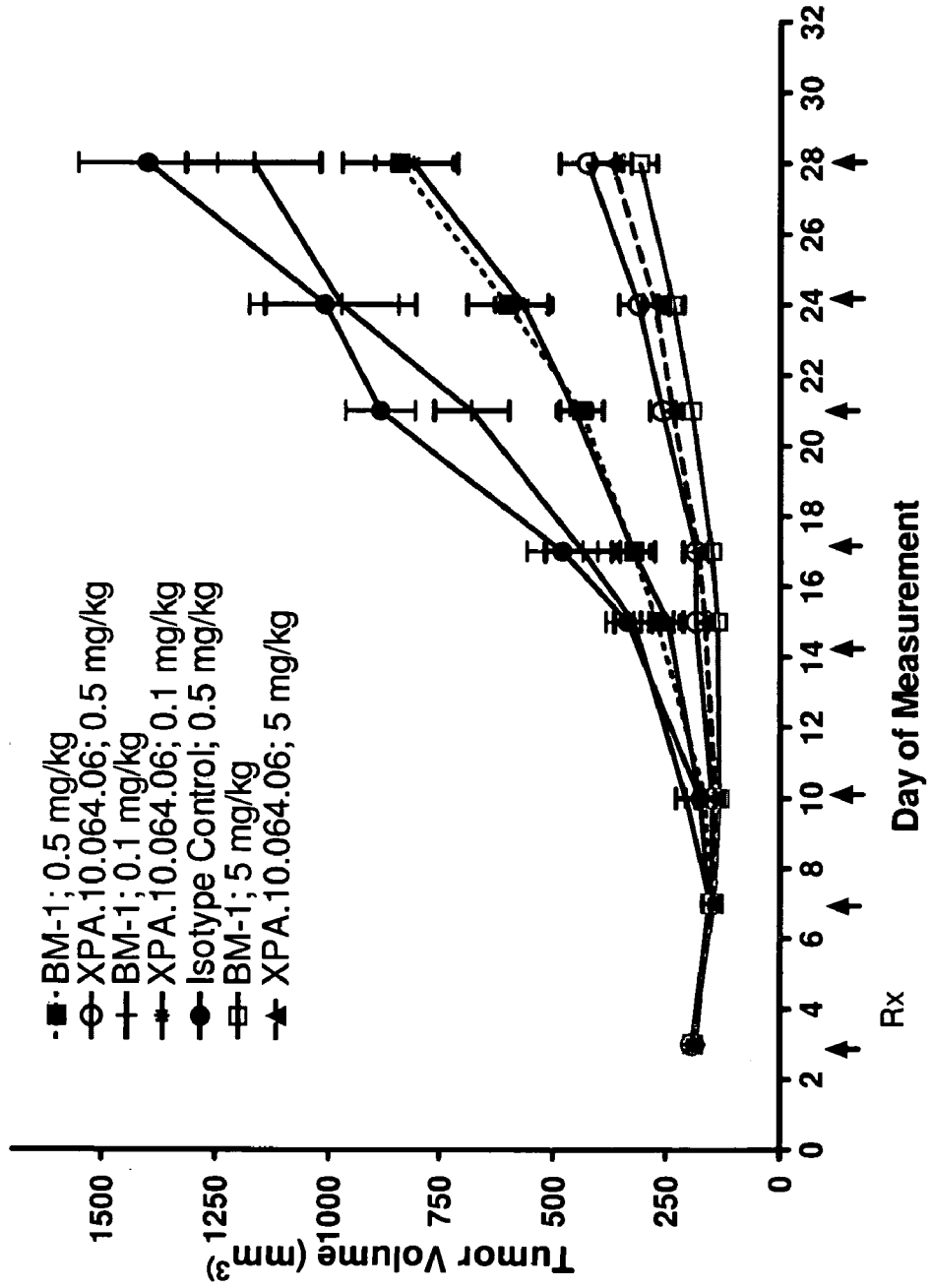
FIG. 26: Inhibition of A673 tumor growth in vivo by XPA.10.064.06 and Bevacizumab through day 28. (●) 0.5 mg/kg isotype control antibody; (▼) 0.1 mg/kg Bevacizumab; (♦) 0.1 mg/kg XPA.10.064.06 IgG2; (■) 0.5 mg/kg Bevacizumab; (▲) 0.5 mg/kg XPA.10.064.06 IgG2; (□) 5 mg/kg Bevacizumab; and (Δ) 5 mg/kg XPA.10.064.06 IgG2. Arrows on X-axis indicate dosing days.
Figure 27:
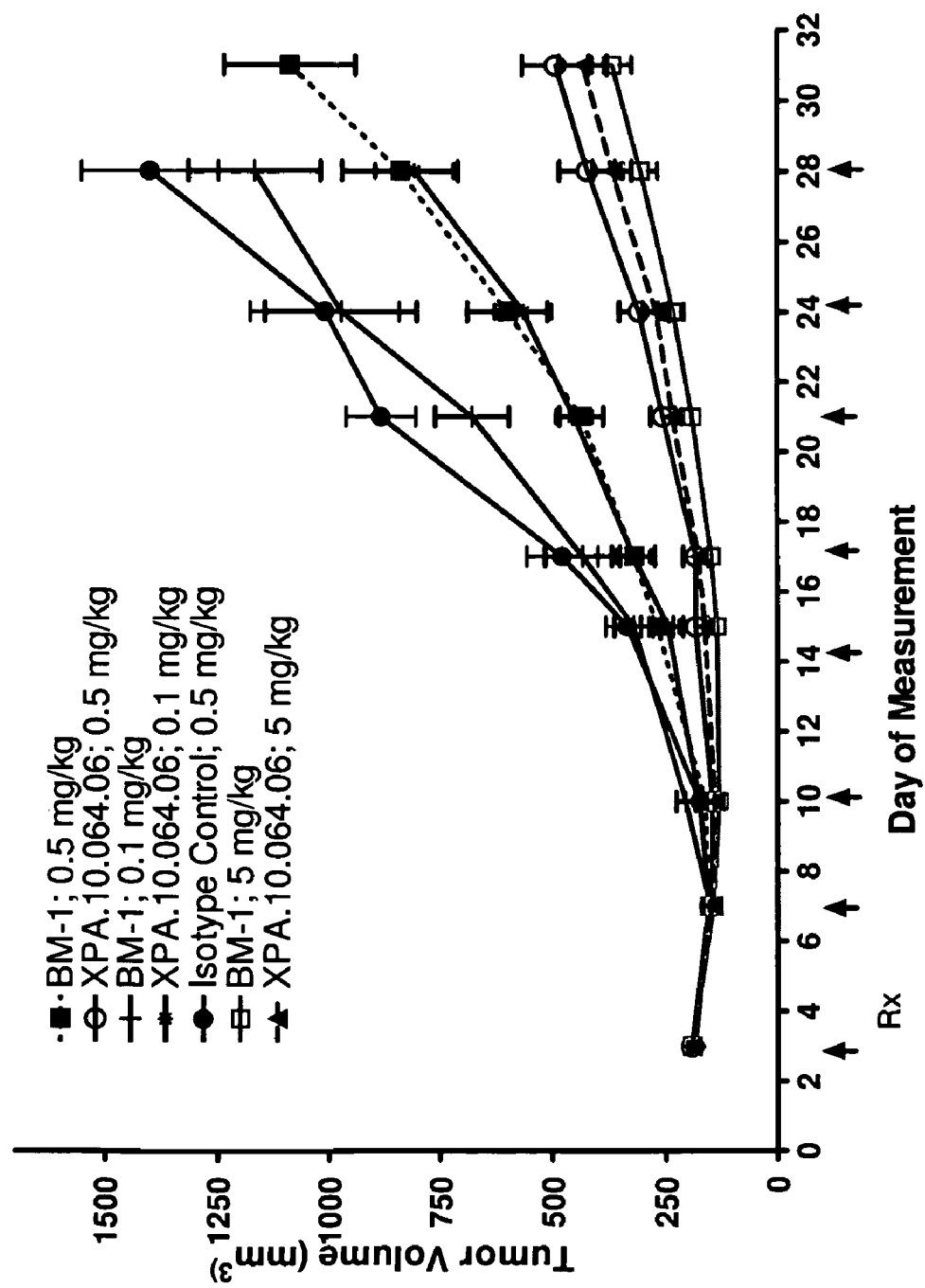
FIG. 27: Inhibition of A673 tumor growth in vivo by XPA.10.064.06 and Bevacizumab through day 31. (●) 0.5 mg/kg isotype control antibody; (▼) 0.1 mg/kg Bevacizumab; (♦) 0.1 mg/kg XPA.10.064.06 IgG2; (■) 0.5 mg/kg Bevacizumab; (▲) 0.5 mg/kg XPA.10.064.06 IgG2; (□) 5 mg/kg Bevacizumab; and (Δ) 5 mg/kg XPA.10.064.06 IgG2. Arrows on X-axis indicate dosing days.

XPA.10.064.06 and Bevacizumab both inhibited tumor growth in a dose-dependent manner (FIGS. 25-27). Treatment with 0.5 mg/kg XPA.10.064.06 resulted in tumor regression through day 17, with tumor size remaining below 200 mm$^3$ (FIGS. 25-27). Mice treated with 0.1 or 0.5 mg/kg XPA.10.064.06 exhibited significantly smaller tumors at days 17, 21, 24, 28, and 31 than mice treated with Bevacizumab at the same dosages (FIGS. 25-27). Three mice treated with Bevacizumab at 0.1 mg/kg and three treated with control antibody had to be sacrificed on day 24 because they had tumor volumes exceeding 2000 mm$^3$, whereas none of the mice treated with XPA.10.064.06 reached this threshold over the course of the study.

The percent tumor growth inhibition (% TGI) at day 24 (the last measurement day on which all animals were alive) in mice treated with 0.1 mg/kg XPA.10.064.06 (55%) was similar to that obtained for Bevacizumab at five times the dosage (50% at 0.5 mg/kg). Similarly, the % TGI in mice treated with XPA.10.064.06 at 0.5 mg/kg (85%) was similar to that observed in mice treated with ten times the dosage of Bevacizumab (95% at 5 mg/kg). These results show that XPA.10.064.06 is at least five times more effective at reducing tumor growth in vivo than Bevacizumab. Percent tumor growth inhibition results for each antibody at day 24 are summarized in Table 10.

TABLE 10

Inhibition of tumor growth by XPA.10.064.06

| Antibody comparison | % tumor growth inhibition | P-value (determined by Anova followed by Tukey test) |
| --- | --- | --- |
| Control vs. BM-1 (0.1 mg/kg) | No effect | — |
| Control vs. XPA.10.064.06 (0.1 mg/kg) | 55% | p < 0.01 |
| Control vs. BM-1 (0.5 mg/kg) | 50% | p < 0.01 |
| Control vs. XPA.10.064.06 (0.5 mg/kg) | 85% | p < 0.01 |
| Control vs. BM-1 (5 mg/kg) | 95% | p < 0.01 |
| Control vs. XPA.10.064.06 (5 mg/kg) | 90% | p < 0.01 |

Tumor growth delay by each antibody was calculated as the difference in the number of days it took for a tumor to reach 500 mm$^3$ following treatment with the antibody versus control. Tumor growth delay was significantly longer for XPA.10.064.06 than for BM-1 at the 0.5 mg/kg dosage (14 days versus 5 days, respectively) and at the 0.1 mg/kg dosage (7 days versus 2 days, respectively). These results show that XPA.10.064.06 delays tumor growth to a specified size for a duration at least two to three times longer than Bevacizumab when the antibodies are administered at the same dosage. Results are summarized in Table 11.

TABLE 11

Tumor growth delay by XPA.10.064.06

| Antibody (dosage) | Tumor growth delay (days) |
| --- | --- |
| Control huIgG (0.5 mg/kg) | 0 |
| XPA.10.064.06 (0.1 mg/kg) | 7 |
| BM-1 (0.1 mg/kg) | 2 |
| XPA.10.064.06 (0.5 mg/kg) | 14 |
| BM-1 (0.5 mg/kg) | 5 |

Area under the curve (AUC) calculations based on tumor volume versus time were performed at day 28 for each antibody/dosage. The AUC for BM-1 at 0.5 mg/kg was significantly higher than that of XPA.10.064.06 at the same dosage (8865 versus 5517, respectively). Although the difference was less marked, the AUC for BM-1 was also higher than that of XPA.10.064.06 at 0.1 mg/kg (9638 versus 8703, respectively). Results are summarized in Table 12.

TABLE 12

Area under the curve for XPA.10.064

| Antibody (dosage) | AUC (tumor volume × days) |
| --- | --- |
| Control huIgG (0.5 mg/kg) | 11015 |
| XPA.10.064.06 (0.1 mg/kg) | 8703 |
| BM-1 (0.1 mg/kg) | 9638 |
| XPA.10.064.06 (0.5 mg/kg) | 5517 |
| BM-1 (0.5 mg/kg) | 8865 |
| XPA.10.064.06 (5 mg/kg) | 5069 |
| BM-1 (5 mg/kg) | 4418 |

The ability of XPA.10.064.06 to inhibit tumor growth was further tested in the HT-29 human colorectal adenocarcinoma model. Preliminary results indicated that twice-weekly administration of XPA.10.064.06 at 0.1, 0.5, or 5 mg/kg did not result in a statistically significant reduction in tumor size over 35 days. Similar results were obtained with Bevacizumab at the same concentrations.

Example 16

Inhibition of Affinity-Matured Antibody Oxidation

As discussed above in Example 13, the affinity matured antibodies XPA.10.064.03, XPA.10.064.04, XPA.10.064.06, XPA.10.064.07, and XPA.10.064.10 each contain a methionine residue in HCDR3 (specifically, at residue 101) that is not present in the parental antibody. Oxidation of methionine residues is a common degradation pathway for protein products during storage.

To test the effect of methionine oxidation on the affinity matured antibodies, XPA.10.064.06 and parental XPA.10.064 were both exposed to the oxidizing agent tert-butylhydroperoxide (tBHP). The degree of resultant oxidation at each methionine residue was analyzed by tryptic mapping followed by liquid chromatography-mass spectrometry (LC/MS). Results are summarized in Table 13. Both antibodies exhibited oxidation at methionine residues 48 and 81, and no measurable oxidation at methionine residue 70. The extra methionine residue in XPA.10.064.06 at position 101 exhibited a significant degree of oxidation.

TABLE 13

Oxidation of methionine residues
in XPA.10.064 and XPA.10.064.06

| Methionine residue | Degree of oxidation (%) | |
|---|---|---|
| | XPA.10.064 | XPA.10.064.06 |
| Met-48 | 39 | 20 |
| Met-70 | 0 | 0 |
| Met-81 | 28 | 14 |
| Met-101 | N/A | 66 |

Figure 28A:
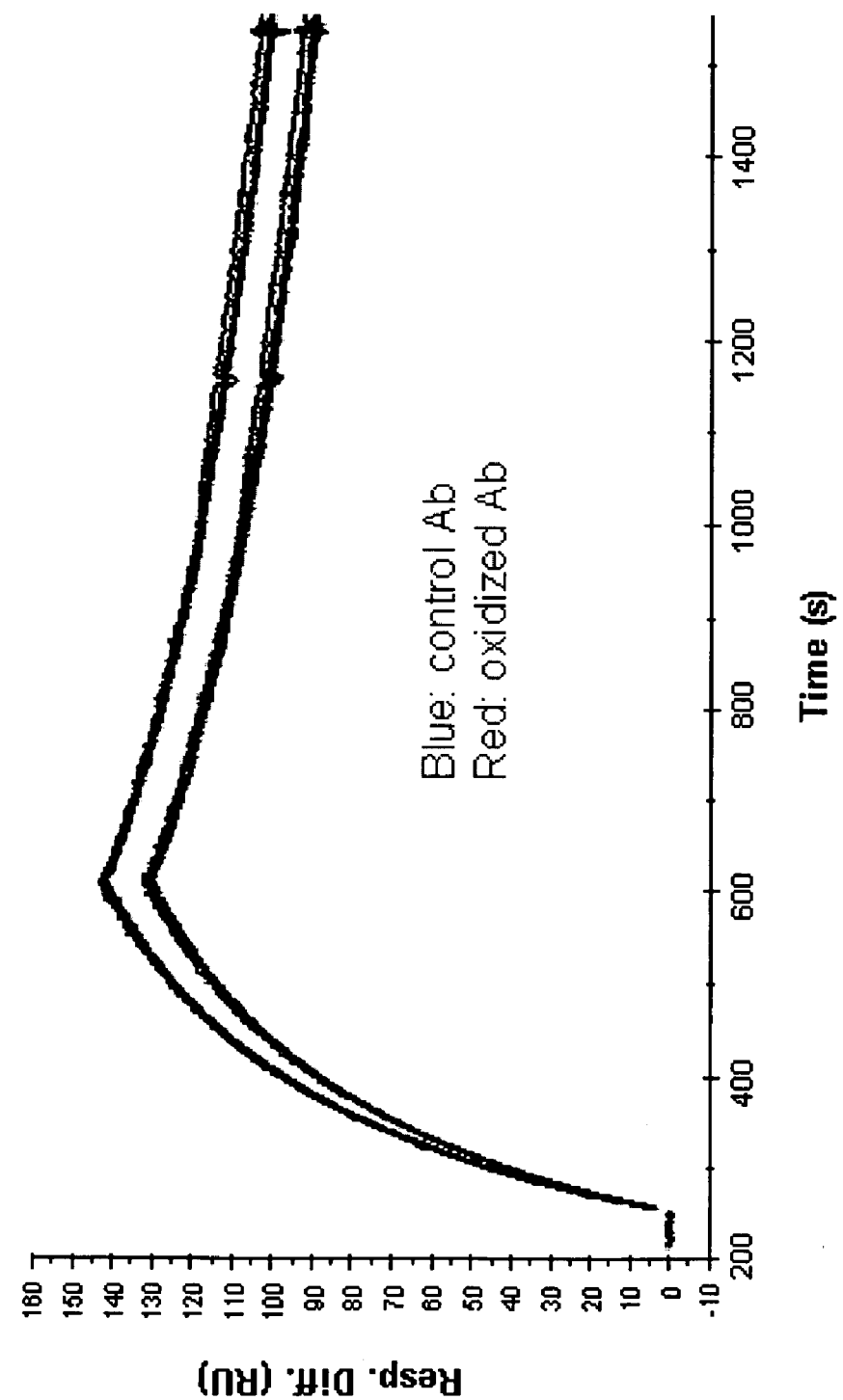
FIG. 28: Effect of antibody methionine oxidation on hVEGF$_{165}$ binding. A. Biacore analysis of XPA.10.064 binding to hVEGF$_{165}$ in the presence or absence of methionine oxidation. B. Biacore analysis of XPA.10.064.06 binding to hVEGF$_{165}$ in the presence or absence of methionine oxidation.
Figure 28B:
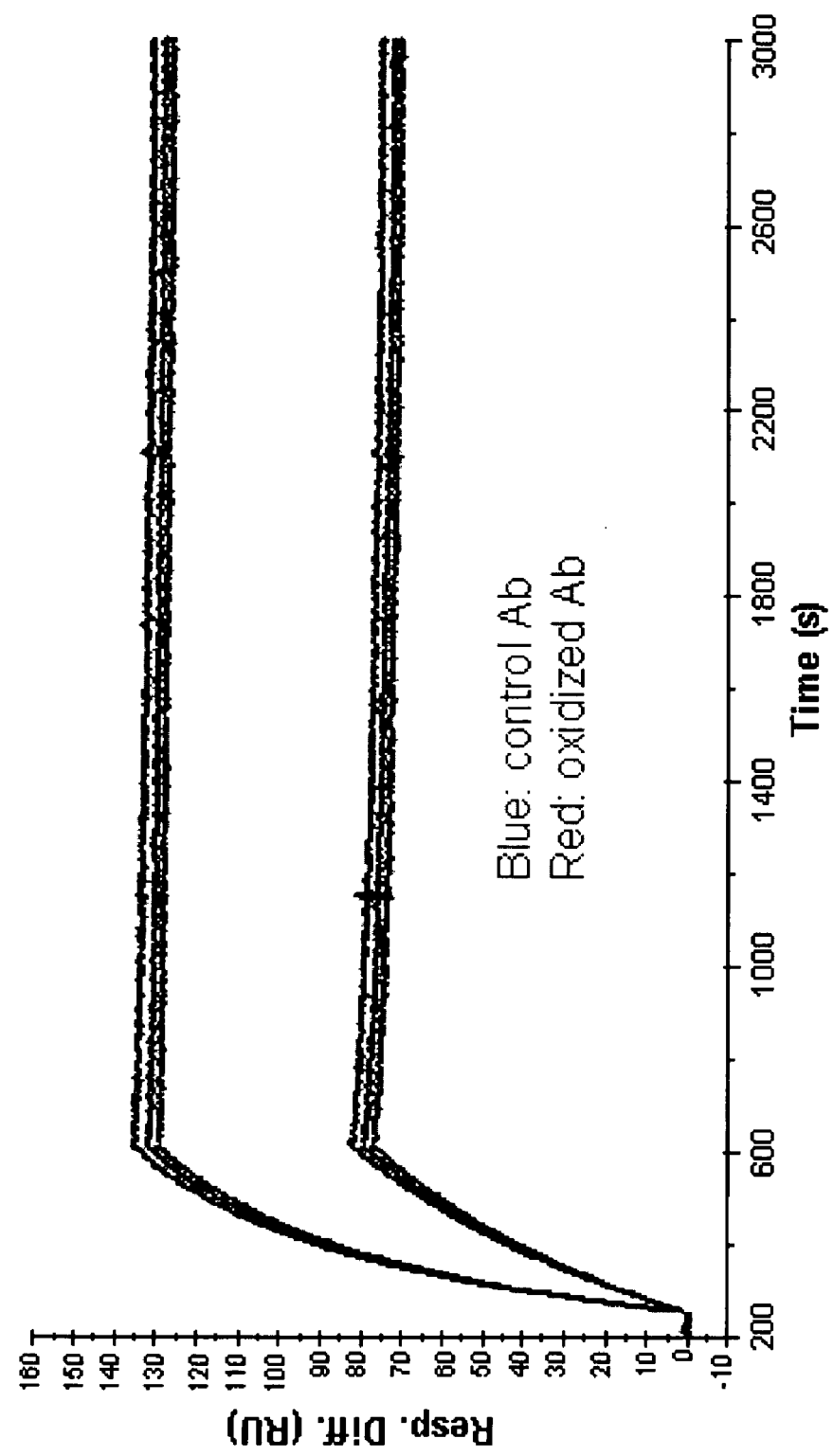

The binding kinetics of the oxidized antibodies for hVEGF$_{165}$ were analyzed by Biacore. Oxidation of XPA.10.064 had little effect on hVEGF$_{165}$ binding kinetics (FIG. 28A), while oxidation of XPA.10.064.06 resulted in a significant decrease in in vitro VEGF binding affinity (FIG. 28B).

Figure 29A:
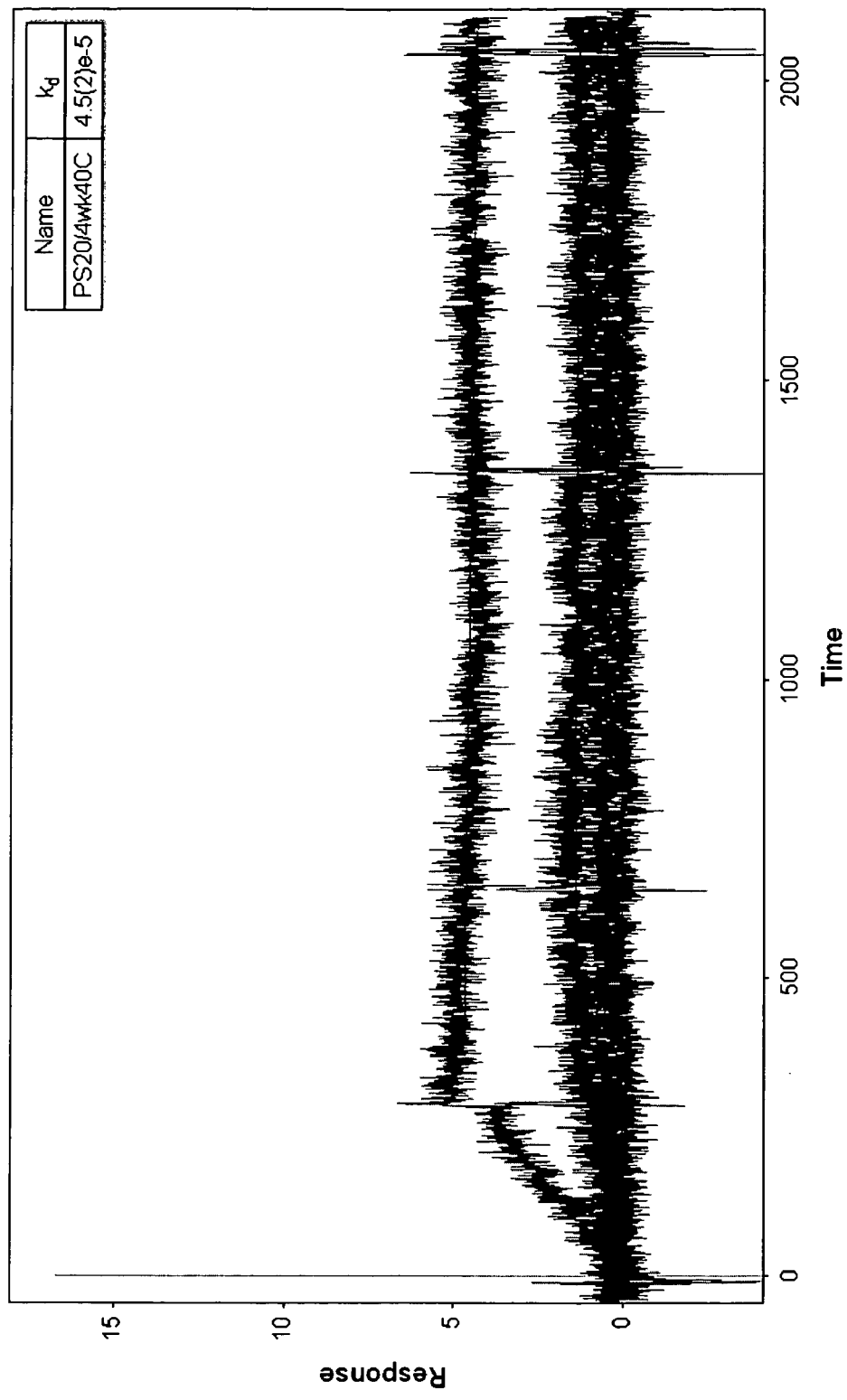
FIG. 29: Effect of methionine on XPA.10.064.06 binding to hVEGF$_{165}$ following thermal stress oxidizing conditions. A. Biacore analysis of XPA.10.064.06 binding to hVEGF$_{165}$ following thermal stress oxidation. B. Biacore analysis of XPA.10.064.06 binding to hVEGF$_{165}$ following thermal stress oxidation in the presence of methionine.
Figure 29B:
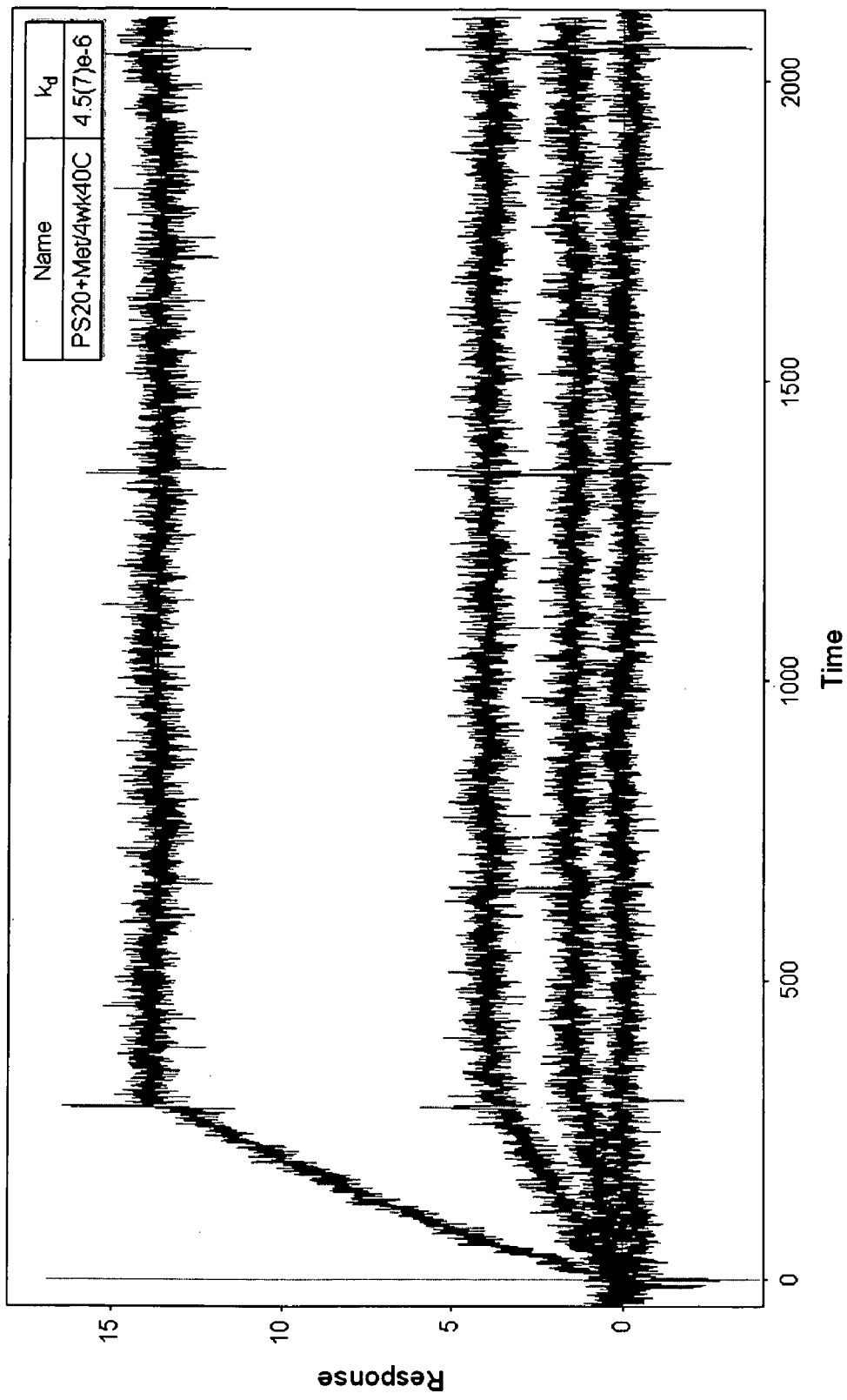
Figure 30A:
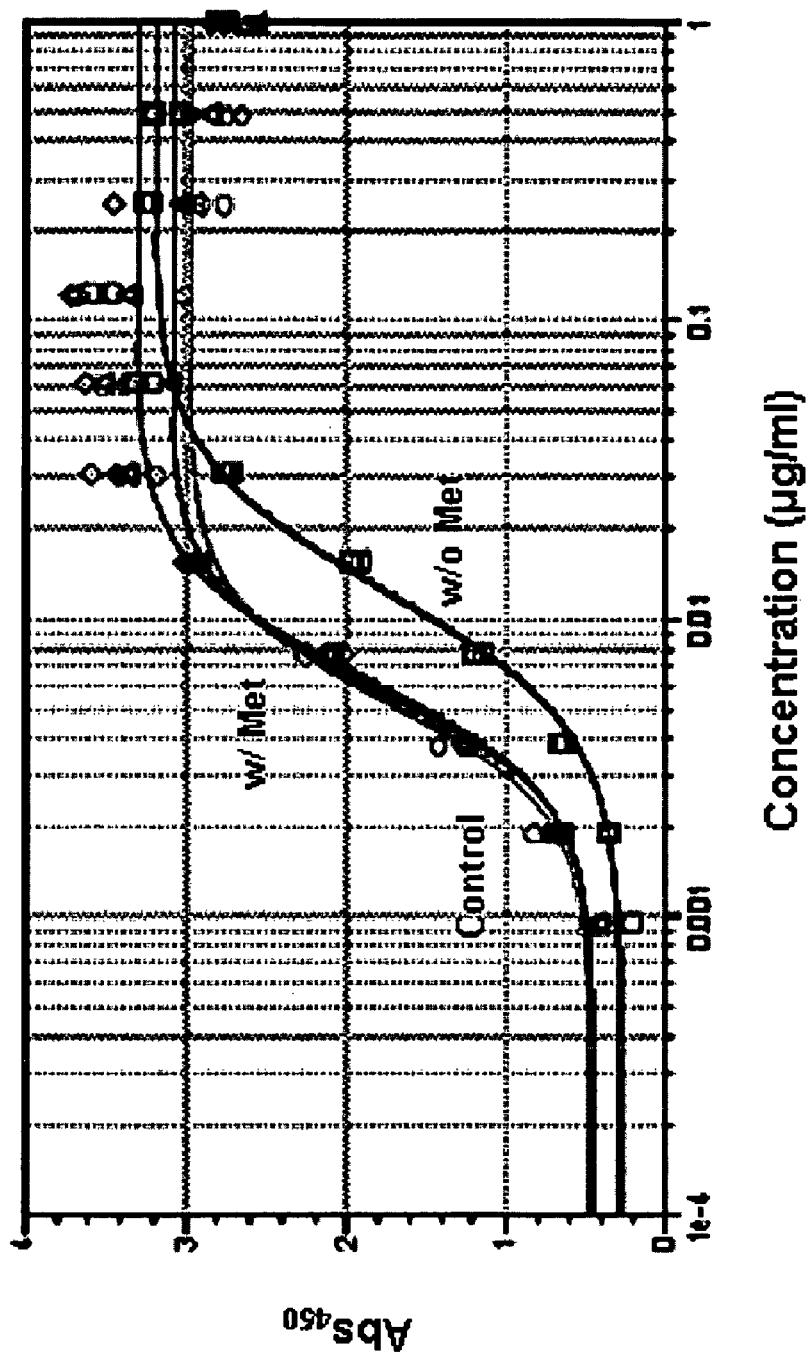
FIG. 30: Effect of methionine on XPA.10.064.06 binding affinity for hVEGF$_{165}$ following oxidation. A. ELISA analysis of XPA.10.064.06 binding to hVEGF$_{165}$ following oxidation by thermal stress in the presence or absence of methionine. B. ELISA analysis of XPA.10.064.06 binding to hVEGF$_{165}$ following oxidation by chemical stress in the presence or absence of methionine.
Figure 30B:
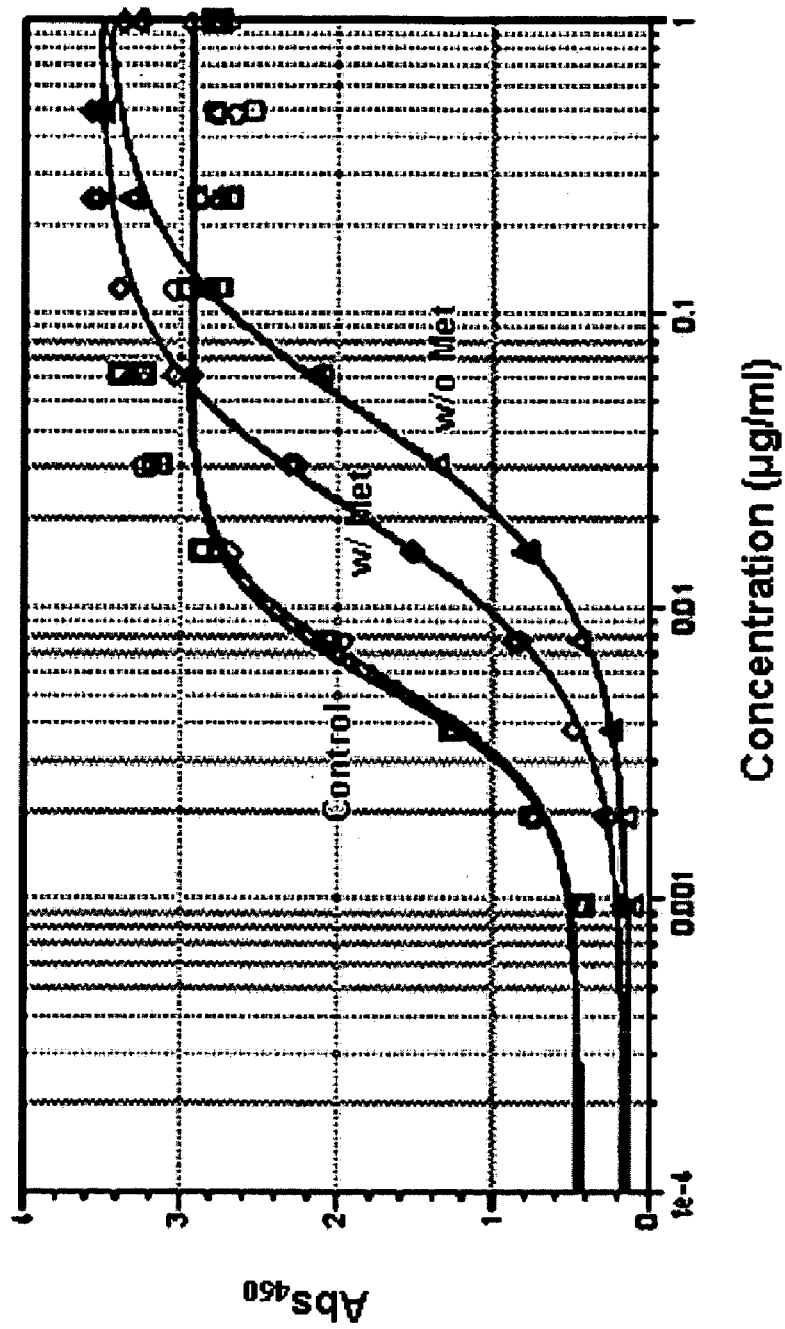

To overcome issues related to oxidation and increase stability of the affinity matured antibodies for long-term storage, formulations comprising XPA.10.064.06 plus an antioxidant agent were tested. XPA.10.064 and XPA.10.064.06 at 1 mg/ml in 10 mM L-histidine and 140 mM L-arginine (pH 6.0) were subjected to oxidation via chemical or thermal stress. For chemical stress, the antibodies were incubated overnight at room temperature with 0.1% tBHP in the presence or absence of 5 mM L-methionine. For thermal stress, the antibodies were incubated in polysorbate for four weeks at 40° C. in the presence or absence of 5 mM L-methionine. The ability of the antibodies to bind hVEGF$_{165}$ was analyzed by Biacore and ELISA. The presence of methionine in the antibody formulation conserved hVEGF$_{165}$ binding affinity in the presence of thermal stress (FIGS. 29A, 29B, and 30A), and reduced the negative effects on binding affinity of chemical stress (FIG. 30B). Results are summarized in Table 14.

TABLE 14

| Sample | Binding affinity (% control) | |
|---|---|---|
| | Biacore | ELISA |
| Thermal stress w/o Met | 36% | 42% |
| Thermal stress w/Met | 100% | 95% |
| Chemical stress w/o Met | 14% | 13% |
| Chemical stress w/Met | 28% | 31% |

Example 17

Further Affinity Maturation of XPA.10.064

Additional mutations may be introduced into the heavy chain variable region of XPA.10.064. Specifically, the methionine residue in XPA.10.064.06 HCDR3 may be mutated to one or more of alanine, lysine, proline, threonine, and leucine. The HCDR3 amino sequences of these mutants are set forth in SEQ ID NOs:25-29 respectively. Binding analysis will be conducted on antibodies containing the resulting HCDR3 sequences to determine binding affinity for hVEGF$_{165}$. Antibodies exhibiting high affinity for hVEGF$_{165}$ and an off rate faster than $10^{-5}$ will be reformatted to IgGs and subjected to functional analysis to determine their ability to inhibit HUVEC proliferation, angiogenesis, tumor growth, and/or hVEGF$_{165}$-induced phosphorylation of VEGF-R2.

Example 18

Expression of XPA.10.064.06

Figure 32:
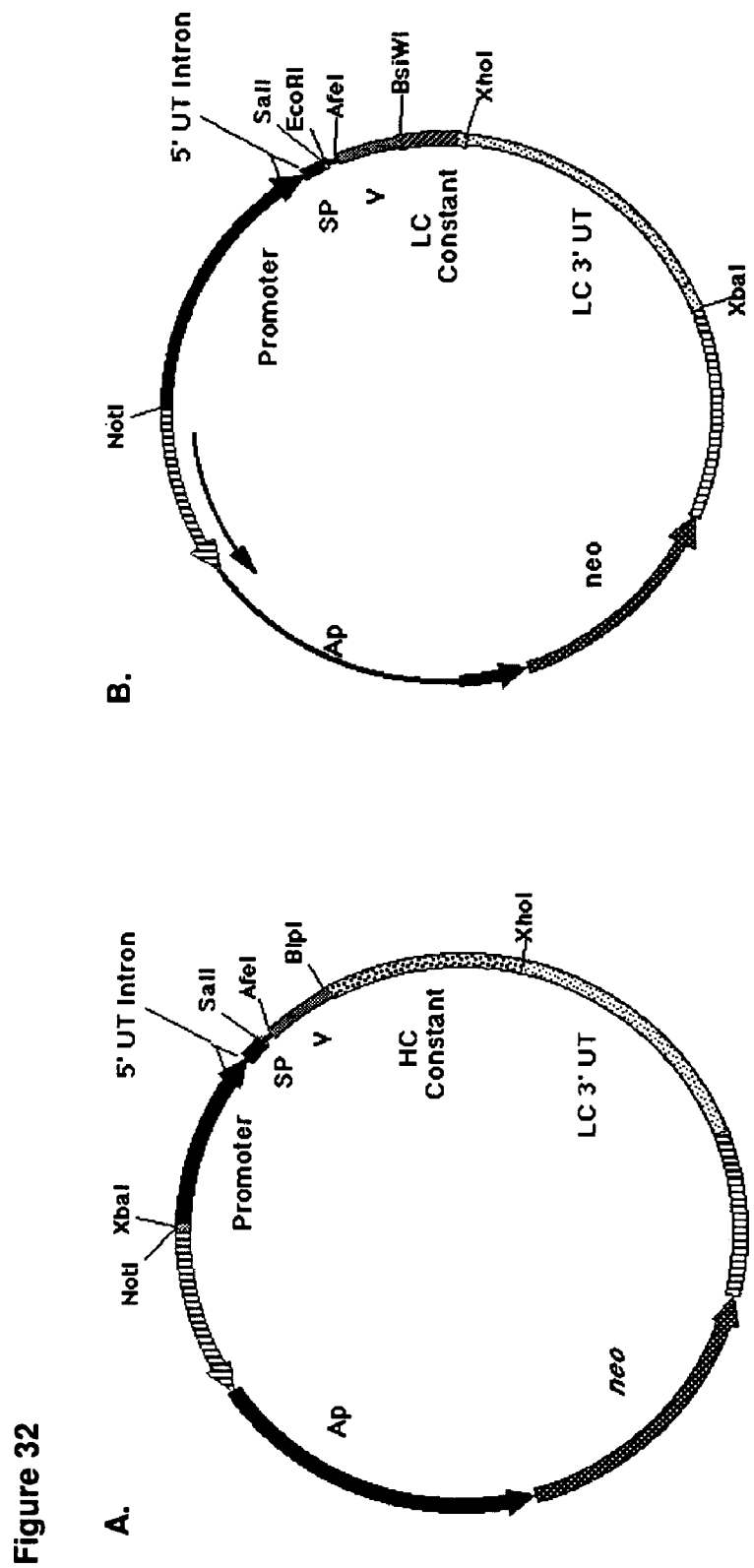
FIG. 32: XPA.10.064.06 heavy and light chain variable region modular expression vectors. A. Structure of heavy chain vector. B. Structure of light chain vector.

A first vector was constructed for expressing XPA.10.064.06 IgG$_2$ in CHO-K1 cells. This vector, pMXSP117, contains XPA.10.064.06 heavy and light chain variable regions fused to the Gamma-2 and Kappa constant regions, respectively, with each region under the control of the human CMV promoter and the mouse light chain 3' untranslated region. The vector contains the neo gene for selection of G418-resistant transfectants. The structure of pMXSP117 in circular and linearized form is set forth in FIGS. 31A and 31B, respectively. Prior to construction of pMXSP117, the XPA.10.064.06 heavy and light chain variable regions were cloned into modular expression vectors containing the heavy chain (Gamma-2) and light chain (Kappa) constant regions as shown in FIGS. 32A and 32B, respectively. The heavy chain variable region containing an antibody signal sequence was cloned as a SalI/BlpI fragment into the heavy chain modular vector. The light chain variable region containing an antibody signal sequence was cloned as a SalI/BsiWI fragment into the light chain modular vector.

A second vector, pMXSP119, which had the same structure as pMXSP117 but with the hisD gene (histidinol dehydrogenase) encoding resistance to histidinol in place of the neo gene, was constructed in two steps. The first step involved combining the XPA.10.064.006 heavy chain transcriptional unit with a vector segment containing the hisD gene to generate the vector pMXSP118. The second step involved combining a restriction fragment consisting of the XPA.10.064.06 light chain transcriptional unit with a vector segment from pMXSP118 containing the XPA.10.064.06 heavy chain transcriptional unit and the hisD gene to generate pMXSP119.

CHO-K1 cell lines were developed which express XPA.10.064.06 IgG$_2$. Prior to transfection, cells from a research cell bank of untransfected cells were thawed and grown in EX-CELL® 302 serum-free medium (SAFC Biosciences, Lenexa, Kans.). The genes encoding the light and heavy chains of XPA.10.064.06 were introduced into the animal product-free medium-adapted CHO-K1 cells by transfection using linear polyethylenimine (PEI; 25,000 MW; Polysciences, Warrington, Pa.) with pMXSP117 that had been linearized by digestion with XbaI (FIG. 31B). After incubation for three days in an animal product-free medium, the cells were suspended in EX-CELL® 302 medium supplemented with 0.8 mg/ml Geneticin® and 1% fetal bovine serum (FBS) and plated into 96-well plates. Wells containing single colonies were transferred to EX-CELL® 302 medium without FBS in deep well 96-well plates. After an additional screen by ELISA, the top producing clones were tested for expression in 50 ml vented tubes containing 10 ml of culture and 125 ml shake flasks containing 25 ml of culture.

Several of the top producers from this initial transfection with pMXSP117, selected based on their production capabilities, were adapted to a production medium for the purpose of producing XPA.10.064.06 IgG$_2$. To further increase production levels, the top Geneticin-resistant producer will be re-transfected with an additional vector expressing the same heavy and light chain sequences, but with a different selectable marker (e.g., the vector, pMXSP119 encoding resistance to histidinol). The pMXSP119 vector will be linearized by digestion with XbaI. After incubation for three days in an animal product-free medium, the cells are suspended in EX-CELL® 302 medium supplemented with 0.4 mg/ml Geneticin, 8 mM histidinol and 1% FBS and plated into 96-well plates. Wells containing single colonies identified as high producers by ELISA will be transferred to EX-CELL® 302 medium without FBS in deep well 96-well plates. After an additional screen by ELISA, the top producing clones will be tested for expression in shake flasks. Several of the top producers from this re-transfection, selected based on their growth and production capabilities, will be adapted to an animal product-free production medium for the purpose of evaluating growth and production in shake flask cultures and bioreactors. Research cell banks will be prepared for these top clones that have been adapted to a production medium. Based on the results of these tests, one clone will be chosen for preparation of a Master Cell Bank (MCB) which will serve as the starting point for manufacture of XPA.10.064.06 $IgG_2$ under Good Manufacturing Practice (GMP).

Example 19

Purification of XPA.10.064.06

Cells expressing XPA.10.064.06 or fragments thereof, such as the CHO-K1 cells described in Example 18, may be purified using the following procedure. After completion of fermentation, the cell culture is clarified and harvested by filtration through a filtration train comprising a depth filter (CUNO, Meriden, Conn.) followed by a charged membrane filter and then a sterile 0.2 μm filter. The cell-free clarified culture fluid is loaded onto a Protein A affinity column, which is then washed with equilibration buffer. The antibody is eluted with a low pH buffer in the pH 3-4 range, then subjected to viral inactivation at pH 3.8+/−0.2 for a maximum of 60 minutes. The viral-inactivated pool is adjusted for pH and conductivity, then loaded onto an anion exchange column in flow-through mode, whereby the antibody flows through the column while impurities bind. Flow-through from the anion exchange column is further purified over a hydrophobic interaction chromatography (HIC) column, which removes impurities such as aggregates, DNA, and host cell proteins, followed by filtration through a nano filter such as a Viresolve® Normal Flow Parvovirus (NFP) filter (Millipore) to remove viral particles. Using ultrafiltration and diafiltration (UF/DF), the nano filtered antibody pool is formulated to a target concentration and buffer exchanged into formulation buffer to yield bulk drug substance (BDS).

The foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference in their entirety as if fully set forth herein.

REFERENCES

1. Al-Lazikani, B., et al. 1997. J Mol Biol 273:927-948.
2. Amoroso, A., et al. 1997. Eur Rev Med Pharmacol Sci 1:17-25.
3. Ashida, S., et al. 2003. J Urol 169:2089-2093.
4. Atadja, P., et al. 2004. Cancer Res 64:689-695.
5. Azzazy, H. E., Highsmith, W. E. Jr. 2002. Clin Biochem 35:425-445.
6. Beisler, J. A. 1971. J Med Chem 14:1116-1118.
7. Berkman, R. A., et al. 1993. J Clin Invest 91:153-159.
8. Brown, L. F., et al. 1993. Cancer Res 53:4727-4735.
9. Brown, L. F., et al. 1995. Human Pathol 26:86-91.
10. Chaouche, M., et al. 2000. Am J Clin Oncol 23:288-289.
11. Chothia, C., et al. 1985. J Mol Biol 186:651-663.
12. Chothia, C., Lesk, A. M. 1987. J Mol Biol 196:901-917.
13. Chothia, C., et al. 1989. Nature 342:877-883.
14. Cumbers, S. J., et al. 2002. Nat Biotechnol 20:1129-1134.
15. Dancey, J. E. 2002. Curr Pharm Des 8:2259-2267.
16. de Gramont, A., et al. 2000. J Clin Oncol 18:2938-2947.
17. Dimmeler, S., Dernbach, E., Zeiher, A. M. 2000. FEBS Lett 477:258-262.
18. Dupont, J., et al. 2005. Proc Am Soc Clin Oncol 23:199s.
19. Dvorak, H. F., et al. 1995. Am J Pathol 146:1029-1039.
20. Elit, L. 2002. Curr Opin Investig Drugs 3:1249-1253.
21. Erlichman, C., et al. 2001. Cancer Res 61:739-748.
22. Erikkson, U., Alitalo, K. 1999. Curr Top Microbiol Immunol 237:41-57.
23. Ferrara, N. 1999. Curr Top Microbiol Immunol 237:1-30.
24. Ferrara, N., et al. 2004. Nat Rev Drug Discov 3:391-395.
25. Fishwild, D. M., et al. 1996. Nat Biotechnol 14:845-851.
26. Fry, D. W., et al. 1994. Science 265:1093-1095.
27. Fuh, G., et al. 2006. J Biol Chem 281:6625-6631.
28. Furumai, R., et al. 2002. Cancer Res 62:4916-4921.
29. Garner, R. C., et al. 2002. Drug Metab Dispos 30:823-830.
30. Gamido, J. L., et al. 1997. Cytobios 90:47-65.
31. Giri, J. G., et al. 1994. EMBO J 13:2822-2830.
32. Haddad, J. J. 2001. Curr Opin Investig Drugs 2:1070-1076.
33. Hamers-Casterman, C., et al. 1993. Nature 363:446-448.
34. Harris, A. L. 2000. Oncologist 5 Suppl 1:32-36.
35. Hawkins, R. E., Russell, S. J., Winter, G. 1992. J. Mol Biol. 226:889-896.
36. Hidalgo, M., et al. 2001. J Clin Oncol 19:3267-3279.
37. Holash, J., et al. 2002. Proc Natl Acad Sci USA 99:11393-11398.
38. Holliger, P., Prospero, T., Winter, G. 1993. Proc Natl Acad Sci USA 90:6444-6448.
39. Houston, et al. 1988. Proc Natl Acad Sci USA 85:5879-5883.
40. Hunt, J. T., et al. 2000. J Med Chem 43:3587-3595.
41. Hunt, S. 2001. Curr Opin Mol Ther 3:418-424.
42. Jianhua, H., Kontos, C. D. 2002. J Biol Chem 277:10760-10766.
43. Jostock, T., et al. 2004. J Immunol Methods 289:65-80.
44. Kabat, E. A., et al. 1987. Sequences of Proteins of Immunological Interest, 4th Edition, Public Health Service, NIH, Washington, D.C.
45. Kabat, E. A., et al. 1991. Sequences of Proteins of Immunological Interest, 5th Edition, Public Health Service, NIH, Washington, D.C.
46. Katre, N. V. 1990. J Immunol 144:209-213.
47. Katz, M. D., Erstad, B. L. 1989. Clin Pharm 8:255-273.
48. Khamaisi, M., et al. 2003. Nephrol Dial Transplant 18:1427-1430.
49. Kim, K. S., et al. 2003. J. Biol Chem 278:11449.
50. Kimbro, K. S., Simons, J. W. 2006. Endocr Relat Cancer 13:739-749.
51. Koch-Nolte, F., et al. 2007. FASEB J 21:3490-3498.
52. Lee, F. Y., et al. 2001. Clin Cancer Res 7:1429-1437.
53. Lee, Y. K., et al. 2004. Blood 104:788-794.
54. Li, J., et al. 2006. Proc Natl Acad Sci USA 103:3557-3562.
55. Liang, W-C, et al. 2006. J Biol Chem 281:951-961.
56. Lonberg, N. 2005. Nat Biotechnol 23:1117-1125.
57. Lowinger, T. B., et al. 2002. Curr Pharm Des 8:2269-2278.
58. Lowman, H. B. 1998. Phage display of peptide libraries on protein scaffolds. In S. Cabilly, Editor, *Methods in*

*Molecular Biology, vol. 87: Combinatorial Peptide Library Protocols*, Humana Press, Totowa, N.J., USA, pp. 249-264.
59. Mattern, J., Koomaqi, R., Volm, M. 1996. Brit J Cancer 73:931-934.
60. McColley, S. A., et al. 2000. Am J Respir Crit Care Med 161:1877-1880.
61. Mendel, D. B., et al. 2003. Clin Cancer Res 9:327-337.
62. Mendez, M. J., et al. 1997. Nat Genet 15:146-156.
63. Michaelis, M., et al. 2004. Mol Pharmacol 65:520-527.
64. Michels, S., Rosenfeld, P. J. 2004. Retinal Physician 1:16-22.
65. Michels, S., et al. 2005. Opthamology 112:1035-1047.
66. Murohara, T., et al. 1998. Circulation 97:99-107.
67. Muyldermans, S., Cambillau, C., Wyns, L. 2001. Trends Biochem Sci 26:230-235.
68. Nguyen, V. K., Desmyter, A., Muyldermans, S. 2001. Adv Immunol 79:261-296.
69. Nguyen, V. K., et al. 2002. Immunogenetics 54:39-47.
70. Panek, R. L., et al. 1997. J Pharmacol Exp Ther 283:1433-1444.
71. Riechmann, L., Muyldermans, S. 1999. J Immunol Methods 231:25.
72. Rosenfeld, P. J., Moshfeghi, A. A., Puliafito, C. A. 2005. Ophthalmic Surg Lasers Imaging 36:331-335.
73. Rusnak, D. W., et al. 2001. Mol Cancer Ther 1:85-94.
74. Sebolt-Leopold, J. S., et al. 1999. Nat Med 5:810-816.
75. Sehgal, S. N., et al. 1994. Med Res Rev 14:1-22.
76. Senderowicz, A. M. 2000. Oncogene 19:6600-6606.
77. Shields, R. L., Lai, J., Keck, R. 2002. J Biol Chem 277:26733-26740.
78. Shinkawa, T., et al. 2003. J Biol Chem 278:3466-3473.
79. Smaill, J. B., et al. 2000. J Med Chem 43:1380-1397.
80. Stork, G., Schultz, A. G. 1971. J Am Chem Soc 93:4074-4075.
81. Tamura, M., et al. 1998. Science 280:1614-1617.
82. Thomas, A. L., et al. 2003. Semin Oncol 30 (3 Suppl 6):32-38.
83. Tomizuka, K., et al. 2000. Proc Natl Acad Sci USA 97:722-727.
84. Vander Borght, T., et al. 1991a. Gastroenterology 101:794-799.
85. Vander Borght, T., et al. 1991b. Int J Rad Appl Instrum [A] 42:103-104.
86. Vlahos, C. J., et al. 1994. J Biol Chem 269: 5241-5248.
87. Wells, P., et al. 1996. Clin Oncol (R Coll Radiol) 8:7-14.
88. Wilhelm, S., Chien, D. S. 2002. Curr Pharm Des 8:2255-2257.
89. Wissner, A., et al. 2003. J Med Chem 46:49-63.
90. Yancopoulos, G. D., et al. 2000. Nature (London) 407:242-248.
91. Yang, X. D., et al. 1999. Cancer Res 59:1236-1243.
92. Yang, X. D., et al. 2001. Crit Rev Oncol Hematol 38:17-23.

What is claimed is:

1. An isolated antibody or antigen-binding fragment thereof that specifically binds VEGF and comprises a light chain immunoglobulin comprising CDR1 comprising the amino acid sequence set forth in SEQ ID NO: 12, CDR2 comprising the amino acid sequence set forth in SEQ ID NO: 13 and CDR3 comprising the amino acid sequence set forth in SEQ ID NO: 14 and a heavy chain immunoglobulin comprising CDR1 comprising the amino acid sequence set forth in SEQ ID NO: 6, CDR2 comprising the amino acid sequence set forth in SEQ ID NO: 7 and CDR3 comprising the amino acid sequence set forth in SEQ ID NO: 17.

2. The antibody or antigen-binding fragment thereof as recited in claim 1, comprising a light chain immunoglobulin comprising the amino acid sequence set forth in SEQ ID NO:5; and
a heavy chain immunoglobulin comprising the amino acid sequence set forth in SEQ ID NO:22.

3. The antibody or antigen-binding fragment thereof as recited in claim 1, wherein the antibody or antigen-binding fragment thereof is selected from the group consisting of a monoclonal antibody, a polyclonal antibody, a chimeric antibody, a humanized antibody, a recombinant antibody, a fully human antibody, a bivalent antibody, an anti-idiotypic antibody, a camelized single domain antibody, a diabody, a scFv, an scFv dimer, a dsFv, a $(dsFv)_2$, a dsFv-dsFv', an Fv fragment, a Fab, a Fab', a $F(ab')_2$, a ds diabody, a nanobody, a domain antibody, and a bivalent domain antibody.

4. The antibody or antigen-binding fragment thereof as recited in claim 1, further comprising an immunoglobulin constant region selected from the group consisting of a κ light chain, a γ1 heavy chain, a γ2 heavy chain, a γ3 heavy chain, and a γ4 heavy chain constant region.

5. The antibody or antigen-binding fragment thereof as recited in claim 1, wherein said antibody or antigen-binding fragment inhibits tumor growth as a function of percent tumor growth inhibition to the same or a greater degree than Bevacizumab when administered at a dosage selected from the group consisting of two-fold lower, three-fold lower, four-fold lower, and five-fold lower than Bevacizumab.

6. The antibody or antigen-binding fragment thereof as recited in claim 1, wherein said antibody or antigen-binding fragment inhibits tumor growth to a specified size for a time period selected from the group consisting of at least twice the duration of Bevacizumab and at least three times the duration of Bevacizumab when administered at the same or a lower dosage than Bevacizumab.

7. The antibody or antigen-binding fragment thereof as recited in claim 1, wherein said antibody or antigen-binding fragment binds to an epitope on human $VEGF_{165}$ that overlaps at least partially with the epitope bound by Bevacizumab.

8. The antibody or antigen-binding fragment thereof as recited in claim 1, wherein said antibody or antigen-binding fragment blocks binding of human $VEGF_{165}$ to VEGF-R1 and VEGF-R2.

9. The antibody or antigen-binding fragment thereof as recited in claim 1, wherein said antibody or antigen-binding fragment binds human $VEGF_{165}$ with a $K_D$ that is at least 10-fold, at least 50-fold or at least 100-lower than the $K_D$ of said antibody or antigen-binding fragment for binding to murine $VEGF_{165}$.

10. A pharmaceutical composition comprising the antibody or antigen-binding fragment thereof as recited in claim 1 and one or more antioxidants.

11. A pharmaceutical composition comprising the antibody or antigen-binding fragment thereof as recited in claim 1 and one or more pharmaceutically acceptable carriers.

12. The pharmaceutical composition of claim 10, wherein said one or more antioxidants are selected from the group consisting of methionine, ascorbic acid, EDTA, sodium thiosulfate, platinum, catalase, citric acid, cysteine, thioglycerol, thioglycolic acid, thiosorbitol, butylated hydroxanisol, butylated hydroxytoluene, and/or propyl gallate.

13. A pharmaceutical composition comprising the antibody or antigen-binding fragment thereof as recited in claim 1 in combination with one or more additional chemotherapeutic agents selected from the group consisting of capecitabine, a combination of irinotecan, 5-fluorouracil and leucovorin, carboplatin, leucovorin, oxaliplatin and 5-fluorouracil.

14. A complex comprising an antibody or antigen-binding fragment thereof as recited in claim 1 bound to human $VEGF_{165}$ or a fragment of human $VEGF_{165}$.

15. An isolated polypeptide comprising one or more amino acid sequences selected from the group consisting of SEQ ID NOs:5 and 22.

16. A method of inhibiting angiogenesis in a human subject in need thereof comprising administering to said subject a therapeutically effective amount of the antibody or antigen-binding fragment thereof as recited in claim 1, optionally linked to or in combination with one or more additional chemotherapeutic agents.

17. A method of treating a disease associated with aberrant angiogenesis in a human subject in need thereof comprising administering to said subject a therapeutically effective amount of the antibody or antigen-binding fragment thereof as recited in claim 1, optionally linked to or in combination with one or more additional chemotherapeutic agents.

18. A method of treating an inflammatory disease associated with VEGF signaling in a human subject in need thereof comprising administering to said subject a therapeutically effective amount of the antibody or antigen-binding fragment thereof as recited in claim 1, optionally linked to or in combination with one or more additional chemotherapeutic agents, wherein said disease is rheumatoid arthritis.

19. A method of treating wet acute macular degeneration or diabetic retinopathy in a human subject in need thereof comprising administering to said subject a therapeutically effective amount of the antibody or antigen-binding fragment thereof as recited in claim 1.

20. A method of treating a cancer associated with increased VEGF signaling in a human subject in need thereof comprising administering to said subject a therapeutically effective amount of the antibody or antigen-binding fragment thereof as recited in claim 1, optionally in combination with one or more additional chemotherapeutic agents, wherein said cancer is breast cancer.

21. A kit comprising the antibody or antigen-binding fragment thereof as recited in claim 1 and instructions for the use of said antibody or antigen-binding fragment.

* * * * *